United States Patent
Grimm et al.

(10) Patent No.: US 6,436,644 B1
(45) Date of Patent: *Aug. 20, 2002

(54) RIBOZYME TREATMENT OF DISEASES OR CONDITIONS RELATED TO LEVELS OF INTERCELLULAR ADHESION MOLECULE-1 (CAM-1)

(75) Inventors: Susan Grimm; Dan T. Stinchcomb; James McSwiggen; Sean Sullivan; Kenneth G. Draper, all of Boulder, CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/589,628

(22) Filed: Jun. 7, 2000

Related U.S. Application Data

(63) Continuation of application No. 09/071,845, filed on May 1, 1998, now Pat. No. 6,132,967, which is a continuation of application No. 08/292,620, filed on Aug. 17, 1994, now Pat. No. 5,837,542, which is a continuation-in-part of application No. 08/008,895, filed on Jan. 19, 1993, now abandoned, which is a continuation-in-part of application No. 07/989,849, filed on Dec. 7, 1992, now abandoned.

(51) Int. Cl.$^7$ .......................... C07H 21/04; C12Q 1/68; C12N 15/85
(52) U.S. Cl. .......................... 435/6; 435/91.1; 435/325; 435/375; 536/245
(58) Field of Search .......................... 435/6, 91.1, 325, 435/375; 536/23.1, 24.5

(56) References Cited

U.S. PATENT DOCUMENTS

| | | | |
|---|---|---|---|
| 5,168,053 | A | 8/1990 | Altman et al. |
| 4,987,071 | A | 1/1991 | Cech |
| 5,225,337 | A | 7/1993 | Robertson et al. |
| 5,837,542 | A | * 11/1998 | Grimm et al. ............... 435/366 |

FOREIGN PATENT DOCUMENTS

| | | |
|---|---|---|
| EP | 0 519 463 | 12/1992 |
| WO | 91/03162 | 3/1991 |
| WO | 91/15580 | 7/1991 |
| WO | 91/18624 | 12/1991 |
| WO | 91/18625 | 12/1991 |
| WO | 91/18913 | 12/1991 |
| WO | 92/07065 | 4/1992 |
| WO | 91/00080 | 9/1992 |
| WO | 93/15187 | 8/1993 |
| WO | 93/23569 | 11/1993 |
| WO | 94/02595 | 2/1994 |

OTHER PUBLICATIONS

Altmann et al., "Cotransfection of ICAM–1 and HLA–DR reconstitutes human antigen–presenting cell function in mouse L cells," *Nature* 338:512–514 (1989).

Ballantyne et al., "Nucleotide sequence of the cDNA for murine intercellular adhesion molecule–1 (ICAM–1)," *Nucleic Acids Research* 17:5853 (1989).

Baringa, "Ribozymes: Killing the messenger," *Science* 262:1512–1514 (1883).

Bowes et al., "Monoclonal Antibody to the ICAM–1 Adhesion Site Reduces Neurological Damage in a Rabbit Cerebral Embolism Stroke Model," *Experimental Neurology* 119:215–219 (1993).

Boyd et al., "Intercellular adhesion molecule 1 (ICAM–1) has a central role in cell–cell contact–mediated immune mechanisms," *Proc. Natl. Acad. Sci. USA* 85:3095–3099 (1988).

Cech, "Ribozymes and Their Medical Implications," *JAMA* 260:3030–3034 (1988).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chiang et al., "Antisense Oligonucleotides Inhibit Intercellular Adhesion Molecule 1 Expression by Two Distinct Mechanisms," *J. Biol. Chem.* 27:18162–18171 (1991).

Chin et al., "Role of Cytokines in Inflammatory Synovitis," *Arthritis and Rheumatism* 33:1776–1786 (1990).

Chowrira and Burke, "Extensive Phosphorothioate Substitution Yields Highly Active and Nuclease–Resistant Hairpin Ribozymes," *Nucleic Acids Research* , 20:2835–2840 (1992).

Collins and Olive, "Reaction Conditions and Kinetics of Self–Cleavage of a Ribozyme Derived From *Neurospora*VS RNA," *Biochemistry* 32:2795–2799 (1993).

Cosimi et al., "In Vivo Effects of Monoclonal Antibody to ICAM–I (CD45) in Nonhuman Primates with Renal Allografts," *Journal of Immunology* 144:4604–4612 (1990).

Cotten, "The in vivo application of ribozymes," *TIBTECH* 8:174–178 (1990).

Dang et al. "Role of ICAM–1 in Antigen Presentation Demonstrated by ICAM–1 Defective Mutants," *Journal of Immunology* 144:4082–4091 (1990).

Dropulic et al., "Functional Characterization of a U5 Ribozyme: Intracellular Suppression of Human Immunodeficiency Virus Type I Expression," *Journal of Virology* 66:1432–1441 (1992).

Dustin and Springer, "Lymphocyte Function–associated Antigen–1 (LFA–1) Interaction with Intercellular Adhesion Molecule–1 (ICAM–1) is One of at Least Three Mechanisms for Lymphocyte Adhesion to Cultured Endothelial Cells," *J. Cell. Biol.* 107:321–331 (1988).

(List continued on next page.)

*Primary Examiner*—Andrew Wang
(74) *Attorney, Agent, or Firm*—McDonnell Boehnen Hulbert & Berghoff

(57) ABSTRACT

The present invention relates to enzymatic RNA molecules which cleave ICAM-1 mRNA.

19 Claims, 6 Drawing Sheets

OTHER PUBLICATIONS

Dustin et al., "Induction by IL 1 and Interferon-□: Tissue Distribution. Biochemistry, and Function of a Natural Adherence Molecule (ICAM-1)[1]," *Journal of Immunology*, 137:245–254 (1986).

Edgington, "Ribozymes: Stop Making Sense," *Biotechnology* 10:256–262 (1992).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Flavin et al., "Monoclonal Antibodies Against Intercellular Adhesion Molecule 1 Prolong Cardiac Allograft Survival in Cynomolgus Monkeys," *Transplantation Proceedings* 23:533–534 (1991).

Fung et al., WO 91/1580 (Oct. 17, 1991) provided as WPI Abstract Acc. #91–325223144.

Furukawa et al., "Increased Levels of Circulating Intercellular Adhesion Molecule 1 in Kawasaki Disease," *Arthritis and Rheumatism* 35:672–677 (1992).

Furukawa et al., "Transient Depletion of T Cells with Bright CD11a/CD18 Expression from Peripheral Circulation during Acute Kawasaki Disease," *Scand. J. Immunol.* 37:377–380 (1993).

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Griffiths et al., "Characterization of intercellular adhesion molecule–1 and HLA–DR expression in normal and inflamed skin: Modulation by recombinant gamma interferon and tumor necrosis factor," *J. Am. Acad. Dermatol.* 20:617–629 (1989).

Guerrier–Takada et al., "The RNA Moiety of Ribonuclease P Is the Catalytic Subunit of the Enzyme," *Cell* 35:849–857 (1983).

Gundel et al., Clin. Exp. Allergy 22:569–575 (1992).

Hampel et al., "Hairpin' Catalytic RNA Model: Evidence for Helices and Sequence Requirement for Substrate RNA," *Nucleic Acids Research* 18:229–304 (1990).

Hampel and Tritz, "RNA Catalytic Properties of the Minimum (–)s TRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Huag et al., "A Phase I Trial of Immunosuppression With Anti–ICAM–1 (CD54) mAb in Renal Allograft Recipients," *Transplantation* 55:766–773 (1993).

Hertel et al., "Numbering System for the Hammerhead," *Nucleic Acids Research* 20:3252 (1992).

Hession et al., WO 90/13300 (Nov. 15, 1990) provided as CA Abstr. Acc. #114(25):292037g.

Jaeger et al., "Improved Predictions of Secondary Structures for RNA," *Proc. Natl. Acad. Sci. USA* 86:7706–7710 (1989).

Jeffries and Symons, "A Catalytic 13–mer Ribozyme," *Nucleic Acids Research* 17:1371–1377 (1989) (also referred to as Jefferies).

Johnston and Hoth, "Present Status and Future Prospects for HIV Therapies," *Science* 260:1286–1293 (1993).

Kakimoto et al., "The Effect of Anti–adhesion Molecule Antibody on the Development of Collagen–Induced Arthritis," *Cellular Immunology* 142:326–337 (1992).

Kashani–Sabet et al., "Reversal of the Malignant Phenotype by an Anti–*ras* Ribozyme," *Antisense Research & Development* 2:3–15 (1992).

Kellner et al., "Overexpression of extracellular matrix receptors (VLA–3, 5 and 6) on psoriatic keratinocytes," *British Journal of Dermatology* 125:211–216 (1991).

Kim and Cech, "Three–dimensional model of the active site of the self–splicing rRNA precursor of *Tetrahymena*," *Proc. Natl. Acad. Sci. USA* 84:8788–8792 (1987).

Kita et al., "Sequence and expression of rat ICAM–1," *Biochem. Biophys. Acta* 1131:108–110 (1992).

Koch et al., "Immunolocalization of Endothelial and Leukocyte Adhesion Molecules in Human Rheumatoid and Osteoarthritic Synovial Tissue," *Laboratory Investigation*, 64:313–320 (1991).

L'Huillier et al., "Cytoplasmic Delivery of Ribozymes Leads to Efficient Reduction in α–Lactalbumin mRNA Levels in C1271 Mouse," *EMBO J.*, 11:4411–4418 (1992).

Leung et al., "Endothelial Cell Activation and High Interleukin–1 Secretion in the Pathogenesis of Acute Kawasaki Disease," *The Lancet* 2:1298–1302 (1989).

Lieber et al., "Stable High–Level Gene Expression in Mammalian Cells by T7 Phage RNA Polymerase," *Methods Enzymol.* 217:47–66 (1993).

Ligo et al., "ICAM–1 dependent pathway is critically involved in the pathogenesis of adjuvant arthritis in rats," *Journal of Immunology* 147:4167–4171 (1991).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Ma et al., "Coronary Endothelial and Cardiac Protective Effects of a Monoclonal Antibody to Intercellular Adhesion Molecule–1 in Myocardial Ischemia and Reperfusion," *Circulation* 86:937–946 (1992).

Mamone et al., "Design of Hammerhead Ribozymes Targeted to Sequences in HIV, HSV and the RAT ANF Gene," Abstract of Keystone, CO (May 27, 1992).

Mason et al., "Detection of Increased Levels of Circulating Intercellular Adhesion Molecule 1 in Some Patients with Rheumatoid Arthritis But Not In Patients with Systemic Lupus Erythematosus," *Arthritis and Rheumatism* 36:519–527 (1993).

Nabel et al., "Site–Specific Gene Expression in Vivo by Direct Gene Transfer Into the Arterial Wall," *Science* 249:1285–1288 (1990).

Nickoloff et al., "Accessory Cell Function of Keratinocytes for Superantigens," *Journal of Immunology* 150:2148–2159 (1993).

Ohkawa et al., "Activities of HIV–RNA Targeted Ribozymes Transcribed From a 'Shot–Gun'Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Pavco et al., "Regulation of Self–Splicing Reactions by Antisense RNA," Abstract of Keystone, CO (May 27, 1992).

Perreault et al., "Mixed Deoxyribo–and Ribo–Oligonucleotides with Catalytic Activity," *Nature* 344:565–567 (1990) (often mistakenly listed as Perrault).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Rossi et al., "Ribozyme Mediated Intracellular Immunity to HIV–1 in CD4," *J. Cell Biochem.* Suppl 14A:374 at D428 (1990).

Rossi et al., "Ribozymes as Anti–HIV–1 as Therapeutic Agents: Principles, Applications, and Problems," *AiDSResearch and Human Retroviruses* 8:183–189 (1992).

Rothlein et al., "Induction of Intercellular Adhesion Molecule 1 on Primary and Continuous Cell Lines by Pro–Inflammatory Cytokines," *Journal of Immunology* 141:1665–1669 (1988).

Sarver et al., "Ribozymes as Potential Anti–HIV–1 Therapeutic Agents" *Science* 247:1222–1225 (1990).

Saville and Collins,"RNA–Mediated Ligation of Self–Cleavage Products of a *Neurospora* Mitochondrial Plasmid Transcript," *Proc. Natl. Acad. Sci. USA* 88:8826–8830 (1991).

Saville and Collins, "A Site–Specific Self–Cleavage Reaction Performed by a Novel RNA In Neurospora Mitochondria," *Cell* 61:685–696 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Schopf et al., "Soluble Intercellular Adhesion Molecule–1 Levels in Patients with Psoriasis," *British Journal of Dermatology* 128:34–37 (1993).

Simmons et al., "ICAM, an adhesion ligand of LFA–1, is homologous to the neural cell adhesion molecule NCAM," *Nature* 331:624–627 (1988).

Sioud et al., *J. Mol. Biol.* 223:831–835 (1992).

Springer et al., "The Lymphocyte Function–Associated LFA–1, CD2, and LFA–3 Molecules: Cell Adhesion Receptors of the Immune System," *Ann. Rev. Immunol.* 5:223–252 (1987).

Stull and Szoka, "Antigene, Ribozyme and Aptamer Nucleic Acid Drugs: Progress and Prospects," *Pharmaceutical Research* 12:465–483 (1995).

Taira et al., "Construction of a novel RNA–transcript–trimming plasmid which can be used in vitro in place of run–off and (G)–free transcriptions and in vivo as multi–sequences transcription vectors," *Nucleic Acids Research* 19:5125–5130 (1991).

Tanabe et al., *J. Biol. Chem.* 262:16580 (1987), provided as BIOSIS Abstr. 85047487.

Tsuji, "Soluble Intercellular Adhesion Molecule–1 Levels in Sera of Patients with Kawasaki Disease," *Arerugi* 41:1507–1514 (1992) (Japanese document with English Abstract).

Uhlenbeck, "A Small Catalytic Oligoribonucleotide," *Nature* 328:596–600 (1987) (this is listed as Nature 327 in the various specifications, but it is actually 328).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman and Cedergren, "Exploiting the chemical synthesis of RNA," *TIBS* 17:334–339 (1992).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–5534 (1994).

Wegner et al., "Intercellular Adhesion Molecule–1 (ICAM–1) in the Pathogenesis of Asthma," *Science* 247:456–458 (1990).

Willard et al., "Recombinant Adenovirus in an Efficient Vector for In Vivo Gene Transfer and can be Preferentially Directed at a Vascular Endothelium or Smooth Muscle Cells," *Circulation –Abstracts from the 6th Scientific Sessions*, New Orleans Convention Center, New Orleans, Louisiana, Nov. 16–19, 1992 86:I–473 at 1880.

Woolf et al., "Specificity of Antisense Oligonucleotides in vivo," *Proc. Natl. Acad. Sci. USA* 89:7305–7309 (1992).

Yoshida et al., "Anoxia/reoxygenation–induced neutrophil adherence to cultured endothelial cells," *Am. J. Physiol.* 262:H1891–H1898 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zaug and Cech, "The Tetrahymena Intervening Sequence Ribonucleic Acid Enzyme Is a Phosphotransferase and an Acid Phosphatase," *Biochemistry* 25:4478–4482 (1986).

Zhou et al., "Synthesis of Functional mRNA in Mammalian Cells by Bacteriophage T3 RNA Polymerase," *Mol. Cell. Biol.* 10:4529–4537 (1990).

\* cited by examiner

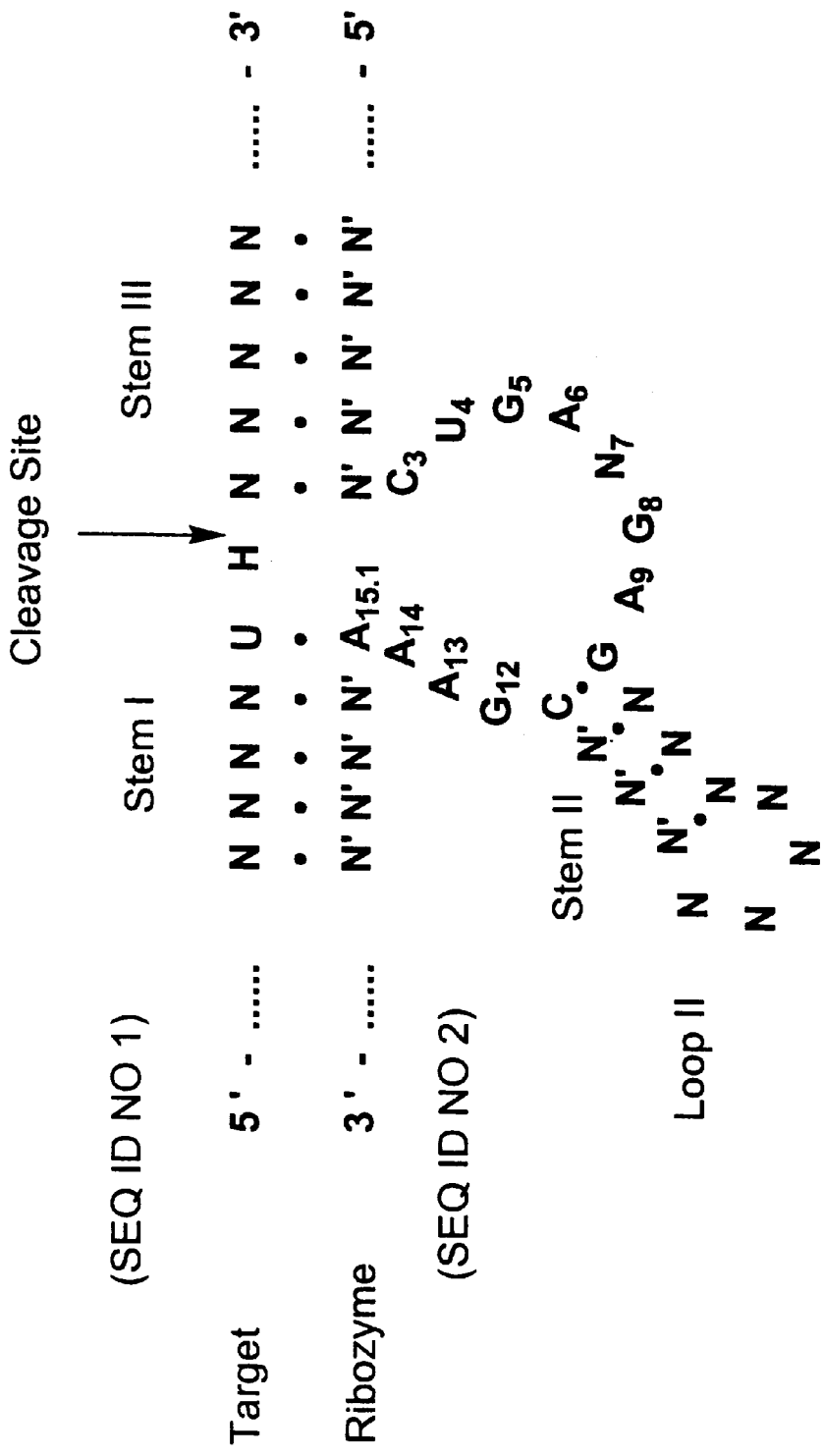
*Figure 1. The Hammerhead Ribozyme*

HAMMERHEAD RIBOZYME SUBSTRATE MOTIFS (SEQ ID NO 5)

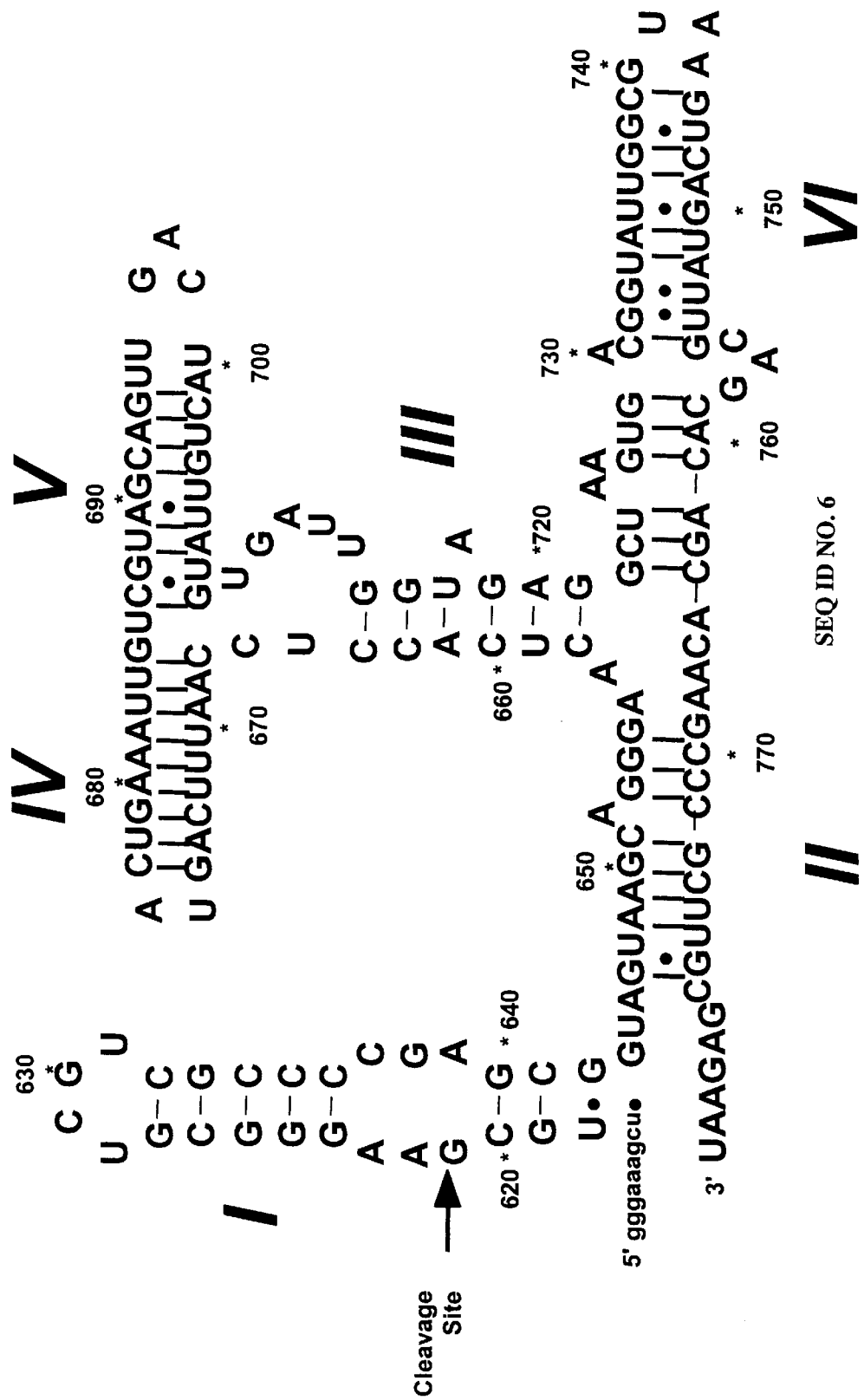
Figure 5. Neurospora VS Ribozyme

RNase H Assay

- Body-labeled transcript (not purified)
- DNA oligo (10 nM, 100 nM and 1000 nM)
- RNAse H (0.08 - 1.0 u/µl)
- 37°C, 10 min

RIBOZYME TREATMENT OF DISEASES OR CONDITIONS RELATED TO LEVELS OF INTERCELLULAR ADHESION MOLECULE-1 (CAM-1)

RELATED APPLICATIONS

This Application is a continuation of U.S. Ser. No. 09/071,845, filed May 1, 1998, now U.S. Pat. No. 6,132,967 which is a continuation of U.S. Ser. No. 08/292,620, filed Aug. 17, 1994, now U.S. Pat. No. 5,837,542, which is a continuation-in-part of U.S. Ser. No. 08/008,895, filed Jan. 19, 1993, now abandoned, which is a continuation-in-part of U.S. Ser. No. 07/989,849, now abandoned, filed Dec. 7, 1992, now abandoned, the entirety of each of these prior applications, including the drawings, are hereby incorporated by reference herein.

FIELD OF THE INVENTION

The present invention relates to therapeutic compositions and methods for the treatment or diagnosis of diseases or conditions related to ICAM-1 levels, such as transplant rejection, cancer, rheumatoid arthritis, asthma, reperfusion injury, and inflammatory or autoimmune disorders. For example, such treatments will be useful for transplant rejection, myocardial ischemia, stroke, psoriasis, and Kawasaki disease.

BACKGROUND OF THE INVENTION

The following is a brief description of the physiological role of ICAM-1. The discussion is not meant to be complete and is provided only for understanding of the invention that follows. This summary is not an admission that any of the work described below is prior art to the claimed invention.

Intercellular adhesion molecule-1 (ICAM-1) is a cell surface protein whose expression is induced by inflammatory mediators. ICAM-1 is required for adhesion of leukocytes to endothelial cells and for several immunological functions including antigen presentation, immunoglobulin production and cytotoxic cell activity. Blocking ICAM-1 function prevents immune cell recognition and activity during transplant rejection and in animal models of rheumatoid arthritis, asthma and reperfusion injury.

Cell-cell adhesion plays a pivotal role in inflammatory and immune responses (Springer et al., 1987 *Ann. Rev. Immunol.* 5, 223–252). Cell adhesion is required for leukocytes to bind to and migrate through vascular endothelial cells. In addition, cell-cell adhesion is required for antigen presentation to T cells, for B cell induction by T cells, as well as for the cytotoxicity activity of T cells, NK cells, monocytes or granulocytes. Intercellular adhesion molecule-1 (ICAM-1) is a 110 kilodalton member of the immunoglobulin superfamily that is involved in all of these cell-cell interactions (Simmons et al., 1988 *Nature* (London) 331, 624–627).

ICAM-1 is expressed on only a limited number of cells and at low levels in the absence of stimulation (Dustin et al., 1986 *J. Immunol.* 137, 245–254). Upon treatment with a number of inflammatory mediators (lipopolysaccharide, γ-interferon, tumor necrosis factor-α, or interleukin-1), a variety of cell types (endothelial, epithelial, fibroblastic and hematopoietic cells) in a variety of tissues express high levels of ICAM-1 on their surface (Sringer et. al. supra; Dustin et al., supra; and Rothlein et al., 1988 *J. Immunol.* 141, 1665–1669). Induction occurs via increased transcription of ICAM-1 mRNA (Simmons et al., supra). Elevated expression is detectable after 4 hours and peaks after 16–24 hours of induction.

ICAM-1 induction is critical for a number of inflammatory and immune responses. In vitro, antibodies to ICAM-1 block adhesion of leukocytes to cytokine-activated endothelial cells (Boyd, 1988 *Proc. Natl. Acad. Sci. USA* 85, 3095–3099; Dustin and Springer, 1988 *J. Cell Biol.* 107, 321–331). Thus, ICAM-1 expression may be required for the extravasation of immune cells to sites of inflammation. Antibodies to ICAM-1 also block T cell killing, mixed lymphocyte reactions, and T dell-mediated B cell differentiation, suggesting that ICAM-1 is required for these cognate cell interactions (Boyd et al., supra). The importance of ICAM-1 in antigen presentation is underscored by the inability of ICAM-1 defective murine B cell mutants to stimulate antigen-dependent T cell proliferation (Dang et al., 1990 *J. Immunol.* 144, 4082–4091). Conversely, murine L cells require transfection with human ICAM-1 in addition to HLA-DR in order to present antigen to human T cells (Altmann et al., 1989 *Nature* (London) 338, 512–514). In summary, evidence in vitro indicates that ICAM-1 is required for cell-cell interactions critical to inflammatory responses, cellular immune responses, and humoral antibody responses.

SUMMARY OF THE INVENTION

This invention relates to ribozymes, or enzymatic RNA molecules, directed to cleave mRNA species encoding ICAM-1. In particular, applicant describes the selection and function of ribozymes capable of cleaving this RNA and their use to reduce levels of ICAM-1 in various tissues to treat the diseases discussed herein. Such ribozymes are also useful for diagnostic uses.

Ribozymes that cleave ICAM-1 mRNA represent a novel therapeutic approach to inflammatory or autoimmune disorders. ICAM-1 function can be blocked therapeutically using monoclonal antibodies. Ribozymes have the advantage of being generally immunologically inert, whereas significant neutralizing anti-IgG responses can be observed with some monoclonal antibody treatments. Antisense DNA molecules have been described that block ICAM-1 expression (Chiang et al., 1991 *J. Biol. Chem.* 266, 18162–18171). However, ribozymes may show greater perdurance or lower effective doses than antisense molecules due to their catalytic properties and their inherent secondary and tertiary structures. Such ribozymes, with their catalytic activity and increased site specificity (as described below), represent more potent and safe therapeutic molecules than antisense oligonucleotides.

Applicant indicates that these ribozymes are able to inhibit expression of ICAM-1 and that the catalytic activity of the ribozymes is required for their inhibitory effect. Those of ordinary skill in the art, will find that it is clear from the examples described that other ribozymes that cleave target ICAM-1 encoding mRNAs may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992 *Proc. Natl. Acad. Sci. USA*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence). Examples of such hammerhead motifs are described by Rossi et al., 1992 *Aids Research and Human Retroviruses*, 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989 *Biochemistry*, 28, 4929 and Hampel et al., 1990 *Nucleic Acids Research* 18, 299, and an example of the hepatitis delta virus motif is described by Perrotta and Been, 1992, *Biochemistry* 31, 16, of the RNaseP motif by Guerrier-Takada et al., 1983 *Cell* 35, 849, of the Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target ICAM-1 encoding mRNA such that specific treatment of a disease; or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs. (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters,(e.g., Scanlon et al., 1991 *Proc. Natl. Acad. Sci. USA*, 88, 10591–5; Kashani-Sabet et al., 1992 *Antisense Res. Dev.* 2, 3–15; Dropulic et al., 1992 *J Virol.* 66, 1432–41; Weerasinghe et al., 1991 *J Virol.* 65, 5531–5534; Ojwang et al., 1992 *Proc. Natl. Acad. Sci. USA*, 89, 10802–10806; Chen et al., 1992 *Nucleic Acids Res.*, 20, 4581–1589; Sarver et al., 1990 *Science*, 247, 1222–1225). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992, *Nucleic Acids Symp. Ser.*, 27, 15–6; Taira et al., 1991 *Nucleic Acids Res.*, 19, 5125–5130; Ventura et al., 1993 *Nucleic Acids Res.*, 21, 3249–55).

Thus, in a first aspect, the invention features ribozymes that inhibit ICAM-1 production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target ICAM-1 encoding mRNAs, preventing translation and protein accumulation. In the absence of the expression of the target gene, a therapeutic effect may be observed.

By "inhibit" is meant that the activity or level of ICAM-1 encoding mRNA is reduced below that observed in the absense of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of ICAM-1 activity in a cell or tissue. By "related" is meant that the inhibition of ICAM-1 mRNA and thus reduction in the level of ICAM-1 will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues or cells ex vivo or in vivo by injection or through the use of a catheter, infusion pump or stent, with or without their incorporation in biopolymers. In preferred embodiments, the ribozymes have binding arms which are complementary to the sequences in Tables II, III, VI–IX. Examples of such ribozymes are shown in Tables IV–VIII and X. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit ICAM-1 activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.
Drawings:

FIG. 1 is a diagrammatic representation of the hammerhead ribozyme domain known in the art.

FIG. 2a is a diagrammatic representation of the hammerhead ribozyme domain known in the art; FIG. 2b is a diagrammatic representation of the hammerhead ribozyme as divided by Uhlenbeck (1987, Nature 327, 596–600) into a substrate and enzyme portion; FIG. 2c is a similar diagram showing the hammerhead divided by Haseloff and Gerlach (1988, Nature 334, 585–591) into two portions; and FIG. 2d is a similar diagram showing the hammerhead divided by Jeffries and Symons (1989, Nucl. Acids. Res. 17, 1371–1371) into two portions.

FIG. 5 is a representation of the general structure of the VS RNA ribozyme domain known in the art.

Figure 6B:
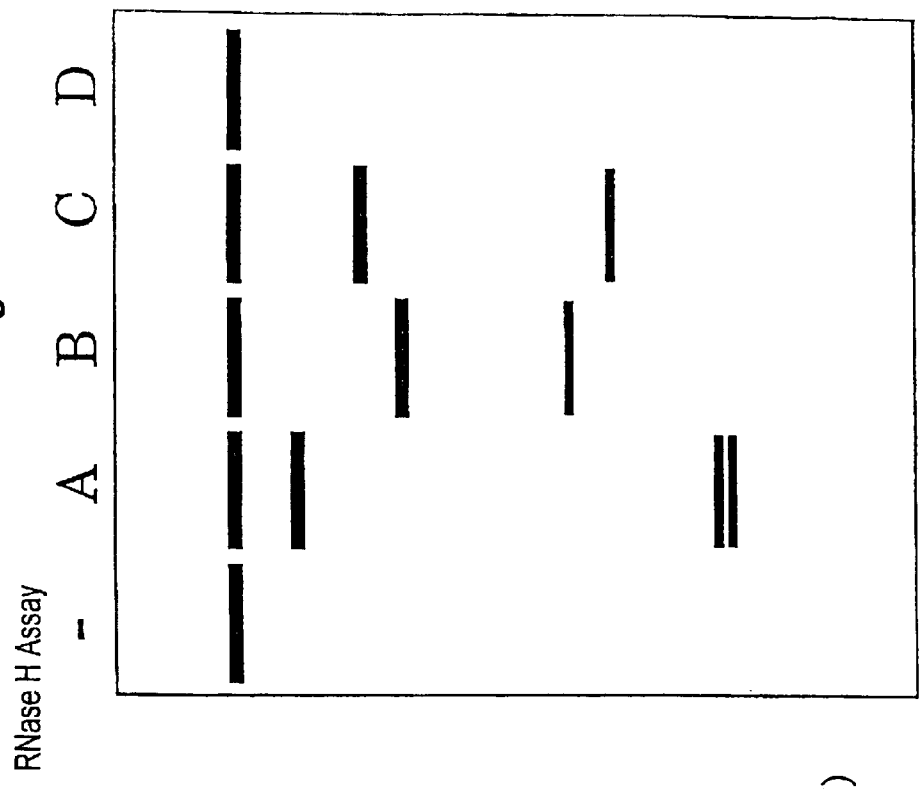
Figure 6A:
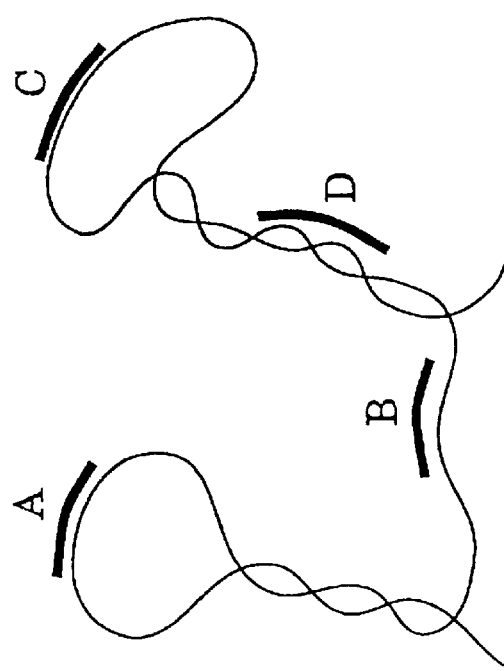

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, C, and D. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.
Ribozymes Ribozymes of this invention block to some extent ICAM-1 expression and can be used to treat disease or diagnose such disease. Ribozymes will be delivered to cells in culture and to tissues in animal models of transplant rejection and rheumatoid arthritis. Ribozyme cleavage of ICAM-1 mRNA in these systems may prevent inflammatory cell function and alleviate disease symptoms.
Target Sites Targets for useful ribozymes can be determined as disclosed in Draper et al supra. Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to rat, mouse and human RNA are provided, those in the art will recognize that the equivalent human RNA targets described can be used as described below. Thus, the same target may be used, but binding arms suitable for targetting human RNA sequences are present in the ribozyme. Such targets may also be selected as described below.

The sequence of human, rat and mouse ICAM-1 mRNA can be screened for accessible sites using a computer folding algorithm. Regions of the mRNA that did not form secondary folding structures and that contain potential hammerhead or hairpin ribozyme cleavage sites can be identified. These sites are shown in Tables II, III, and VI–IX. (All sequences are 5' to 3' in the tables.) While rat, mouse and human sequences can be screened and ribozymes thereafter designed, the human targetted sequences are of most utility. However, as discussed in Stinchcomb et al. "Method and Composition for Treatment of Restenosis and Cancer Using Ribozymes," U.S. Ser. No. 08/245,466, filed May 18, 1994, and hereby incorporated by reference herein, rat and mouse targetted ribozmes are useful to test efficacy of action of the ribozyme prior to testing in humans. The nucleotide base position is noted in the Tables as that site to be cleaved by the designated type of ribozyme. (In Table III, lower case letters indicate positions that are not conserved between the Human and the Mouse ICAM sequences.)

To test whether the sites predicted by the computer-based RNA folding algorithm correspond to accessible sites in the target mRNA, hammerhead sites are selected for analysis. Hammerhead ribozymes are designed that could bind and are individually analyzed by computer folding (Jaeger et al., 1989, Proc. Natl. Acad. Sci. USA, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in Draper et al., WO/U.S. Ser. No. 93/04020 and McSwiggen, U.S. patent application Ser. No. 07/883,849 filed May 1, 1992, entitled "Assay for ribozyme target site," both hereby incorporated by reference herein. Briefly, DNA oligonucleotides representing potential hammerhead ribozyme cleavage sites are synthesized. A polymerase chain reaction is used to generated a substrate for T7 RNA polymerase transcription from human or murine ICAM-1 cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead ribozyme sites are chosen as the most accessible.

Ribozymes of the hammerhead motif are designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.,* 109, 7845–7854 and in Scaringe et al., 1990 *Nucleic Acids Res.,* 18, 5433–5441, and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from (Hertel et al., *1992* Nucleic Acids Res., 20, 3252). Hairpin ribozymes are synthesized in two parts and annealed to reconstruct the active ribozyme (Chowrira and Burke, 1992 *Nucleic Acids Res.,* 20, 2835–2840). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736) the totality of which is hereby incorporated herein by reference) and were resuspended in water.

The sequences of the chemically synthesized ribozymes useful in this study are shown in Tables IV–VIII and X. Those in the art will recognize that these sequences are representative only of many more such sequences where the enzymatic portion of the ribozyme (all but the binding arms) is altered to affect activity and may be formed of ribonucleotides or other nucleotides or non-nucleotides. Such ribozymes are equivalent to the ribozymes described specifically in the Tables.

Optimizing Ribozyme Activity

Figure 2A:
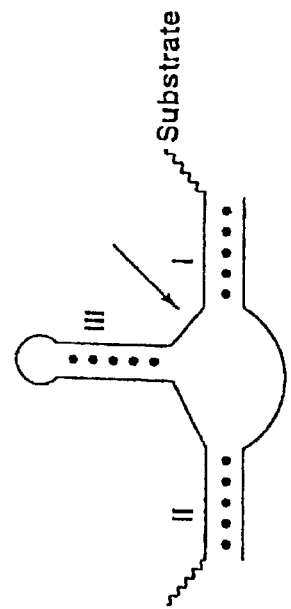
Figure 2B:
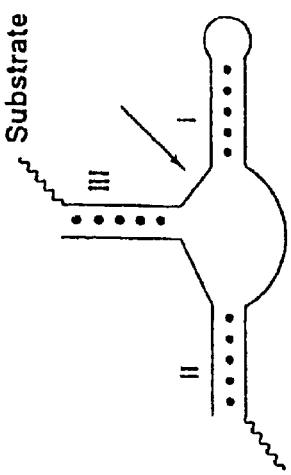
Figure 2C:
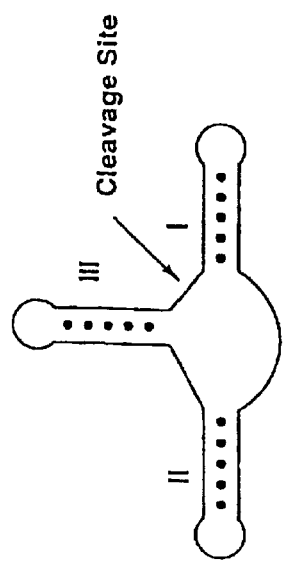
Figure 2D:
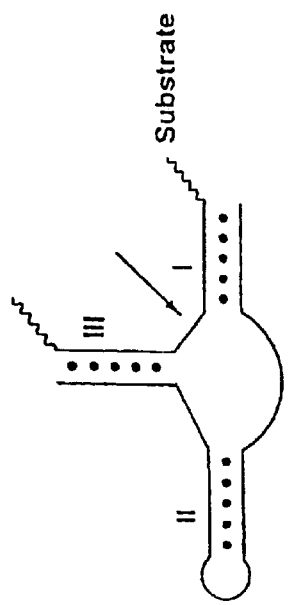

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., Nature 1990, 344:565; Pieken et al., Science 1991, 253:314; Usman and Cedergren, *Trends in Biochem. Sci.* 1992, 17:334; Usman et al., International Publication No. WO 93/15187; and Rossi et al., International Publication No. WO 91/03162, as well as Usman, N. et al. U.S. patent application Ser. No. 07/829,729, and Sproat, B. European Patent Application 92110298.4 which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pot I), RNA polymerase II (pot II), or RNA polymerase III (pot III). Transcripts from pot I or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U S A,* 87, 6743–7; Gao, and Huang, 1993 *Nucleic Acids Res.,* 21, 2867–72; Lieber et al., 1993 *Methods Enzymol.,* 217, 47–66; Zhou et al., 1990 *Mol. Cell. Biol.,* 10, 4529–37). Several investigators have demonstrated that ribozymes expressed from such promoters can function in mammalian cells (e.g. Kashani-Sabet, et al., 1992*Antisense Res. Dev.* 2, 3–15; Ojwang et al., 1992 *Proc. Natl. Acad. Sci. U S A* 89, 10802–6; Chen et al., 1992 *Nucleic Acids Res.,* 20, 4581–9; Yu et al., 1993*Proc. Natl. Acad. Sci. U S A* 90, 6340–4; L'Huillier, et al., 1992 *EMBO J.* 11, 4411–8; Lisziewicz et al., 1993 *Proc. Natl. Acad. Sci. U. S. A.* 90, 8000–4). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral vectors).

In a preferred embodiment of the invention, a transcription unit expressing a ribozyme that cleaves ICAM-1 RNA is inserted into a plasmid DNA vector or an adenovirus DNA viral vector. Both vectors have been used to transfer genes to the intact vasculature of live animals (Willard et al., 1992 *Circulation,* 86, I-473.; Nabel et al., 1990 *Science* 249, 1285–1288) and both vectors lead to transient gene expression. The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of a catheter, stent or infusion pump.

EXAMPLE 1

ICAM-1 Hammerhead Ribozymes

By engineering ribozyme motifs we have designed several ribozymes directed against ICAM-1 mRNA sequences. These have been synthesized with modifications that improve their nuclease resistance. These ribozymes cleave ICAM-1 target sequences in vitro.

The ribozymes will be tested for function in vivo by exogenous delivery to human umbilical vein endothelial cells (HUVEC). Ribozymes will be delivered by incorporation into liposomes, by complexing with cationic lipids, by microinjection, or by expression from DNA vectors. Cytokine-induced ICAM-1 expression will be monitored by ELISA, by indirect immunofluoresence, and/or by FACS analysis. ICAM-1 mRNA levels will be assessed by Northern, by RNAse protection, by primer extension or by quantitative RT-PCR analysis. Ribozymes that block the induction of ICAM-1 protein and mRNA by more than 90% will be identified.

RNA ribozymes and/or genes encoding them will be locally delivered to transplant tissue ex vivo in animal models. Expression of the ribozyme will be monitored by its ability to block ex vivo induction of ICAM-1 mRNA and protein. The effect of the anti-ICAM-1 ribozymes on graft rejection will then be assessed. Similarly, ribozymes will be introduced into joints of mice with collagen-induced arthritis or rabbits with Streptococcal cell wall-induced arthritis. Liposome delivery, cationic lipid delivery, or adeno-associated virus vector delivery can be used. One dose (or a few infrequent doses) of a stable anti-ICAM-1 ribozyme or a gene construct that constitutively expresses the ribozyme may abrogate inflammatory and immune responses in these diseases.

Uses

ICAM-1 plays a central role in immune cell recognition and function. Ribozyme inhibition of ICAM-1 expression can reduce transplant rejection and alleviate symptoms in patients with rheumatoid arthritis, asthma or other acute and chronic inflammatory disorders. We have engineered several ribozymes that cleave ICAM-1 mRNA. Ribozymes that efficiently inhibit ICAM-1 expression in cells can be readily found and their activity measured with regard to their ability to block transplant rejection and arthritis symptoms in animal models. These anti-ICAM-1 ribozymes represent a novel therapeutic for the treatment of immunological or inflammatory disorders.

The therapeutic utility of reduction of activity of ICAM-1 function is evident in the following disease targets. The noted references indicate the role of ICAM-1 and the therapeutic potential of ribozymes described herein. Thus, these targets can be therapeutically treated with agents that reduce ICAM-1 expression or function. These diseases and the studies that support a critical role for ICAM-1 in their pathology are listed below. This list is not meant to be complete and those in the art will recognize further conditions and diseases that can be effectively treated using ribozymes of the present invention.

Transplant Rejection

ICAM-1 is expressed on venules and capillaries of human cardiac biopsies with histological evidence of graft rejection (Briscoe et al., 1991 *Transplantation* 51, 537–539).

Antibody to ICAM-1 blocks renal (Cosimi et al., 1990*J. Immunol.* 144, 4604–4612) and cardiac (Flavin et al., 1991 *Transplant. Proc.* 23, 533–534) graft rejection in primates.

A Phase I clinical trial of a monoclonal anti-ICAM-1 antibody showed significant reduction in rejection and a significant increase in graft function in human kidney transplant patients (Haug, et al., 1993 *Transplantation* 55, 766–72).

Rheumatoid Arthritis

ICAM-1 overexpression is seen on synovial fibroblasts, endothelial cells, macrophages, and some lymphocytes (Chin et al., 1990 *Arthritis Rheum* 33, 1776–86; Koch et al., 1991 *Lab Invest* 64, 313–20).

Soluble ICAM-1 levels correlate with disease severity (Mason et al., 1993 *Arthritis Rheum* 36, 519–27).

Anti-ICAM antibody inhibits collagen-induced arthritis in mice (Kakimoto et al., 1992 *Cell Immunol* 142, 326–37).

Anti-ICAM antibody inhibits adjuvant-induced arthritis in rats (Iigo et al., 1991 *J Immunol* 147, 4167–71).

Myocardial Ischemia, Stroke, and Reperfusion Injury

Anti-ICAM-1 antibody blocks adherence of neutrophils to anoxic endothelial cells (Yoshida et al., 1992 *Am J Physiol* 262, H1891–8).

Anti-ICAM-1 antibody reduces neurological damage in a rabbit model of cerebral stroke (Bowes et al., 1993 *Exp Neurol* 119, 215–9).

Anti-ICAM-1 antibody protects against reperfusion injury in a cat model of myocardial ischemia (Ma et al., 1992*Circulation* 86, 937–46).

Asthma

Antibody to ICAM-1 partially blocks eosinophil adhesion to endothelial cells and is overexpressed on inflamed airway endothelium and epithelium in vivo (Wegner et al., 1990 *Science* 247, 456–9).

In a primate model of asthma, anti-ICAM-1 antibody blocks airway eosinophilia (Wegner et al., supra) and prevents the resurgence of airway inflammation and hyper-responsiveness after dexamethosone treatment (Gundel et al., 1992 *Clin Exp Allergy* 22, 569–75).

Psoriasis

Surface ICAM-1 and a clipped, soluble version of ICAM-1 is expressed in psoriatic lesions and expression correlates with inflammation (Kellner et al., 1991 *Br J Dermatol* 125, 211–6; Griffiths 1989 *J Am Acad Dermatol* 20, 617–29; Schopf et al., 1993 *Br J Dermatol* 128, 34–7).

Anti-ICAM antibody blocks keratinocyte antigen presentation to T cells (Nickoloff et al., 1993 *J Immunol* 150, 2148–59).

Kawasaki Disease

Surface ICAM-1 expression correlates with the disease and is reduced by effective immunoglobulin treatment (Leung, et al., 1989 *Lancet* 2, 1298–302).

Soluble ICAM levels are elevated in Kawasaki disease patients; particularly high levels are observed in patients with coronary artery lesions (Furukawa et al., 1992*Arthritis Rheum* 35, 672–7; Tsuji, 1992 *Arerugi* 41, 1507–14).

Circulating LFA-1$^+$ T cells are depleted (presumably due to ICAM-1 mediated extravasation) in Kawasaki disease patients (Furukawa et al., 1993 *Scand J Immunol* 37, 377–80).

Diagnostic Uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets.

may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an ICAM-1 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., ICAM-1) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cieavage site.
Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Figure 3:
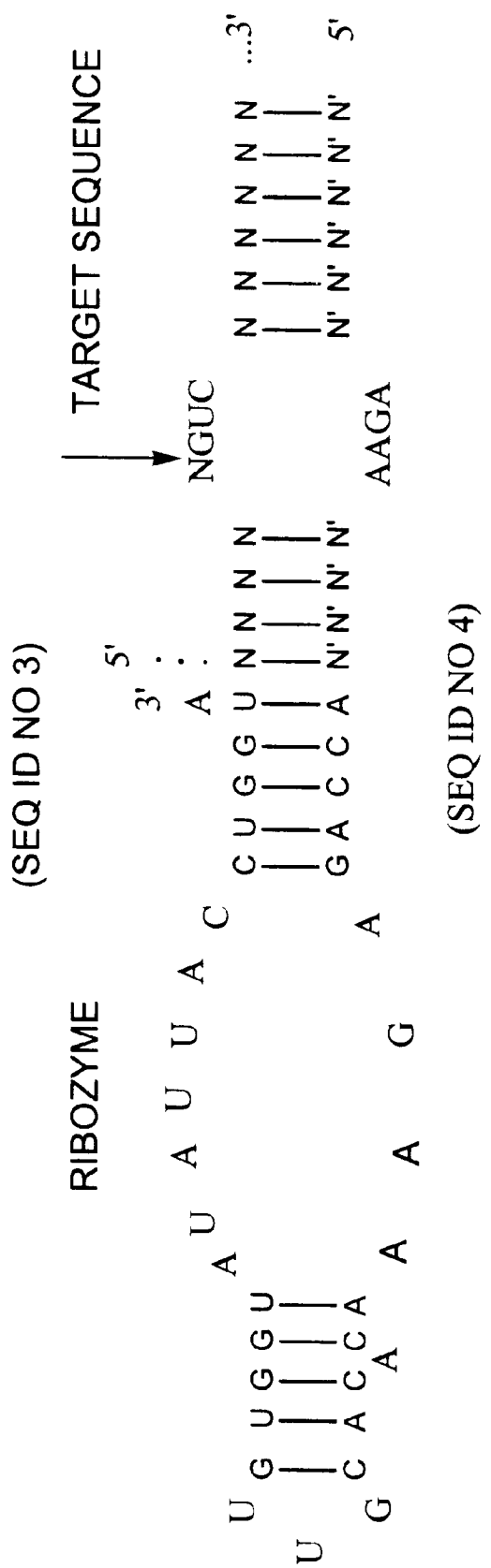
FIG. 3 is a representation of the general structure of the hairpin ribozyme domain known in the art.

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Figure 4:
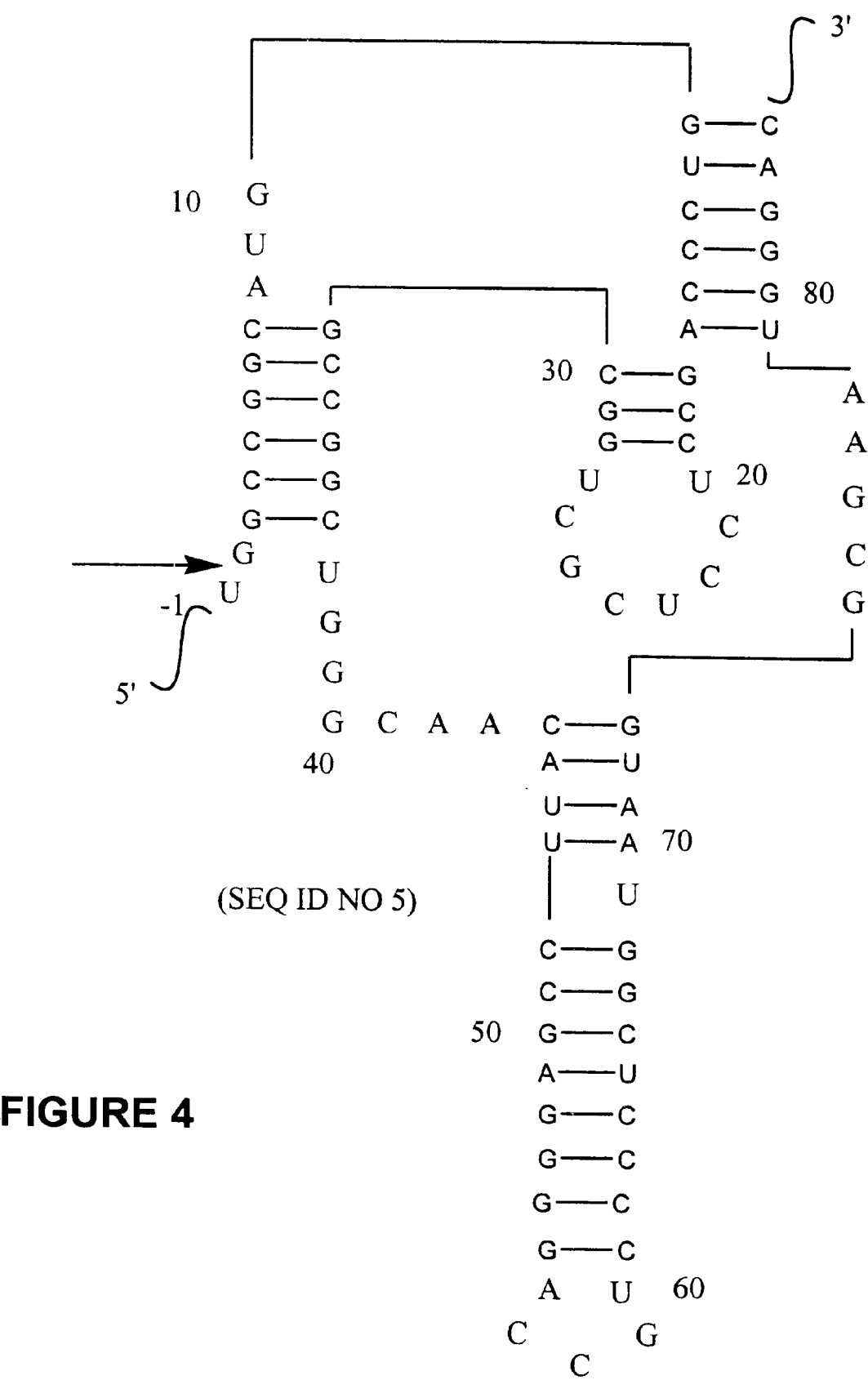
FIG. 4 is a representation of the general structure of the hepatitis delta virus ribozyme domain known in the art.

Size: 50–60 nucleotides (at present).
Cleavage of target RNAs recently demonstrated.
Sequence requirements not fully determined
Binding sites and structural requirements not fully determined, although no sequences 5' of cleavage site are required.
Only 1 known member of this class. Found in human HDV (FIG. 4)

Neurospora VS RNA Ribozyme

Size: ~144 nucleotides (at present)
Cleavage of target RNAs recently demonstrated.
Sequence requirements not fully determined.
Binding sites and structural requirements not fully determined.
Only 1 known member of this class. Found in Neurospora VS RNA (FIG. 5).

Table II
Human ICAM HH Target sequence

| nt. Position | SEQ ID NO | Target Sequences | nt. Position | SEQ ID NO | Target Sequences |
|---|---|---|---|---|---|
| 11 | 7 | CCCCAGU C GACGCUG | 386 | 47 | ACCGUGU A CUGGACU |
| 23 | 8 | CUGAGCU C CUCUGCU | 394 | 48 | CUGGACU C CAGAACG |
| 26 | 9 | AGCUCCU C UGCUACU | 420 | 49 | CACCCCU C CCCUCUU |
| 31 | 10 | CUCUGCU A CUCAGAG | 425 | 50 | CUCCCCU C UUGGCAG |
| 34 | 11 | UGCUACU C AGAGUUG | 427 | 51 | CCCCUCU U GGCAGCC |
| 40 | 12 | UCAGAGU U GCAACCU | 450 | 52 | AGAACCU U ACCCUAC |
| 48 | 13 | GCAACCU C AGCCUCG | 451 | 53 | GAACCUU A CCCUACG |
| 54 | 14 | UCAGCCU C GCUAUGG | 456 | 54 | UUACCCU A CGCUGCC |
| 58 | 15 | CCUCGCU A UGGCUCC | 495 | 55 | CCAACCU C ACCGUGG |
| 64 | 16 | UAUGGCU C CCAGCAG | 510 | 56 | UGCUGCU C CGUGGGG |
| 96 | 17 | CCGCACU C CUGGUCC | 564 | 57 | CUGAGGU C ACGACCA |
| 102 | 18 | UCCUGGU C CUGCUCG | 592 | 58 | GAGAGAU U ACCAUGG |
| 108 | 19 | UCCUGCU C GGGGCUC | 607 | 59 | AGCCAAU U UCUCGUG |
| 115 | 20 | CGGGGCU C UGUUCCC | 608 | 60 | GCCAAUU U CUCGUGC |
| 119 | 21 | GCUCUGU U CCCAGGA | 609 | 61 | CCAAUUU C UCGUGCC |
| 120 | 22 | CUCUGUU C CCAGGAC | 611 | 62 | AAUUUCU C GUGCCGC |
| 146 | 23 | CAGACAU C UGUGUCC | 656 | 63 | GAGCUGU U UGAGAAC |
| 152 | 24 | UCUGUGU C CCCCUCA | 657 | 64 | AGCUGUU U GAGAACA |
| 158 | 25 | UCCCCCU C AAAAGUC | 668 | 65 | AACACCU C GGCCCCC |
| 165 | 26 | CAAAAGU C AUCCUGC | 677 | 66 | GCCCCCU A CCAGCUC |
| 168 | 27 | AAGUCAU C CUGCCCC | 684 | 67 | ACCAGCU C CAGACCU |
| 185 | 28 | GGAGGCU C CGUGCUG | 692 | 68 | CAGACCU U UGUCCUG |
| 209 | 29 | AGCACCU C CUGUGAC | 693 | 69 | AGACCUU U GUCCGC |
| 227 | 30 | CCCAAGU U GUUGGGC | 696 | 70 | CCUUUGU C CUGCCAG |
| 230 | 31 | AAGUUGU U GGGCAUA | 709 | 71 | AGCGACU C CCCCACA |
| 237 | 32 | UGGGCAU A GAGACCC | 720 | 72 | CACAACU U GUCAGCC |
| 248 | 33 | ACCCCGU U GCCUAAA | 723 | 73 | AACUUGU C AGCCCCC |
| 253 | 34 | GUUGCCU A AAAAGGA | 735 | 74 | CCCGGGU C CUAGAGG |
| 263 | 35 | AAGGAGU U GCUCCUG | 738 | 75 | GGGUCCU A GAGGUGG |
| 267 | 36 | AGUUGCU C CUGCCUG | 765 | 76 | CCGUGGU C UGUUCCC |
| 293 | 37 | AAGGUGU A UGAACUG | 769 | 77 | GGUCUGU U CCCUGGA |
| 319 | 38 | AGAAGAU A GCCAACC | 770 | 78 | GUCUGUU C CCUGGAC |
| 335 | 39 | AUGUGCU A UUCAAAC | 785 | 79 | GGGCUGU U CCCAGUC |
| 337 | 40 | GUGCUAU U CAAACUG | 786 | 80 | GGCUGUU C CCAGUCU |
| 338 | 41 | UGCUAUU C AAACUGC | 792 | 81 | UCCCAGU C UCGGAGG |
| 359 | 42 | GGGCAGU C AACAGCU | 794 | 82 | CCAGUCU C GGAGGCC |
| 367 | 43 | AACAGCU A AAACCUU | 807 | 83 | CCCAGGU C CACCUGG |
| 374 | 44 | AAAACCU U CCUCACC | 833 | 84 | CAGAGGU U GAACCCC |
| 375 | 45 | AAACCUU C CUCACCG | 846 | 85 | CCACAGU C ACCUAUG |

21

| | | | | | |
|---|---|---|---|---|---|
| 378 | 46 | CCUUCCU C ACCGUGU | 851 | 86 | GUCACCU A UGGCAAC |
| 863 | 87 | AACGACU C CUUCUCG | 1408 | 136 | UCGAGAU C UUGAGGG |
| 866 | 88 | GACUCCU U CUCGGCC | 1410 | 137 | GAGAUCU U GAGGGCA |
| 867 | 89 | ACUCCUU C UCGGCCA | 1421 | 138 | GGCACCU A CCUCUGU |
| 869 | 90 | UCCUUCU C GGCCAAG | 1425 | 139 | CCUACCU C UGUCGGG |
| 881 | 91 | AAGGCCU C AGUCAGU | 1429 | 140 | CCUCUGU C GGGCAG |
| 885 | 92 | CCUCAGU C AGUGUGA | 1444 | 141 | GAGCACU C AAGGGA |
| 933 | 93 | GUGCAGU A AUACUGG | 1455 | 142 | GGGAGGU C ACCCGCG |
| 936 | 94 | CAGUAAU A CUGGGGA | 1482 | 143 | AUGUGCU C UCCCCCC |
| 978 | 95 | UGACCAU C UACAGCU | 1484 | 144 | GUGCUCU C CCCCCGG |
| 980 | 96 | ACCAUCU A CAGCUUU | 1493 | 145 | CCCCGGU A UGAGAUU |
| 986 | 97 | UACAGCU U UCCGGCG | 1500 | 146 | AUGAGAU U GUCAUCA |
| 987 | 98 | ACAGCUU U CCGGCGC | 1503 | 147 | AGAUUGU C AUCAUCA |
| 988 | 99 | CAGCUUU C CGGCGCC | 1506 | 148 | UUGUCAU C AUCACUG |
| 1005 | 100 | ACGUGAU U CUGACGA | 1509 | 149 | UCAUCAU C ACUGUGG |
| 1006 | 101 | CGUGAUU C UGACGAA | 1518 | 150 | CUGUGGU A GCAGCCG |
| 1023 | 102 | CAGAGGU C UCAGAAG | 1530 | 151 | CCGCAGU C AUAAUGG |
| 1025 | 103 | GAGGUCU C AGAAGGG | 1533 | 152 | CAGCAU A AUGGGCA |
| 1066 | 104 | CCACCCU A GAGCCAA | 1551 | 153 | CAGGCCU C AGCACGU |
| 1092 | 105 | AUGGGGU U CCAGCCC | 1559 | 154 | AGCACGU A CCUCUAU |
| 1093 | 106 | UGGGGUU C CAGCCCA | 1563 | 155 | CGUACCU C UAUAACC |
| 1125 | 107 | CCCAGCU C CUGCUGA | 1565 | 156 | UACCUCU A UAACCGC |
| 1163 | 108 | CGCAGCU U CUCCUGC | 1567 | 157 | CCUCUAU A ACCGCCA |
| 1164 | 109 | GCAGCUU C UCCUGCU | 1584 | 158 | GGAAGAU C AAGAAAU |
| 1166 | 110 | AGCUUCU C CUGCUCU | 1592 | 159 | AAGAAAU A CAGACUA |
| 1172 | 111 | UCCUGCU C UGCAACC | 1599 | 160 | ACAGACU A CAACAGG |
| 1200 | 112 | GCCAGCU U AUACACA | 1651 | 161 | CACGCCU C CCUGAAC |
| 1201 | 113 | CCAGCUU A UACACAA | 1661 | 162 | UGAACCU A UCCCGGG |
| 1203 | 114 | AGCUUAU A CACAAGA | 1663 | 163 | AACCUAU C CCGGGAC |
| 1227 | 115 | GGGAGCU U CGUGUCC | 1678 | 164 | AGGGCCU C UUCCUCG |
| 1228 | 116 | GGAGCUU C GUGUCCU | 1680 | 165 | GGCCUCU U CCUCGGC |
| 1233 | 117 | UUCGUGU C CUGUAUG | 1681 | 166 | GCCUCUU C CUCGGCC |
| 1238 | 118 | GUCCUGU A UGGCCCC | 1684 | 167 | UCUUCCU C GGCCUUC |
| 1264 | 119 | GAGGGAU U GUCCGGG | 1690 | 168 | UCGGCCU U CCCAUAU |
| 1267 | 120 | GGAUUGU C CGGGAAA | 1691 | 169 | CGGCCUU C CCAUAUU |
| 1294 | 121 | AGAAAAU U CCCAGCA | 1696 | 170 | UUCCCAU A UUGGUGG |
| 1295 | 122 | GAAAAUU C CCAGCAG | 1698 | 171 | CCCAUAU U GGUGGCA |
| 1306 | 123 | GCAGACU C CAAUGUG | 1737 | 172 | AAGACAU A UGCCAUG |
| 1321 | 124 | CCAGGCU U GGGGGAA | 1750 | 173 | UGCAGCU A CACCUAC |
| 1334 | 125 | AACCCAU U GCCCGAG | 1756 | 174 | UACACCU A CCGGCCC |
| 1344 | 126 | CCGAGCU C AAGUGUC | 1787 | 175 | AGGGCAU U GUCCUCA |
| 1351 | 127 | CAAGUGU C UAAAGGA | 1790 | 176 | GCAUUGU C CUCAGUC |
| 1353 | 128 | AGUGUCU A AAGGAUG | 1793 | 177 | UUGUCCU C AGUCAGA |
| 1366 | 129 | UGGCACU U UCCCACU | 1797 | 178 | CCUCAGU C AGAUACA |
| 1367 | 130 | GGCACUU U CCCACUG | 1802 | 179 | GUCAGAU A CAACAGC |
| 1368 | 131 | GCACUUU C CCACUGC | 1812 | 180 | ACAGCAU U UGGGGCC |
| 1380 | 132 | UGCCCAU C GGGGAAU | 1813 | 181 | CAGCAUU U GGGGCCA |
| 1388 | 133 | GGGGAAU C AGUGACU | 1825 | 182 | CCAUGGU A CCUGCAC |

| | | | | | |
|---|---|---|---|---|---|
| 1398 | 134 | UGACUGU C ACUCGAG | 1837 | 183 | CACACCU A AAACACU |
| 1402 | 135 | UGUCACU C GAGAUCU | 1845 | 184 | AAACACU A GGCCACG |
| 1856 | 185 | CACGCAU C UGAUCUG | 2189 | 234 | UAUUUAU U GAGUGUC |
| 1861 | 186 | AUCUGAU C UGUAGUC | 2196 | 235 | UGAGUGU C UUUUAUG |
| 1865 | 187 | GAUCUGU A GUCACAU | 2198 | 236 | AGUGUCU U UUAUGUA |
| 1868 | 188 | CUGUAGU C ACAUGAC | 2199 | 237 | GUGUCUU U UAUGUAG |
| 1877 | 189 | CAUGACU A AGCCAAG | 2200 | 238 | UGUCUUU U AUGUAGG |
| 1901 | 190 | CAAGACU C AAGACAU | 2201 | 239 | GUCUUUU A UGUAGGC |
| 1912 | 191 | ACAUGAU U GAUGGAU | 2205 | 240 | UUUAUGU A GGCUAAA |
| 1922 | 192 | UGGAUGU U AAAGUCU | 2210 | 241 | GUAGGCU A AAUGAAC |
| 1923 | 193 | GGAUGUU A AAGUCUA | 2220 | 242 | UGAACAU A GGUCUCU |
| 1928 | 194 | UUAAAGU C UAGCCUG | 2224 | 243 | CAUAGGU C UCUGGCC |
| 1930 | 195 | AAAGUCU A GCCUGAU | 2226 | 244 | UAGGUCU C UGGCCUC |
| 1964 | 196 | GAGACAU A GCCCCAC | 2233 | 245 | CUGGCCU C ACGGAGC |
| 1983 | 197 | AGGACAU A CAACUGG | 2242 | 246 | CGGAGCU C CCAGUCC |
| 1996 | 198 | GGGAAAU A CUGAAAC | 2248 | 247 | UCCCAGU C CAUGUCA |
| 2005 | 199 | UGAAACU U GCUGCCU | 2254 | 248 | UCCAUGU C ACAUUCA |
| 2013 | 200 | GCUGCCU A UUGGGUA | 2259 | 249 | GUCACAU U CAAGGUC |
| 2015 | 201 | UGCCUAU U GGGUAUG | 2260 | 250 | UCACAUU C AAGGUCA |
| 2020 | 202 | AUUGGGU A UGCUGAG | 2266 | 251 | UCAAGGU C ACCAGGU |
| 2039 | 203 | ACAGACU U ACAGAAG | 2274 | 252 | ACCAGGU A CAGUUGU |
| 2040 | 204 | CAGACUU A CAGAAGA | 2279 | 253 | GUACAGU U GUACAGG |
| 2057 | 205 | UGGCCCU C CAUAGAC | 2282 | 254 | CAGUUGU A CAGGUUG |
| 2061 | 206 | CCUCCAU A GACAUGU | 2288 | 255 | UACAGGU U GUACACU |
| 2071 | 207 | CAUGUGU A GCAUCAA | 2291 | 256 | AGGUUGU A CACUGCA |
| 2076 | 208 | GUAGCAU C AAAACAC | 2321 | 257 | AAAAGAU C AAAUGGG |
| 2097 | 209 | CCACACU U CCUGACG | 2338 | 258 | UGGGACU U CUCAUUG |
| 2098 | 210 | CACACUU C CUGACGG | 2339 | 259 | GGGACUU C UCAUUGG |
| 2115 | 211 | GCCAGCU U GGGCACU | 2341 | 260 | GACUUCU C AUUGGCC |
| 2128 | 212 | CUGCUGU C UACUGAC | 2344 | 261 | UUCUCAU U GGCCAAC |
| 2130 | 213 | GCUGUCU A CUGACCC | 2358 | 262 | CCUGCCU U UCCCCAG |
| 2145 | 214 | CAACCCU U GAUGAUA | 2359 | 263 | CUGCCUU U CCCCAGA |
| 2152 | 215 | UGAUGAU A UGUAUUU | 2360 | 264 | UGCCUUU C CCCAGAA |
| 2156 | 216 | GAUAUGU A UUUAUUC | 2376 | 265 | GAGUGAU U UUUCUAU |
| 2158 | 217 | UAUGUAU U UAUUCAU | 2377 | 266 | AGUGAUU U UUCUAUC |
| 2159 | 218 | AUGUAUU U AUUCAUU | 2378 | 267 | GUGAUUU U UCUAUCG |
| 2160 | 219 | UGUAUUU A UUCAUUU | 2379 | 268 | UGAUUUU U CUAUCGG |
| 2162 | 220 | UAUUUAU U CAUUUGU | 2380 | 269 | GAUUUUU C UAUCGGC |
| 2163 | 221 | AUUUAUU C AUUUGUU | 2382 | 270 | UUUUUCU A UCGGCAC |
| 2166 | 222 | UAUUCAU U UGUUAUU | 2384 | 271 | UUUCUAU C GGCACAA |
| 2167 | 223 | AUUCAUU U GUUAUUU | 2399 | 272 | AAGCACU A UAUGGAC |
| 2170 | 224 | CAUUUGU U AUUUAC | 2401 | 273 | GCACUAU A UGGACUG |
| 2171 | 225 | AUUUGUU A UUUACC | 2411 | 274 | GACUGGA A AUGGUUC |
| 2173 | 226 | UUGUUAU U UUACCAG | 2417 | 275 | UAAUGGU U CACAGGU |
| 2174 | 227 | UGUUAUU U UACCAGC | 2418 | 276 | AAUGGUU C ACAGGUU |
| 2175 | 228 | GUUAUUU U ACCAGCU | 2425 | 277 | CACAGGU U CAGAGAU |
| 2176 | 229 | UUAUUUU A CCAGCUA | 2426 | 278 | ACAGGUU C AGAGAUU |
| 2183 | 230 | ACCAGCU A UUUAUUG | 2433 | 279 | CAGAGAU U ACCCAGU |

23

| | | | | | | |
|---|---|---|---|---|---|---|
| 2185 | 231 | CAGCUAU U UAUUGAG | 2434 | 280 | AGAGAUU A CCCAGUG |
| 2186 | 232 | AGCUAUU U AUUGAGU | 2448 | 281 | GAGGCCU U AUUCCUC |
| 2187 | 233 | GCUAUUU A UUGAGUG | 2449 | 282 | AGGCCUU A UUCCUCC |
| 2451 | 283 | GCCUAUU U CCUCCCU | 2750 | 332 | UAUGUGU A GACAAGC |
| 2452 | 284 | CCUUAUU C CUCCCUU | 2759 | 333 | ACAAGCU C UCGCUCU |
| 2455 | 285 | UAUUCCU C CCUUCCC | 2761 | 334 | AAGCUCU C GCUCUGU |
| 2459 | 286 | CCUCCCU U CCCCCCA | 2765 | 335 | UCUCGCU C UGUCACC |
| 2460 | 287 | CUCCCUU C CCCCCAA | 2769 | 336 | GCUCUGU C ACCCAGG |
| 2479 | 288 | GACACCU U UGUUAGC | 2797 | 337 | GUGCAAU C AUGGUUC |
| 2480 | 289 | ACACCUU U GUUAGCC | 2803 | 338 | UCAUGGU U CACUGCA |
| 2483 | 290 | CCUUUGU U AGCCACC | 2804 | 339 | CAUGGUU C ACUGCAG |
| 2484 | 291 | CUUUGUU A GCCACCU | 2813 | 340 | CUGCAGU C UUGACCU |
| 2492 | 292 | GCCACCU C CCCACCC | 2815 | 341 | GCAGUCU U GACCUUU |
| 2504 | 293 | CCCACAU A CAUUUCU | 2821 | 342 | UUGACCU U UGGGCU |
| 2508 | 294 | CAUACAU U UCUGCCA | 2822 | 343 | UGACCUU U GGGCUC |
| 2509 | 295 | AUACAUU U CUGCCAG | 2823 | 344 | GACCUUU U GGGCUCA |
| 2510 | 296 | UACAUUU C UGCCAGU | 2829 | 345 | UUGGGCU C AAGUGAU |
| 2520 | 297 | CCAGUGU U CACAAUG | 2837 | 346 | AAGUGCU C CUCCCAC |
| 2521 | 298 | CAGUGUU C ACAAUGA | 2840 | 347 | UGAUCCU U CCACCUC |
| 2533 | 299 | UGACACU C AGCGGUC | 2847 | 348 | CCCACCU C AGCCUCC |
| 2540 | 300 | CAGCGGU C AUGUCUG | 2853 | 349 | UCAGCCU C CUGAGUA |
| 2545 | 301 | GUCAUGU C UGGACAU | 2860 | 350 | CCUGAGU A GCUGGGA |
| 2568 | 302 | AGGGAAU A UGCCCAA | 2872 | 351 | GGACCAU A GGCUCAC |
| 2579 | 303 | CCAAGCU A UGCCUUG | 2877 | 352 | AUAGGCU C ACAACAC |
| 2585 | 304 | UAUGCCU U GUCCUCU | 2899 | 353 | GGCAAAU U UGAUUUU |
| 2588 | 305 | GCCUUGU C CUCUUGU | 2900 | 354 | GCAAAUU U GAUUUUU |
| 2591 | 306 | UUGUCCU C UUGUCCU | 2904 | 355 | AUUUGAU U UUUUUUU |
| 2593 | 307 | GUCCUCU U GUCCUGU | 2905 | 356 | UUUGAUU U UUUUUUU |
| 2596 | 308 | CUCUUGU C CUGUUUG | 2906 | 357 | UUGAUUU U UUUUUUU |
| 2601 | 309 | GUCCUGU U UGCAUUU | 2907 | 358 | UGAUUUU U UUUUUUU |
| 2602 | 310 | UCCUGUU U GCAUUUC | 2908 | 359 | GAUUUUU U UUUUUUU |
| 2607 | 311 | UUUGCAU U UCACUGG | 2909 | 360 | AUUUUUU U UUUUUUU |
| 2608 | 312 | UUGCAUU U CACUGGG | 2910 | 361 | UUUUUUU U UUUUUUU |
| 2609 | 313 | UGCAUUU C ACUGGGA | 2911 | 362 | UUUUUUU U UUUUUUU |
| 2620 | 314 | GGGAGCU U GCACUAU | 2912 | 363 | UUUUUUU U UUUUUUC |
| 2626 | 315 | UUGCACU A UUGCAGC | 2913 | 364 | UUUUUUU U UUUUUCA |
| 2628 | 316 | GCACUAU U GCAGCUC | 2914 | 365 | UUUUUUU U UUUUCAG |
| 2635 | 317 | UGCAGCU C CAGUUUC | 2915 | 366 | UUUUUUU U UUUCAGA |
| 2640 | 318 | CUCCAGU U UCCUGCA | 2916 | 367 | UUUUUUU U UUCAGAG |
| 2641 | 319 | UCCAGUU U CCUGCAG | 2917 | 368 | UUUUUUU U UCAGAGA |
| 2642 | 320 | CCAGUUU C CUGCAGU | 2918 | 369 | UUUUUUU U CAGAGAC |
| 2653 | 321 | CAGUGAU C AGGGUCC | 2919 | 370 | UUUUUUU C AGAGACG |
| 2659 | 322 | UCAGGGU C CUGCAAG | 2931 | 371 | ACGGGGU C UCGCAAC |
| 2689 | 323 | CCAAGGU A UUGGAGG | 2933 | 372 | GGGGUCU C GCAACAU |
| 2691 | 324 | AAGGUAU U GGAGGAC | 2941 | 373 | GCAACAU U GCCCAGA |
| 2700 | 325 | GAGGACU C CCUCCCA | 2951 | 374 | CCAGACU U CCUUUGU |
| 2704 | 326 | ACUCCCU C CAGCUU | 2952 | 375 | CAGACUU C CUUUGUG |
| 2711 | 327 | CCCAGCU U UGGAAGG | 2955 | 376 | ACUUCCU U UGUGUUA |

24

| | | | | | |
|---|---|---|---|---|---|
| 2712 | 328 | CCAGCUU U GGAAGGG | 2956 | 377 | CUUCCUU U GUGUUAG |
| 2721 | 329 | GAAGGGU C AUCCGCG | 2961 | 378 | UUUGUGU U AGUUAAU |
| 2724 | 330 | GGGUCAU C CGCGUGU | 2962 | 379 | UUGUGUU A GUUAAUA |
| 2744 | 331 | UGUGUGU A UGUGUAG | 2965 | 380 | UGUUAGU U AAUAAAG |
| 2966 | 381 | GUUAGUU A AUAAAGC | | | |
| 2969 | 382 | AGUUAAU A AAGCUUU | | | |
| 2975 | 383 | UAAAGCU U UCUCAAC | | | |
| 2976 | 384 | AAAGCUU U CUCAACU | | | |
| 2977 | 385 | AAGCUUU C UCAACUG | | | |
| 2979 | 386 | GCUUUCU C AACUGCC | | | |

Table III

Mouse ICAM HH Target Sequence

| nt. Position | SEQ ID NO | Target Sequence | nt. Position | SEQ ID NO | Target Sequence |
|---|---|---|---|---|---|
| 11 | 387 | CCCugGU C acCGuUG | 367 | 584 | AAugGCU u cAACCcg |
| 23 | 388 | CaGuGgU u CUCUGCU | 374 | 585 | gAAgCCU U CCUgcCC |
| 26 | 389 | uGgUuCU C UGCUcCU | 375 | 586 | AAgCCUU C CUgcCCc |
| 31 | 390 | CUCUGCU c CUCcaca | 378 | 587 | CuacCaU C ACCGUGU |
| 34 | 391 | UuCUcaU a AGgGUcG | 386 | 588 | ACCGUGU A uUcGuuU |
| 40 | 392 | gCAcAcU U GuAgCCU | 394 | 589 | CcGGACU u ucGAuCu |
| 48 | 393 | aggACCU C AGCCUgG | 420 | 590 | CACaCuU C CCCcCcg |
| 54 | 394 | UggGCCU C GugAUGG | 425 | 591 | CaCCCCU C ccaGCAG |
| 58 | 395 | CaUgcCU u UaGCUCC | 427 | 592 | CagCUCU c aGCAGug |
| 64 | 396 | cAcccCU C CCAGCAG | 450 | 593 | AGgACCU c ACCCUgC |
| 96 | 397 | CucugCU C CUGGcCC | 451 | 594 | GAAaCcU u uCCUuuG |
| 102 | 398 | UgCcaGU a CUGCUgG | 456 | 595 | UUACCCU c aGCcaCu |
| 108 | 399 | cuCUGCU C cuGGCcC | 495 | 596 | CuAcCaU C ACCGUGu |
| 115 | 400 | uGGuuCU C UGcUCCu | 510 | 597 | UGCUGCU C CGUGGGG |
| 119 | 401 | GgaaUGU c aCCAGGA | 564 | 598 | CUcAGGU a uCcAuCc |
| 120 | 402 | CUCUGCU C CugGccC | 592 | 599 | GAaAGAU C ACaugGG |
| 146 | 403 | CAGuCgU C cGcuUCC | 607 | 600 | AGCCAAU U UCUCaUG |
| 152 | 404 | UCUGUGU C agCCaCu | 608 | 601 | GCCAAUU U CUCaUGC |
| 158 | 405 | UCCuguU u AAAAacC | 609 | 602 | CCAAUUU C UcaUGCC |
| 165 | 406 | CAgAAGU u gUuuUGC | 611 | 603 | AAUUUCU C aUGCCGC |
| 168 | 407 | AAGcCuU C CUGCCCC | 656 | 604 | aAGCUGU U UGAGcug |
| 185 | 408 | GGuGGgU C CGUGCaG | 657 | 605 | AGCUGUU U GAGcugA |
| 209 | 409 | gcCACuU C CUcUGgC | 668 | 606 | cgagCCU a GGCCaCC |
| 227 | 410 | CagAAGU U GUUuuGC | 677 | 607 | GaCCuCU A CCAGCCu |
| 230 | 411 | AAGUUGU U uuGCucc | 684 | 608 | uuCAGCU C CgGuCCU |
| 237 | 412 | UGuGCuU u GAGAaCu | 692 | 609 | CgACuCU U cGauCUu |
| 248 | 413 | AaCCCaU c uCCUAAA | 693 | 610 | AGgaCcU c acCCUGC |
| 253 | 414 | ccUGCCU A AggAaGA | 696 | 611 | CCUgUuU C CUGCCuc |
| 263 | 415 | AgGGuuU c uCUaCUG | 709 | 612 | gGCGgCU C CaCCuCA |
| 267 | 416 | AGggGCU C CUGCCUa | 720 | 613 | uACAACU U uUCAGCu |
| 293 | 417 | AAGcCUGU u UGAgCUG | 723 | 614 | AACUUuU C AGCuCCg |
| 319 | 418 | AGgAGAU A cugAgCC | 735 | 615 | aCCaGaU C CUgGAGa |
| 335 | 419 | cUGUGCU u UgagAAC | 738 | 616 | uGGgCCU c GuGaUGG |
| 337 | 420 | GUcCaAU U CAcACUG | 765 | 617 | CaGUcGU C cGcUuCC |

26

| 338 | 421 | aGCUgUU u gAgCUGa | 769 | 618 | GGcCUGU U uCCUGcc |
|---|---|---|---|---|---|
| 359 | 422 | GuGCAGU C guCcGCU | 770 | 619 | uUuUGcU C CCUGGAa |
| 785 | 423 | GGcCUGU U uCCuGcC | 1353 | 620 | AGUGggU c gAaGgUG |
| 786 | 424 | GcCUGUU u CCuGcCU | 1366 | 621 | UaaCAgU c UaCaACU |
| 792 | 425 | UggagGU C UCGGAaG | 1367 | 622 | aGCACcU c CCCACcu |
| 794 | 426 | CugGgCU u GGAGaCu | 1368 | 623 | GuACUgU a CCACUcu |
| 807 | 427 | CuCgGaU a uACCUGG | 1380 | 624 | UGCCCAU C GGGUgg |
| 833 | 428 | CAaAGcU c GAcaCCC | 1388 | 625 | GGaGAcU C AGUGgCU |
| 846 | 429 | CCcugGU C ACCguUG | 1398 | 626 | UGgCUGU C ACagaAc |
| 851 | 430 | GagACCU U UacCAgC | 1402 | 627 | UGUgcuU u GAGAaCU |
| 863 | 431 | AgCcACU U CcUCUgG | 1408 | 628 | gCGAGAU C gggGgaGG |
| 866 | 432 | GAagCCU U CcuGcCC | 1410 | 629 | GAGgUCU c GgaaGgg |
| 867 | 433 | AuUCgUU u cCGGagA | 1421 | 630 | ccCACCU A CUuuUGU |
| 869 | 434 | UCuUcCU C augCAAG | 1425 | 631 | aCUgCCU u gGUaGaG |
| 881 | 435 | AuGGCuU C AacCcGU | 1429 | 632 | uCUCUaU u GccCCuG |
| 885 | 436 | CCUugGU a gagGUGA | 1444 | 633 | GAaggCU C AgGaGGA |
| 933 | 437 | cUauAaU c AUuCUGG | 1455 | 634 | GGaAuGU C ACCaGga |
| 936 | 438 | uAaUcAU u CUGGuGc | 1482 | 635 | AguUGUU u UgCuCCC |
| 978 | 439 | UaACagU C UACAaCU | 1484 | 636 | cUGuUCU u CCuCauG |
| 980 | 440 | ACagUCU A CAaCUUU | 1493 | 637 | CugUGcU u UGAGAac |
| 986 | 441 | UACAaCU U UuCaGCu | 1500 | 638 | AUGAaAU c aUggUCc |
| 987 | 442 | ACAaCUU U uCaGCuC | 1503 | 639 | gGAcUaU a AUCAUuc |
| 988 | 443 | CAaCUUU u CaGCuCC | 1506 | 640 | UUaUguU u AUaACCG |
| 1005 | 444 | ACcaGAU c CUGgaGA | 1509 | 641 | cuAcCAU C ACcGUGu |
| 1006 | 445 | uGaGAgU C UGggGAA | 1518 | 642 | ucaUGGU c cCAGgCG |
| 1023 | 446 | ugGAGGU U UCgGAAG | 1530 | 643 | CuauAaU C AUucUGG |
| 1025 | 447 | GAGGUCU C gGAAGGG | 1533 | 644 | ugGUCAU u gUGGGCc |
| 1066 | 448 | CCACuCU c aAaauAA | 1551 | 645 | CAuGCCU u AGCAgcU |
| 1092 | 449 | AcuGGaU u uCAGgCC | 1559 | 646 | AGCACcU c CCcaccU |
| 1093 | 450 | UGGaccU u CAGCCaA | 1563 | 647 | CuUAugU u UAUAACC |
| 1125 | 451 | CCCAaCU C uUcuUGA | 1565 | 648 | UAugUuU A UAACCGC |
| 1163 | 452 | CGaAGCU U CUuuUGC | 1567 | 649 | ugUuUAU A ACCGCCA |
| 1164 | 453 | GaAGCUU C UuuUGCU | 1584 | 650 | GaAAGAU C AgGAuAU |
| 1166 | 454 | AGCUUCU u uUGCUCU | 1592 | 651 | AgGAuAU A CAaguUA |
| 1172 | 455 | UCCUGuU u aaaAACC | 1599 | 652 | ACAaguU A CAgaAGG |
| 1200 | 456 | cuCuGCU c cUcCACA | 1651 | 653 | CcCaCCU C CCUGAgC |
| 1201 | 457 | gCuGCUU u UgaACAg | 1661 | 654 | gaAACCU u UCCUuuG |
| 1203 | 458 | AcuUUuU u CACcAGu | 1663 | 655 | AACCUuU C CuuuGAa |
| 1227 | 459 | GGuAcaU a CGUGUgC | 1678 | 656 | AGGaCCU C agCCUgG |
| 1228 | 460 | GaAGCUU c uUuUgCU | 1680 | 657 | aGCCaCU U CCUcUGg |
| 1233 | 461 | UUCGUuU C CgGagaG | 1681 | 658 | GCCaCUU C CUCUgGC |
| 1238 | 462 | GUgCUGU A UGGuCCu | 1684 | 659 | aCUUCCU C uGgCUgu |
| 1264 | 463 | GAaGGgU C GUgCaaG | 1690 | 660 | cCGGaCU U uCgAUcU |
| 1267 | 464 | uGAgaGU U uGGGgAA | 1691 | 661 | CGGaCUU u CgAUcUU |
| 1294 | 465 | AGgAgAU a CugAGCc | 1696 | 662 | UgCCCAU c ggGGUGG |
| 1295 | 466 | GAggggU C uCAGCAG | 1698 | 663 | CggAUAU a ccUGGag |
| 1306 | 467 | GCAGACU C ugAaaUG | 1737 | 664 | gAGACcU c UaCCAgc |
| 1321 | 468 | gaAGGCU c aGGaGgA | 1750 | 665 | gGCgGCU c CACCUca |

| | | | | | |
|---|---|---|---|---|---|
| 1334 | 469 | AACCCAU c uCCuaAa | 1756 | 666 | gAagCCU u CCuGCCC |
| 1344 | 470 | auGAGCU C gAGaGUg | 1787 | 667 | gaGaCAU U GUCCcCA |
| 1351 | 471 | ugAaUGU a UAAguuA | 1790 | 668 | GCAUUGU u CUCuaau |
| 1793 | 472 | UgGUCCU C gGcugGA | 2173 | 669 | UUagagU U UUACCAG |
| 1797 | 473 | CacCAGU C AcAUAaA | 2174 | 670 | UagagUU U UACCAGC |
| 1802 | 474 | acCAGAU c CuggAGa | 2175 | 671 | agagUUU U ACCAGCU |
| 1812 | 475 | ACuGgAU c UcaGGCC | 2176 | 672 | gagUUUU A CCAGCUA |
| 1813 | 476 | CAGCAUU U acccuCA | 2183 | 673 | ACCAGCU A UUUAUUG |
| 1825 | 477 | CCAcGcU A CCUcugC | 2185 | 674 | CAGCUAU U UAUUGAG |
| 1837 | 478 | CAugCCU u uAgCuCc | 2186 | 675 | AGCUAUU U AUUGAGU |
| 1845 | 479 | cgAgcCU A GGCCACc | 2187 | 676 | GCUAUUU A UUGAGUa |
| 1856 | 480 | CggaCuU u cGAUCUu | 2189 | 677 | UAUUUAU U GAGUacC |
| 1861 | 481 | AcaUGAU a UccAGUa | 2196 | 678 | caAcUcU u cUUgAUG |
| 1865 | 482 | cAcuUGU A GcCuCAg | 2198 | 679 | gcaGcCU c UUAUGUu |
| 1868 | 483 | CaccAGU C ACAUaAa | 2199 | 680 | GccUCUU a UgUuUAu |
| 1877 | 484 | CAUGcCU u AGCagcu | 2200 | 681 | UcUuccU c AUGcAaG |
| 1901 | 485 | uAAaACU C AAGggAc | 2201 | 682 | aagUUUU A UGUcGGC |
| 1912 | 486 | AuAUagU a GAUcagU | 2205 | 683 | UUUAUGU c GGCcugA |
| 1922 | 487 | UGaAUGU a uAAGUua | 2210 | 684 | GgAGaCU c AgUGgcu |
| 1923 | 488 | uGAUGCU c AgGUaUc | 2220 | 685 | cuggCAU u GuUCUCU |
| 1928 | 489 | UUAgAGU u UuaCCaG | 2224 | 686 | CucAGGU a UCcauCC |
| 1930 | 490 | AgAGUuU u aCCaGcU | 2226 | 687 | UgGaUCU C aGGCCgC |
| 1964 | 491 | GAGACAU u GuCCCca | 2233 | 688 | CUGaCCU C cuGGAGg |
| 1983 | 492 | AGGAuAU A CAAgUua | 2242 | 689 | uGGAGCU a gCgGaCC |
| 1996 | 493 | aGGAgAU A CUGAgcC | 2248 | 690 | UauCcaU C CAUccCA |
| 2005 | 494 | UGgAgCU a GCgGaCc | 2254 | 691 | UCCAauU C ACAcUgA |
| 2013 | 495 | GCUauuU A UUGaGUA | 2259 | 692 | aUCACAU U CAcGGUg |
| 2015 | 496 | UGCCcAU U GGGgugG | 2260 | 693 | UCACAUU C AcGGUgc |
| 2020 | 497 | ggUGGuU U UuCUGAG | 2266 | 694 | ggAAuGU C ACCAGGa |
| 2039 | 498 | gCuGgCU a gCAGAgG | 2274 | 695 | ACCAGaU c CUggaGa |
| 2040 | 499 | CuGACcU C CUggAGg | 2279 | 696 | GaAggGU c GUgCAaG |
| 2057 | 500 | UGcuCCU C CAcAucC | 2282 | 697 | aAGcUGU u ugaGcUG |
| 2061 | 501 | CuaCCAU c acCgUGU | 2288 | 698 | UAuAaGU U aUggcCU |
| 2071 | 502 | CAcuUGU A GCcUCAg | 2291 | 699 | caGUgGU u CuCUGCu |
| 2076 | 503 | GUAGCcU C AgAgCua | 2321 | 700 | gAAAGAU C AcAUGGG |
| 2097 | 504 | CaACuCU U CuUGAuG | 2338 | 701 | UGaGACU c CUGccUG |
| 2098 | 505 | CACACUU C CcccCcG | 2339 | 702 | GaaACCU u UCcUUuG |
| 2115 | 506 | GCCAGCU c GGaggaU | 2341 | 703 | GACcUCU a ccaGcCu |
| 2128 | 507 | CaGCUaU u UAuUGAg | 2344 | 704 | UUucgAU c uuCCAgC |
| 2130 | 508 | cCUGUuU c CUGcCuC | 2358 | 705 | CCcagCU C UCagCAG |
| 2145 | 509 | CAACuCU U cuUGAUg | 2359 | 706 | CUGCuUU U gaaCAGA |
| 2152 | 510 | UauUaAU u UagAgUU | 2360 | 707 | aaCCUUU C CuuuGAA |
| 2156 | 511 | uugAUGU A UUUAUUa | 2376 | 708 | agGUGgU U cUUCUga |
| 2158 | 512 | gAUGUAU U UAUUaAU | 2377 | 709 | gGUGgUU c UUCUgag |
| 2159 | 513 | AUGUAUU U AUUaAUU | 2378 | 710 | agGgUUU c UCUAcUg |
| 2160 | 514 | UGUAUUU A UUaAUUU | 2379 | 711 | UGcUUUU c ucAUaaG |
| 2162 | 515 | UAUUUAU U aAUUUag | 2380 | 712 | aAgUUUU a UgUCGGC |
| 2163 | 516 | AUgUAUU u AUUaaUU | 2382 | 713 | aUUcUCU A UuGcCCC |

| | | | | | |
|---|---|---|---|---|---|
| 2166 | 517 | acUUCAU U cucUAUU | 2384 | 714 | aUcCagU a GaCACAA |
| 2167 | 518 | AUguAUU U aUUAaUU | 2399 | 715 | AAaCACU A UgUGGAC |
| 2170 | 519 | uAUUUaU U AaUUUAg | 2401 | 716 | aagCUgU u UGagCUG |
| 2171 | 520 | AgUUGUU u UgcUcCC | 2411 | 717 | uACUGGU c AgGaUgC |
| 2417 | 521 | gAAUGGU a CAuAcGU | 2691 | 718 | AAuGUcU c cGAGGcC |
| 2418 | 522 | AcUGGaU C uCAGGcc | 2700 | 719 | GAaGCCU u CCUgCCc |
| 2425 | 523 | CAugGGU c gAGgGuU | 2704 | 720 | gacCuCU a CCAGCcU |
| 2426 | 524 | AuuaaUU u AGAGuUU | 2711 | 721 | CCCAGCU c UcagcaG |
| 2433 | 525 | uAGAGuU U uaCCAGc | 2712 | 722 | gagGucU c GGAAGGG |
| 2434 | 526 | AGAGuUU u aCCAGcu | 2721 | 723 | GAAGGGU C gUgCaaG |
| 2448 | 527 | GAaGCCU U ccUgCcC | 2724 | 724 | GGuaCAU a CGuGUGc |
| 2449 | 528 | AaGCCUU c cUgCcCC | 2744 | 725 | gGUGgGU c cGUGCAG |
| 2451 | 529 | GCCUguU U CCUgCCU | 2750 | 726 | UAUuUaU u GAguAcC |
| 2452 | 530 | CCUguUU C CUgCCUc | 2759 | 727 | cCggaCU u UCGaUCU |
| 2455 | 531 | gAagCCU u CCUgCCC | 2761 | 728 | AgGacCU C aCcCUGc |
| 2459 | 532 | CCaCaCU U CCCCCCc | 2765 | 729 | UuUuGCU C UGcCgCu |
| 2460 | 533 | CaCaCUU C CCCCCcg | 2769 | 730 | agUCUGU C AaaCAGG |
| 2479 | 534 | GAgACCU c UaccAGC | 2797 | 731 | aUGaAAU C AUGGUcC |
| 2480 | 535 | uCACCgU U GUgAuCC | 2803 | 732 | UCAUGGU c CcagGCg |
| 2483 | 536 | CCaaUGU c AGCCACC | 2804 | 733 | ggUGGgU C cgUGCAG |
| 2484 | 537 | CUUUuUU c aCCAguc | 2813 | 734 | CUcCgGU C cUGACCc |
| 2492 | 538 | agCACCU C CCCACCu | 2815 | 735 | aCAGUCU a cAaCUUU |
| 2504 | 539 | CCCACcU A CuUUUgU | 2821 | 736 | cUGACCU c cUGGgagg |
| 2508 | 540 | uAUcCAU U caUcCCA | 2822 | 737 | gGAgCCU c cGGaCUu |
| 2509 | 541 | uUAgAgU U uUaCCAG | 2823 | 738 | ugCCUUU a GcuCcCA |
| 2510 | 542 | UAgAgUU u UaCCAGc | 2829 | 739 | cUGGaCU a uAaUcAU |
| 2520 | 543 | CuuuUGU U CcCAAUG | 2837 | 740 | AgGUGgU u CUuCuga |
| 2521 | 544 | CAGcaUU u ACccUcA | 2840 | 741 | UGAgaCU C CugCCUg |
| 2533 | 545 | UGAugCU C AGguaUC | 2847 | 742 | CCaAugU C AGCCaCC |
| 2540 | 546 | CAGCaGU C cgcUgUG | 2853 | 743 | gCAGCCU c uUuauGUu |
| 2545 | 547 | GUgcUGU a UGGuCcU | 2860 | 744 | gCcaAGU A aCUGuGA |
| 2568 | 548 | guGaAgU c UGuCaAA | 2872 | 745 | GGACCUu c aGCcaAg |
| 2579 | 549 | auAAGuU A UGgCcUG | 2877 | 746 | uUccGCU a cCAuCAC |
| 2585 | 550 | cugGCaU U GUuCUCU | 2899 | 747 | cGgAcUU U cGAUcUU |
| 2588 | 551 | GCaUUGU u CUCUaaU | 2900 | 748 | uuAAuUU a GAgUUUU |
| 2591 | 552 | UgGUuCU C UgcUCCU | 2904 | 749 | AcUUcAU U cUcUaUU |
| 2593 | 553 | cUuCUuU U GcuCUGc | 2905 | 750 | cUUcAUU c UcUaUUg |
| 2596 | 554 | CUuUUGU u CcccaaUG | 2906 | 751 | UUGAUgU a UUUaUUa |
| 2601 | 555 | acCgUGU a UuCgUUU | 2907 | 752 | UGuaUUU a UUaaUUU |
| 2602 | 556 | UCCagCU c cCAUccC | 2908 | 753 | GAagCUU c UUUUgcU |
| 2607 | 557 | cUcGgAU a UacCUGG | 2909 | 754 | AgcUUcU U UUgcUcU |
| 2608 | 558 | caGCAgU c CgCUGuG | 2910 | 755 | UgUaUUU a UUaaUUU |
| 2609 | 559 | gGaAUgU C ACcaGGA | 2911 | 756 | UgUaUUU a UUaaUUU |
| 2620 | 560 | aGGAcCU c aCcCUGc | 2912 | 757 | UUgUUcU c UaaUgUC |
| 2626 | 561 | UUuCgaU c UUcCAGC | 2913 | 758 | UUUcUcU a cUggUCA |
| 2628 | 562 | GCACacU U GuAGCcu | 2914 | 759 | UgcUUUU c UcaUaAG |
| 2635 | 563 | UuCAGCU C CgGUccu | 2915 | 760 | aUUUaUU a aUUuAGA |
| 2640 | 564 | ggCCuGU U UCCUGCc | 2916 | 761 | UaUUcgU U UcCgGAG |

29

| 2641 | 565 | cCCAGcU c uCaGCAG | 2917 | 762 | aUUcgUU U cCgGAGA |
| 2642 | 566 | CCuGUUU C CUGCcuc | 2918 | 763 | UUcgUUU c CgGAGAg |
| 2653 | 567 | uAcUGgU C AGGaUgC | 2919 | 764 | UUcUcaU a AGgGuCG |
| 2659 | 568 | gaAGGGU C gUGCAAG | 2931 | 765 | ugGaGGU C UCGgAAg |
| 2689 | 569 | CuAAuGU c UccGAGG | 2933 | 766 | GaGGUCU C GgAAggg |

30

| | | |
|---|---|---|
| 2941 | 570 | GagACAU U GuCCccA |
| 2951 | 571 | CCAcgCU a CCUcUGc |
| 2952 | 572 | CAGcagU C CgcUGUG |
| 2955 | 573 | AgUgaCU c UGUGUcA |
| 2956 | 574 | uUUCCUU U GaaUcAa |
| 2961 | 575 | UcUGUGU c AGccAcU |
| 2962 | 576 | aUGUaUU u aUUAAUu |
| 2965 | 577 | UuUgAaU c AAUAAAG |
| 2966 | 578 | GcUgGcU A gcAgAGg |
| 2969 | 579 | AaUcAAU A AAGuUUU |
| 2975 | 580 | UAgAGuU U UacCAgC |
| 2976 | 581 | gAgGgUU U CUCuACU |
| 2977 | 582 | AAGCUgU u UgAgCUG |
| 2979 | 583 | uCaUUCU C uAuUGCC |

Table IV
Human ICAM HH Ribozyme Sequences

| nt. Position | SEQ ID NO | Ribozyme Sequence |
|---|---|---|
| 11 | 767 | CAGCGUC CUGAUGAGGCCGAAAGGCCGAA ACUGGGG |
| 23 | 768 | AGCAGAG CUGAUGAGGCCGAAAGGCCGAA AGCUCAG |
| 26 | 769 | AGUAGCA CUGAUGAGGCCGAAAGGCCGAA AGGAGCU |
| 31 | 770 | CUCUGAG CUGAUGAGGCCGAAAGGCCGAA AGCAGAG |
| 34 | 771 | CAACUCU CUGAUGAGGCCGAAAGGCCGAA AGUAGCA |
| 40 | 772 | AGGUUGC CUGAUGAGGCCGAAAGGCCGAA ACUCUGA |
| 48 | 773 | CGAGGCU CUGAUGAGGCCGAAAGGCCGAA AGGUUGC |
| 54 | 774 | CCAUAGC CUGAUGAGGCCGAAAGGCCGAA AGGCUGA |
| 58 | 775 | GGAGCCA CUGAUGAGGCCGAAAGGCCGAA AGCGAGG |
| 64 | 776 | CUGCUGG CUGAUGAGGCCGAAAGGCCGAA AGCCAUA |
| 96 | 777 | GGACCAG CUGAUGAGGCCGAAAGGCCGAA AGUGCGG |
| 102 | 778 | CGAGCAG CUGAUGAGGCCGAAAGGCCGAA ACCAGGA |
| 108 | 779 | GAGCCCC CUGAUGAGGCCGAAAGGCCGAA AGCAGGA |
| 115 | 780 | GGGAACA CUGAUGAGGCCGAAAGGCCGAA AGCCCCG |
| 119 | 781 | UCCUGGG CUGAUGAGGCCGAAAGGCCGAA ACAGAGC |
| 120 | 782 | GUCCUGG CUGAUGAGGCCGAAAGGCCGAA AACAGAG |
| 146 | 783 | GGACACA CUGAUGAGGCCGAAAGGCCGAA AUGUCUG |
| 152 | 784 | UGAGGGG CUGAUGAGGCCGAAAGGCCGAA ACACAGA |
| 158 | 785 | GACUUUU CUGAUGAGGCCGAAAGGCCGAA AGGGGGA |
| 165 | 786 | GCAGGAU CUGAUGAGGCCGAAAGGCCGAA ACUUUUG |
| 168 | 787 | GGGGCAG CUGAUGAGGCCGAAAGGCCGAA AUGACUU |
| 185 | 788 | CAGCACG CUGAUGAGGCCGAAAGGCCGAA AGCCUCC |
| 209 | 789 | GUCACAG CUGAUGAGGCCGAAAGGCCGAA AGGUGCU |
| 227 | 790 | GCCCAAC CUGAUGAGGCCGAAAGGCCGAA ACUUGGG |
| 230 | 791 | UAUGCCC CUGAUGAGGCCGAAAGGCCGAA ACAACUU |
| 237 | 792 | GGGUCUC CUGAUGAGGCCGAAAGGCCGAA AUGCCCA |
| 248 | 793 | UUUAGGC CUGAUGAGGCCGAAAGGCCGAA ACGGGGU |
| 253 | 794 | UCCUUUU CUGAUGAGGCCGAAAGGCCGAA AGGCAAC |
| 263 | 795 | CAGGAGC CUGAUGAGGCCGAAAGGCCGAA ACUCCUU |
| 267 | 796 | CAGGCAG CUGAUGAGGCCGAAAGGCCGAA AGCAACU |
| 293 | 797 | CAGUUCA CUGAUGAGGCCGAAAGGCCGAA ACACCUU |
| 319 | 798 | GGUUGGC CUGAUGAGGCCGAAAGGCCGAA AUCUUCU |
| 335 | 799 | GUUUGAA CUGAUGAGGCCGAAAGGCCGAA AGCACAU |
| 337 | 800 | CAGUUUG CUGAUGAGGCCGAAAGGCCGAA AUAGCAC |
| 338 | 801 | GCAGUUU CUGAUGAGGCCGAAAGGCCGAA AAUAGCA |
| 359 | 802 | AGCUGUU CUGAUGAGGCCGAAAGGCCGAA ACUGCCC |
| 367 | 803 | AAGGUUU CUGAUGAGGCCGAAAGGCCGAA AGCUGUU |
| 374 | 804 | GGUGAGG CUGAUGAGGCCGAAAGGCCGAA AGGUUUU |
| 375 | 805 | CGGUGAG CUGAUGAGGCCGAAAGGCCGAA AAGGUUU |
| 378 | 806 | ACACGGU CUGAUGAGGCCGAAAGGCCGAA AGGAAGG |

31

| | | |
|---|---|---|
| 386 | 807 | AGUCCAG CUGAUGAGGCCGAAAGGCCGAA ACACGGU |
| 394 | 808 | CGUUCUG CUGAUGAGGCCGAAAGGCCGAA AGUCCAG |
| 420 | 809 | AAGAGGG CUGAUGAGGCCGAAAGGCCGAA AGGGGUG |
| 425 | 810 | CUGCCAA CUGAUGAGGCCGAAAGGCCGAA AGGGGAG |
| 427 | 811 | GGCUGCC CUGAUGAGGCCGAAAGGCCGAA AGAGGGG |
| 450 | 812 | GUAGGGU CUGAUGAGGCCGAAAGGCCGAA AGGUUCU |
| 451 | 813 | CGUAGGG CUGAUGAGGCCGAAAGGCCGAA AAGGUUC |
| 456 | 814 | GGCAGCG CUGAUGAGGCCGAAAGGCCGAA AGGGUAA |
| 495 | 815 | CCACGGU CUGAUGAGGCCGAAAGGCCGAA AGGUUGG |
| 510 | 816 | CCCCACG CUGAUGAGGCCGAAAGGCCGAA AGCAGCA |
| 564 | 817 | UGGUCGU CUGAUGAGGCCGAAAGGCCGAA ACCUCAG |
| 592 | 818 | CCAUGGU CUGAUGAGGCCGAAAGGCCGAA AUCUCUC |
| 607 | 819 | CACGAGA CUGAUGAGGCCGAAAGGCCGAA AUUGGCU |
| 608 | 820 | GCACGAG CUGAUGAGGCCGAAAGGCCGAA AAUUGGC |
| 609 | 821 | GGCACGA CUGAUGAGGCCGAAAGGCCGAA AAAUUGG |
| 611 | 822 | GCGGCAC CUGAUGAGGCCGAAAGGCCGAA AGAAAUU |
| 656 | 823 | GUUCUCA CUGAUGAGGCCGAAAGGCCGAA ACAGCUC |
| 657 | 824 | UGUUCUC CUGAUGAGGCCGAAAGGCCGAA AACAGCU |
| 668 | 825 | GGGGGCC CUGAUGAGGCCGAAAGGCCGAA AGGUGUU |
| 677 | 826 | GAGCUGG CUGAUGAGGCCGAAAGGCCGAA AGGGGGC |
| 684 | 827 | AGGUCUG CUGAUGAGGCCGAAAGGCCGAA AGCUGGU |
| 692 | 828 | CAGGACA CUGAUGAGGCCGAAAGGCCGAA AGGUCUG |
| 693 | 829 | GCAGGAC CUGAUGAGGCCGAAAGGCCGAA AAGGUCU |
| 696 | 830 | CUGGCAG CUGAUGAGGCCGAAAGGCCGAA ACAAAGG |
| 709 | 831 | UGUGGGG CUGAUGAGGCCGAAAGGCCGAA AGUCGCU |
| 720 | 832 | GGCUGAC CUGAUGAGGCCGAAAGGCCGAA AGUUGUG |
| 723 | 833 | GGGGGCU CUGAUGAGGCCGAAAGGCCGAA ACAAGUU |
| 735 | 834 | CCUCUAG CUGAUGAGGCCGAAAGGCCGAA ACCCGGG |
| 738 | 835 | CCACCUC CUGAUGAGGCCGAAAGGCCGAA AGGACCC |
| 765 | 836 | GGGAACA CUGAUGAGGCCGAAAGGCCGAA ACCACGG |
| 769 | 837 | UCCAGGG CUGAUGAGGCCGAAAGGCCGAA ACAGACC |
| 770 | 838 | GUCCAGG CUGAUGAGGCCGAAAGGCCGAA AACAGAC |
| 785 | 839 | GACUGGG CUGAUGAGGCCGAAAGGCCGAA ACAGCCC |
| 786 | 840 | AGACUGG CUGAUGAGGCCGAAAGGCCGAA AACAGCC |
| 792 | 841 | CCUCCGA CUGAUGAGGCCGAAAGGCCGAA ACUGGGA |
| 794 | 842 | GGCCUCC CUGAUGAGGCCGAAAGGCCGAA AGACUGG |
| 807 | 843 | CCAGGUG CUGAUGAGGCCGAAAGGCCGAA ACCUGGG |
| 833 | 844 | GGGGUUC CUGAUGAGGCCGAAAGGCCGAA ACCUCUG |
| 846 | 845 | CAUAGGU CUGAUGAGGCCGAAAGGCCGAA ACUGUGG |
| 851 | 846 | GUUGCCA CUGAUGAGGCCGAAAGGCCGAA AGGUGAC |
| 863 | 847 | CGAGAAG CUGAUGAGGCCGAAAGGCCGAA AGUCGUU |
| 866 | 848 | GGCCGAG CUGAUGAGGCCGAAAGGCCGAA AGGAGUC |
| 867 | 849 | UGGCCGA CUGAUGAGGCCGAAAGGCCGAA AAGGAGU |
| 869 | 850 | CUUGGCC CUGAUGAGGCCGAAAGGCCGAA AGAAGGA |
| 881 | 851 | ACUGACU CUGAUGAGGCCGAAAGGCCGAA AGGCCUU |
| 885 | 852 | UCACACU CUGAUGAGGCCGAAAGGCCGAA ACUGAGG |
| 933 | 853 | CCAGUAU CUGAUGAGGCCGAAAGGCCGAA ACUGCAC |
| 936 | 854 | UCCCCAG CUGAUGAGGCCGAAAGGCCGAA AUUACUG |

32

| | | |
|---|---|---|
| 978 | 855 | AGCUGUA CUGAUGAGGCCGAAAGGCCGAA AUGGUCA |
| 980 | 856 | AAAGCUG CUGAUGAGGCCGAAAGGCCGAA AGAUGGU |
| 986 | 857 | CGCCGGA CUGAUGAGGCCGAAAGGCCGAA AGCUGUA |
| 987 | 858 | GCGCCGG CUGAUGAGGCCGAAAGGCCGAA AAGCUGU |
| 988 | 859 | GGCGCCG CUGAUGAGGCCGAAAGGCCGAA AAAGCUG |
| 1005 | 860 | UCGUCAG CUGAUGAGGCCGAAAGGCCGAA AUCACGU |
| 1006 | 861 | UUCGUCA CUGAUGAGGCCGAAAGGCCGAA AAUCACG |
| 1023 | 862 | CUUCUGA CUGAUGAGGCCGAAAGGCCGAA ACCUCUG |
| 1025 | 863 | CCCUUCU CUGAUGAGGCCGAAAGGCCGAA AGACCUC |
| 1066 | 864 | UUGGCUC CUGAUGAGGCCGAAAGGCCGAA AGGGUGG |
| 1092 | 865 | GGGCUGG CUGAUGAGGCCGAAAGGCCGAA ACCCCAU |
| 1093 | 866 | UGGGCUG CUGAUGAGGCCGAAAGGCCGAA AACCCCA |
| 1125 | 867 | UCAGCAG CUGAUGAGGCCGAAAGGCCGAA AGCUGGG |
| 1163 | 868 | GCAGGAG CUGAUGAGGCCGAAAGGCCGAA AGCUGCG |
| 1164 | 869 | AGCAGGA CUGAUGAGGCCGAAAGGCCGAA AAGCUGC |
| 1166 | 870 | AGAGCAG CUGAUGAGGCCGAAAGGCCGAA AGAAGCU |
| 1172 | 871 | GGUUGCA CUGAUGAGGCCGAAAGGCCGAA AGCAGGA |
| 1200 | 872 | UGUGUAU CUGAUGAGGCCGAAAGGCCGAA AGCUGGC |
| 1201 | 873 | UUGUGUA CUGAUGAGGCCGAAAGGCCGAA AAGCUGG |
| 1203 | 874 | UCUUGUG CUGAUGAGGCCGAAAGGCCGAA AUAAGCU |
| 1227 | 875 | GGACACG CUGAUGAGGCCGAAAGGCCGAA AGCUCCC |
| 1228 | 876 | AGGACAC CUGAUGAGGCCGAAAGGCCGAA AAGCUCC |
| 1233 | 877 | CAUACAG CUGAUGAGGCCGAAAGGCCGAA ACACGAA |
| 1238 | 878 | GGGGCCA CUGAUGAGGCCGAAAGGCCGAA ACAGGAC |
| 1264 | 879 | CCCGGAC CUGAUGAGGCCGAAAGGCCGAA AUCCCUC |
| 1267 | 880 | UUUCCCG CUGAUGAGGCCGAAAGGCCGAA ACAAUCC |
| 1294 | 881 | UGCUGGG CUGAUGAGGCCGAAAGGCCGAA AUUUUCU |
| 1295 | 882 | CUGCUGG CUGAUGAGGCCGAAAGGCCGAA AAUUUUC |
| 1306 | 883 | CACAUUG CUGAUGAGGCCGAAAGGCCGAA AGUCUGC |
| 1321 | 884 | UUCCCCC CUGAUGAGGCCGAAAGGCCGAA AGCCUGG |
| 1334 | 885 | CUCGGGC CUGAUGAGGCCGAAAGGCCGAA AUGGGUU |
| 1344 | 886 | GACACUU CUGAUGAGGCCGAAAGGCCGAA AGCUCGG |
| 1351 | 887 | UCCUUUA CUGAUGAGGCCGAAAGGCCGAA ACACUUG |
| 1353 | 888 | CAUCCUU CUGAUGAGGCCGAAAGGCCGAA AGACACU |
| 1366 | 889 | AGUGGGA CUGAUGAGGCCGAAAGGCCGAA AGUGCCA |
| 1367 | 890 | CAGUGGG CUGAUGAGGCCGAAAGGCCGAA AAGUGCC |
| 1368 | 891 | GCAGUGG CUGAUGAGGCCGAAAGGCCGAA AAAGUGC |
| 1380 | 892 | AUUCCCC CUGAUGAGGCCGAAAGGCCGAA AUGGGCA |
| 1388 | 893 | AGUCACU CUGAUGAGGCCGAAAGGCCGAA AUUCCCC |
| 1398 | 894 | CUCGAGU CUGAUGAGGCCGAAAGGCCGAA ACAGUCA |
| 1402 | 895 | AGAUCUC CUGAUGAGGCCGAAAGGCCGAA AGUGACA |
| 1408 | 896 | CCCUCAA CUGAUGAGGCCGAAAGGCCGAA AUCUCGA |
| 1410 | 897 | UGCCCUC CUGAUGAGGCCGAAAGGCCGAA AGAUCUC |
| 1421 | 898 | ACAGAGG CUGAUGAGGCCGAAAGGCCGAA AGGUGCC |
| 1425 | 899 | CCCGACA CUGAUGAGGCCGAAAGGCCGAA AGGUAGG |
| 1429 | 900 | CUGGCCC CUGAUGAGGCCGAAAGGCCGAA ACAGAGG |
| 1444 | 901 | UCCCCUU CUGAUGAGGCCGAAAGGCCGAA AGUGCUC |
| 1455 | 902 | CGCGGGU CUGAUGAGGCCGAAAGGCCGAA ACCUCCC |

| 1482 | 903 | GGGGGGA CUGAUGAGGCCGAAAGGCCGAA AGCACAU |
|------|-----|----------------------------------------|
| 1484 | 904 | CCGGGGG CUGAUGAGGCCGAAAGGCCGAA AGAGCAC |
| 1493 | 905 | AAUCUCA CUGAUGAGGCCGAAAGGCCGAA ACCGGGG |
| 1500 | 906 | UGAUGAC CUGAUGAGGCCGAAAGGCCGAA AUCUCAU |
| 1503 | 907 | UGAUGAU CUGAUGAGGCCGAAAGGCCGAA ACAAUCU |
| 1506 | 908 | CAGUGAU CUGAUGAGGCCGAAAGGCCGAA AUGACAA |
| 1509 | 909 | CCACAGU CUGAUGAGGCCGAAAGGCCGAA AUGAUGA |
| 1518 | 910 | CGGCUGC CUGAUGAGGCCGAAAGGCCGAA ACCACAG |
| 1530 | 911 | CCAUUAU CUGAUGAGGCCGAAAGGCCGAA ACUGCGG |
| 1533 | 912 | UGCCCAU CUGAUGAGGCCGAAAGGCCGAA AUGACUG |
| 1551 | 913 | ACGUGCU CUGAUGAGGCCGAAAGGCCGAA AGGCCUG |
| 1559 | 914 | AUAGAGG CUGAUGAGGCCGAAAGGCCGAA ACGUGCU |
| 1563 | 915 | GGUUAUA CUGAUGAGGCCGAAAGGCCGAA AGGUACG |
| 1565 | 916 | GCGGUUA CUGAUGAGGCCGAAAGGCCGAA AGAGGUA |
| 1567 | 917 | UGGCGGU CUGAUGAGGCCGAAAGGCCGAA AUAGAGG |
| 1584 | 918 | AUUUCUU CUGAUGAGGCCGAAAGGCCGAA AUCUUCC |
| 1592 | 919 | UAGUCUG CUGAUGAGGCCGAAAGGCCGAA AUUUCUU |
| 1599 | 920 | CCUGUUG CUGAUGAGGCCGAAAGGCCGAA AGUCUGU |
| 1651 | 921 | GUUCAGG CUGAUGAGGCCGAAAGGCCGAA AGGCGUG |
| 1661 | 922 | CCCGGGA CUGAUGAGGCCGAAAGGCCGAA AGGUUCA |
| 1663 | 923 | GUCCGG CUGAUGAGGCCGAAAGGCCGAA AUAGGUU |
| 1678 | 924 | CGAGGAA CUGAUGAGGCCGAAAGGCCGAA AGGCCCU |
| 1680 | 925 | GCCGAGG CUGAUGAGGCCGAAAGGCCGAA AGAGGCC |
| 1681 | 926 | GGCCGAG CUGAUGAGGCCGAAAGGCCGAA AAGAGGC |
| 1684 | 927 | GAAGGCC CUGAUGAGGCCGAAAGGCCGAA AGGAAGA |
| 1690 | 928 | AUAUGGG CUGAUGAGGCCGAAAGGCCGAA AGGCCGA |
| 1691 | 929 | AAUAUGG CUGAUGAGGCCGAAAGGCCGAA AAGGCCG |
| 1696 | 930 | CCACCAA CUGAUGAGGCCGAAAGGCCGAA AUGGGAA |
| 1698 | 931 | UGCCACC CUGAUGAGGCCGAAAGGCCGAA AUAUGGG |
| 1737 | 932 | CAUGGCA CUGAUGAGGCCGAAAGGCCGAA AUGUCUU |
| 1750 | 933 | GUAGGUG CUGAUGAGGCCGAAAGGCCGAA AGCUGCA |
| 1756 | 934 | GGGCCGG CUGAUGAGGCCGAAAGGCCGAA AGGUGUA |
| 1787 | 935 | UGAGGAC CUGAUGAGGCCGAAAGGCCGAA AUGCCCU |
| 1790 | 936 | GACUGAG CUGAUGAGGCCGAAAGGCCGAA ACAAUGC |
| 1793 | 937 | UCUGACU CUGAUGAGGCCGAAAGGCCGAA AGGACAA |
| 1797 | 938 | UGUAUCU CUGAUGAGGCCGAAAGGCCGAA ACUGAGG |
| 1802 | 939 | GCUGUUG CUGAUGAGGCCGAAAGGCCGAA AUCUGAC |
| 1812 | 940 | GGCCCCA CUGAUGAGGCCGAAAGGCCGAA AUGCUGU |
| 1813 | 941 | UGGCCCC CUGAUGAGGCCGAAAGGCCGAA AAUGCUG |
| 1825 | 942 | GUGCAGG CUGAUGAGGCCGAAAGGCCGAA ACCAUGG |
| 1837 | 943 | AGUGUUU CUGAUGAGGCCGAAAGGCCGAA AGGUGUG |
| 1845 | 944 | CGUGGCC CUGAUGAGGCCGAAAGGCCGAA AGUGUUU |
| 1856 | 945 | CAGAUCA CUGAUGAGGCCGAAAGGCCGAA AUGCGUG |
| 1861 | 946 | GACUACA CUGAUGAGGCCGAAAGGCCGAA AUCAGAU |
| 1865 | 947 | AUGUGAC CUGAUGAGGCCGAAAGGCCGAA ACAGAUC |
| 1868 | 948 | GUCAUGU CUGAUGAGGCCGAAAGGCCGAA ACUACAG |
| 1877 | 949 | CUUGGCU CUGAUGAGGCCGAAAGGCCGAA AGUCAUG |
| 1901 | 950 | AUGUCUU CUGAUGAGGCCGAAAGGCCGAA AGUCUUG |

34

| | | |
|---|---|---|
| 1912 | 951 | AUCCAUC CUGAUGAGGCCGAAAGGCCGAA AUCAUGU |
| 1922 | 952 | AGACUUU CUGAUGAGGCCGAAAGGCCGAA ACAUCCA |
| 1923 | 953 | UAGACUU CUGAUGAGGCCGAAAGGCCGAA AACAUCC |
| 1928 | 954 | CAGGCUA CUGAUGAGGCCGAAAGGCCGAA ACUUUAA |
| 1930 | 955 | AUCAGGC CUGAUGAGGCCGAAAGGCCGAA AGACUUU |
| 1964 | 956 | GUGGGGC CUGAUGAGGCCGAAAGGCCGAA AUGUCUC |
| 1983 | 957 | CCAGUUG CUGAUGAGGCCGAAAGGCCGAA AUGUCCU |
| 1996 | 958 | GUUUCAG CUGAUGAGGCCGAAAGGCCGAA AUUCCCC |
| 2005 | 959 | AGGCAGC CUGAUGAGGCCGAAAGGCCGAA AGUUUCA |
| 2013 | 960 | UACCCAA CUGAUGAGGCCGAAAGGCCGAA AGGCAGC |
| 2015 | 961 | CAUACCC CUGAUGAGGCCGAAAGGCCGAA AUAGGCA |
| 2020 | 962 | CUCAGCA CUGAUGAGGCCGAAAGGCCGAA ACCCAAU |
| 2039 | 963 | CUUCUGU CUGAUGAGGCCGAAAGGCCGAA AGUCUGU |
| 2040 | 964 | UCUUCUG CUGAUGAGGCCGAAAGGCCGAA AAGUCUG |
| 2057 | 965 | GUCUAUG CUGAUGAGGCCGAAAGGCCGAA AGGGCCA |
| 2061 | 966 | ACAUGUC CUGAUGAGGCCGAAAGGCCGAA AUGGAGG |
| 2071 | 967 | UUGAUGC CUGAUGAGGCCGAAAGGCCGAA ACACAUG |
| 2076 | 968 | GUGUUUU CUGAUGAGGCCGAAAGGCCGAA AUGCUAC |
| 2097 | 969 | CGUCAGG CUGAUGAGGCCGAAAGGCCGAA AGUGUGG |
| 2098 | 970 | CCGUCAG CUGAUGAGGCCGAAAGGCCGAA AAGUGUG |
| 2115 | 971 | AGUGCCC CUGAUGAGGCCGAAAGGCCGAA AGCUGGC |
| 2128 | 972 | GUCAGUA CUGAUGAGGCCGAAAGGCCGAA ACAGCAG |
| 2130 | 973 | GGGUCAG CUGAUGAGGCCGAAAGGCCGAA AGACAGC |
| 2145 | 974 | UAUCAUC CUGAUGAGGCCGAAAGGCCGAA AGGGUUG |
| 2152 | 975 | AAAUACA CUGAUGAGGCCGAAAGGCCGAA AUCAUCA |
| 2156 | 976 | GAAUAAA CUGAUGAGGCCGAAAGGCCGAA ACAUAUC |
| 2158 | 977 | AUGAAUA CUGAUGAGGCCGAAAGGCCGAA AUACAUA |
| 2159 | 978 | AAUGAAU CUGAUGAGGCCGAAAGGCCGAA AAUACAU |
| 2160 | 979 | AAAUGAA CUGAUGAGGCCGAAAGGCCGAA AAAUACA |
| 2162 | 980 | ACAAAUG CUGAUGAGGCCGAAAGGCCGAA AUAAAUA |
| 2163 | 981 | AACAAAU CUGAUGAGGCCGAAAGGCCGAA AAUAAAU |
| 2166 | 982 | AAUAACA CUGAUGAGGCCGAAAGGCCGAA AUGAAUA |
| 2167 | 983 | AAAUAAC CUGAUGAGGCCGAAAGGCCGAA AAUGAAU |
| 2170 | 984 | GUAAAAU CUGAUGAGGCCGAAAGGCCGAA ACAAAUG |
| 2171 | 985 | GGUAAAA CUGAUGAGGCCGAAAGGCCGAA AACAAAU |
| 2173 | 986 | CUGGUAA CUGAUGAGGCCGAAAGGCCGAA AUAACAA |
| 2174 | 987 | GCUGGUA CUGAUGAGGCCGAAAGGCCGAA AAUAACA |
| 2175 | 988 | AGCUGGU CUGAUGAGGCCGAAAGGCCGAA AAAUAAC |
| 2176 | 989 | UAGCUGG CUGAUGAGGCCGAAAGGCCGAA AAAAUAA |
| 2183 | 990 | CAAUAAA CUGAUGAGGCCGAAAGGCCGAA AGCUGGU |
| 2185 | 991 | CUCAAUA CUGAUGAGGCCGAAAGGCCGAA AUAGCUG |
| 2186 | 992 | ACUCAAU CUGAUGAGGCCGAAAGGCCGAA AAUAGCU |
| 2187 | 993 | CACUCAA CUGAUGAGGCCGAAAGGCCGAA AAAUAGC |
| 2189 | 994 | GACACUC CUGAUGAGGCCGAAAGGCCGAA AUAAAUA |
| 2196 | 995 | CAUAAAA CUGAUGAGGCCGAAAGGCCGAA ACACUCA |
| 2198 | 996 | UACAUAA CUGAUGAGGCCGAAAGGCCGAA AGACACU |
| 2199 | 997 | CUACAUA CUGAUGAGGCCGAAAGGCCGAA AAGACAC |
| 2200 | 998 | CCUACAU CUGAUGAGGCCGAAAGGCCGAA AAAGACA |

35

| | | |
|---|---|---|
| 2201 | 999 | GCCUACA CUGAUGAGGCCGAAAGGCCGAA AAAAGAC |
| 2205 | 1000 | UUUAGCC CUGAUGAGGCCGAAAGGCCGAA ACAUAAA |
| 2210 | 1001 | GUUCAUU CUGAUGAGGCCGAAAGGCCGAA AGCCUAC |
| 2220 | 1002 | AGAGACC CUGAUGAGGCCGAAAGGCCGAA AUGUUCA |
| 2224 | 1003 | GGCCAGA CUGAUGAGGCCGAAAGGCCGAA ACCUAUG |
| 2226 | 1004 | GAGGCCA CUGAUGAGGCCGAAAGGCCGAA AGACCUA |
| 2233 | 1005 | GCUCCGU CUGAUGAGGCCGAAAGGCCGAA AGGCCAG |
| 2242 | 1006 | GGACUGG CUGAUGAGGCCGAAAGGCCGAA AGCUCCG |
| 2248 | 1007 | UGACAUG CUGAUGAGGCCGAAAGGCCGAA ACUGGGA |
| 2254 | 1008 | UGAAUGU CUGAUGAGGCCGAAAGGCCGAA ACAUGGA |
| 2259 | 1009 | GACCUUG CUGAUGAGGCCGAAAGGCCGAA AUGUGAC |
| 2260 | 1010 | UGACCUU CUGAUGAGGCCGAAAGGCCGAA AAUGUGA |
| 2266 | 1011 | ACCUGGU CUGAUGAGGCCGAAAGGCCGAA ACCUUGA |
| 2274 | 1012 | ACAACUG CUGAUGAGGCCGAAAGGCCGAA ACCUGGU |
| 2279 | 1013 | CCUGUAC CUGAUGAGGCCGAAAGGCCGAA ACUGUAC |
| 2282 | 1014 | CAACCUG CUGAUGAGGCCGAAAGGCCGAA ACAACUG |
| 2288 | 1015 | AGUGUAC CUGAUGAGGCCGAAAGGCCGAA ACCUGUA |
| 2291 | 1016 | UGCAGUG CUGAUGAGGCCGAAAGGCCGAA ACAACCU |
| 2321 | 1017 | CCCAUUU CUGAUGAGGCCGAAAGGCCGAA AUCUUUU |
| 2338 | 1018 | CAAUGAG CUGAUGAGGCCGAAAGGCCGAA AGUCCCA |
| 2339 | 1019 | CCAAUGA CUGAUGAGGCCGAAAGGCCGAA AAGUCCC |
| 2341 | 1020 | GGCCAAU CUGAUGAGGCCGAAAGGCCGAA AGAAGUC |
| 2344 | 1021 | GUUGGCC CUGAUGAGGCCGAAAGGCCGAA AUGAGAA |
| 2358 | 1022 | CUGGGA CUGAUGAGGCCGAAAGGCCGAA AGGCAGG |
| 2359 | 1023 | UCUGGGG CUGAUGAGGCCGAAAGGCCGAA AAGGCAG |
| 2360 | 1024 | UUCUGGG CUGAUGAGGCCGAAAGGCCGAA AAAGGCA |
| 2376 | 1025 | AUAGAAA CUGAUGAGGCCGAAAGGCCGAA AUCACUC |
| 2377 | 1026 | GAUAGAA CUGAUGAGGCCGAAAGGCCGAA AAUCACU |
| 2378 | 1027 | CGAUAGA CUGAUGAGGCCGAAAGGCCGAA AAAUCAC |
| 2379 | 1028 | CCGAUAG CUGAUGAGGCCGAAAGGCCGAA AAAAUCA |
| 2380 | 1029 | GCCGAUA CUGAUGAGGCCGAAAGGCCGAA AAAAAUC |
| 2382 | 1030 | GUGCCGA CUGAUGAGGCCGAAAGGCCGAA AGAAAAA |
| 2384 | 1031 | UUGUGCC CUGAUGAGGCCGAAAGGCCGAA AUAGAAA |
| 2399 | 1032 | GUCCAUA CUGAUGAGGCCGAAAGGCCGAA AGUGCUU |
| 2401 | 1033 | CAGUCCA CUGAUGAGGCCGAAAGGCCGAA AUAGUGC |
| 2411 | 1034 | GAACCAU CUGAUGAGGCCGAAAGGCCGAA ACCAGUC |
| 2417 | 1035 | ACCUGUG CUGAUGAGGCCGAAAGGCCGAA ACCAUUA |
| 2418 | 1036 | AACCUGU CUGAUGAGGCCGAAAGGCCGAA AACCAUU |
| 2425 | 1037 | AUCUCUG CUGAUGAGGCCGAAAGGCCGAA ACCUGUG |
| 2426 | 1038 | AAUCUCU CUGAUGAGGCCGAAAGGCCGAA AACCUGU |
| 2433 | 1039 | ACUGGGU CUGAUGAGGCCGAAAGGCCGAA AUCUCUG |
| 2434 | 1040 | CACUGGG CUGAUGAGGCCGAAAGGCCGAA AAUCUCU |
| 2448 | 1041 | GAGGAAU CUGAUGAGGCCGAAAGGCCGAA AGGCCUC |
| 2449 | 1042 | GGAGGAA CUGAUGAGGCCGAAAGGCCGAA AAGGCCU |
| 2451 | 1043 | AGGGAGG CUGAUGAGGCCGAAAGGCCGAA AUAAGGC |
| 2452 | 1044 | AAGGGAG CUGAUGAGGCCGAAAGGCCGAA AAUAAGG |
| 2455 | 1045 | GGGAAGG CUGAUGAGGCCGAAAGGCCGAA AGGAAUA |
| 2459 | 1046 | UGGGGGG CUGAUGAGGCCGAAAGGCCGAA AGGGAGG |

36

| | | |
|---|---|---|
| 2460 | 1047 | UUGGGGG CUGAUGAGGCCGAAAGGCCGAA AAGGGAG |
| 2479 | 1048 | GCUAACA CUGAUGAGGCCGAAAGGCCGAA AGGUGUC |
| 2480 | 1049 | GGCUAAC CUGAUGAGGCCGAAAGGCCGAA AAGGUGU |
| 2483 | 1050 | GGUGGCU CUGAUGAGGCCGAAAGGCCGAA ACAAAGG |
| 2484 | 1051 | AGGUGGC CUGAUGAGGCCGAAAGGCCGAA AACAAAG |
| 2492 | 1052 | GGGUGGG CUGAUGAGGCCGAAAGGCCGAA AGGUGGC |
| 2504 | 1053 | AGAAAUG CUGAUGAGGCCGAAAGGCCGAA AUGUGGG |
| 2508 | 1054 | UGGCAGA CUGAUGAGGCCGAAAGGCCGAA AUGUAUG |
| 2509 | 1055 | CUGGCAG CUGAUGAGGCCGAAAGGCCGAA AAUGUAU |
| 2510 | 1056 | ACUGGCA CUGAUGAGGCCGAAAGGCCGAA AAAUGUA |
| 2520 | 1057 | CAUUGUG CUGAUGAGGCCGAAAGGCCGAA ACACUGG |
| 2521 | 1058 | UCAUUGU CUGAUGAGGCCGAAAGGCCGAA AACACUG |
| 2533 | 1059 | GACCGCU CUGAUGAGGCCGAAAGGCCGAA AGUGUCA |
| 2540 | 1060 | CAGACAU CUGAUGAGGCCGAAAGGCCGAA ACCGCUG |
| 2545 | 1061 | AUGUCCA CUGAUGAGGCCGAAAGGCCGAA ACAUGAC |
| 2568 | 1062 | UUGGGCA CUGAUGAGGCCGAAAGGCCGAA AUUCCCU |
| 2579 | 1063 | CAAGGCA CUGAUGAGGCCGAAAGGCCGAA AGCUUGG |
| 2585 | 1064 | AGAGGAC CUGAUGAGGCCGAAAGGCCGAA AGGCAUA |
| 2588 | 1065 | ACAAGAG CUGAUGAGGCCGAAAGGCCGAA ACAAGGC |
| 2591 | 1066 | AGGACAA CUGAUGAGGCCGAAAGGCCGAA AGGACAA |
| 2593 | 1067 | ACAGGAC CUGAUGAGGCCGAAAGGCCGAA AGAGGAC |
| 2596 | 1068 | CAAACAG CUGAUGAGGCCGAAAGGCCGAA ACAAGAG |
| 2601 | 1069 | AAAUGCA CUGAUGAGGCCGAAAGGCCGAA ACAGGAC |
| 2602 | 1070 | GAAAUGC CUGAUGAGGCCGAAAGGCCGAA AACAGGA |
| 2607 | 1071 | CCAGUGA CUGAUGAGGCCGAAAGGCCGAA AUGCAAA |
| 2608 | 1072 | CCCAGUG CUGAUGAGGCCGAAAGGCCGAA AAUGCAA |
| 2609 | 1073 | UCCCAGU CUGAUGAGGCCGAAAGGCCGAA AAAUGCA |
| 2620 | 1074 | AUAGUGC CUGAUGAGGCCGAAAGGCCGAA AGCUCCC |
| 2626 | 1075 | GCUGCAA CUGAUGAGGCCGAAAGGCCGAA AGUGCAA |
| 2628 | 1076 | GAGCUGC CUGAUGAGGCCGAAAGGCCGAA AUAGUGC |
| 2635 | 1077 | GAAACUG CUGAUGAGGCCGAAAGGCCGAA AGCUGCA |
| 2640 | 1078 | UGCAGGA CUGAUGAGGCCGAAAGGCCGAA ACUGGAG |
| 2641 | 1079 | CUGCAGG CUGAUGAGGCCGAAAGGCCGAA AACUGGA |
| 2642 | 1080 | ACUGCAG CUGAUGAGGCCGAAAGGCCGAA AAACUGG |
| 2653 | 1081 | GGACCCU CUGAUGAGGCCGAAAGGCCGAA AUCACUG |
| 2659 | 1082 | CUUGCAG CUGAUGAGGCCGAAAGGCCGAA ACCCUGA |
| 2689 | 1083 | CCUCCAA CUGAUGAGGCCGAAAGGCCGAA ACCUUGG |
| 2691 | 1084 | GUCCUCC CUGAUGAGGCCGAAAGGCCGAA AUACCUU |
| 2700 | 1085 | UGGGAGG CUGAUGAGGCCGAAAGGCCGAA AGUCCUC |
| 2704 | 1086 | AAGCUGG CUGAUGAGGCCGAAAGGCCGAA AGGGAGU |
| 2711 | 1087 | CCUUCCA CUGAUGAGGCCGAAAGGCCGAA AGCUGGG |
| 2712 | 1088 | CCCUUCC CUGAUGAGGCCGAAAGGCCGAA AAGCUGG |
| 2721 | 1089 | CGCGGAU CUGAUGAGGCCGAAAGGCCGAA ACCCUUC |
| 2724 | 1090 | ACACGCG CUGAUGAGGCCGAAAGGCCGAA AUGACCC |
| 2744 | 1091 | CUACACA CUGAUGAGGCCGAAAGGCCGAA ACACACA |
| 2750 | 1092 | GCUUGUC CUGAUGAGGCCGAAAGGCCGAA ACACAUA |
| 2759 | 1093 | AGAGCGA CUGAUGAGGCCGAAAGGCCGAA AGCUUGU |
| 2761 | 1094 | ACAGAGC CUGAUGAGGCCGAAAGGCCGAA AGAGCUU |

37

| | | |
|---|---|---|
| 2765 | 1095 | GGUGACA CUGAUGAGGCCGAAAGGCCGAA AGCGAGA |
| 2769 | 1096 | CCUGGGU CUGAUGAGGCCGAAAGGCCGAA ACAGAGC |
| 2797 | 1097 | GAACCAU CUGAUGAGGCCGAAAGGCCGAA AUUGCAC |
| 2803 | 1098 | UGCAGUG CUGAUGAGGCCGAAAGGCCGAA ACCAUGA |
| 2804 | 1099 | CUGCAGU CUGAUGAGGCCGAAAGGCCGAA AACCAUG |
| 2813 | 1100 | AGGUCAA CUGAUGAGGCCGAAAGGCCGAA ACUGCAG |
| 2815 | 1101 | AAAGGUC CUGAUGAGGCCGAAAGGCCGAA AGACUGC |
| 2821 | 1102 | AGCCCAA CUGAUGAGGCCGAAAGGCCGAA AGGUCAA |
| 2822 | 1103 | GAGCCCA CUGAUGAGGCCGAAAGGCCGAA AAGGUCA |
| 2823 | 1104 | UGAGCCC CUGAUGAGGCCGAAAGGCCGAA AAAGGUC |
| 2829 | 1105 | AUCACUU CUGAUGAGGCCGAAAGGCCGAA AGCCCAA |
| 2837 | 1106 | GUGGGAG CUGAUGAGGCCGAAAGGCCGAA AUCACUU |
| 2840 | 1107 | GAGGUGG CUGAUGAGGCCGAAAGGCCGAA AGGAUCA |
| 2847 | 1108 | GGAGGCU CUGAUGAGGCCGAAAGGCCGAA AGGUGGG |
| 2853 | 1109 | UACUCAG CUGAUGAGGCCGAAAGGCCGAA AGGCUGA |
| 2860 | 1110 | UCCCAGC CUGAUGAGGCCGAAAGGCCGAA ACUCAGG |
| 2872 | 1111 | GUGAGCC CUGAUGAGGCCGAAAGGCCGAA AUGGUCC |
| 2877 | 1112 | GUGUUGU CUGAUGAGGCCGAAAGGCCGAA AGCCUAU |
| 2899 | 1113 | AAAAUCA CUGAUGAGGCCGAAAGGCCGAA AUUUGCC |
| 2900 | 1114 | AAAAAUC CUGAUGAGGCCGAAAGGCCGAA AAUUUGC |
| 2904 | 1115 | AAAAAAA CUGAUGAGGCCGAAAGGCCGAA AUCAAAU |
| 2905 | 1116 | AAAAAAA CUGAUGAGGCCGAAAGGCCGAA AAUCAAA |
| 2906 | 1117 | AAAAAAA CUGAUGAGGCCGAAAGGCCGAA AAAUCAA |
| 2907 | 1118 | AAAAAAA CUGAUGAGGCCGAAAGGCCGAA AAAAUCA |
| 2908 | 1119 | AAAAAAA CUGAUGAGGCCGAAAGGCCGAA AAAAAUC |
| 2909 | 1120 | AAAAAAA CUGAUGAGGCCGAAAGGCCGAA AAAAAAU |
| 2910 | 1121 | AAAAAAA CUGAUGAGGCCGAAAGGCCGAA AAAAAAA |
| 2911 | 1122 | AAAAAAA CUGAUGAGGCCGAAAGGCCGAA AAAAAAA |
| 2912 | 1123 | GAAAAAA CUGAUGAGGCCGAAAGGCCGAA AAAAAAA |
| 2913 | 1124 | UGAAAAA CUGAUGAGGCCGAAAGGCCGAA AAAAAAA |
| 2914 | 1125 | CUGAAAA CUGAUGAGGCCGAAAGGCCGAA AAAAAAA |
| 2915 | 1126 | UCUGAAA CUGAUGAGGCCGAAAGGCCGAA AAAAAAA |
| 2916 | 1127 | CUCUGAA CUGAUGAGGCCGAAAGGCCGAA AAAAAAA |
| 2917 | 1128 | UCUCUGA CUGAUGAGGCCGAAAGGCCGAA AAAAAAA |
| 2918 | 1129 | GUCUCUG CUGAUGAGGCCGAAAGGCCGAA AAAAAAA |
| 2919 | 1130 | CGUCUCU CUGAUGAGGCCGAAAGGCCGAA AAAAAAA |
| 2931 | 1131 | GUUGCGA CUGAUGAGGCCGAAAGGCCGAA ACCCCGU |
| 2933 | 1132 | AUGUUGC CUGAUGAGGCCGAAAGGCCGAA AGACCCC |
| 2941 | 1133 | UCUGGGC CUGAUGAGGCCGAAAGGCCGAA AUGUUGC |
| 2951 | 1134 | ACAAAGG CUGAUGAGGCCGAAAGGCCGAA AGUCUGG |
| 2952 | 1135 | CACAAAG CUGAUGAGGCCGAAAGGCCGAA AAGUCUG |
| 2955 | 1136 | UAACACA CUGAUGAGGCCGAAAGGCCGAA AGGAAGU |
| 2956 | 1137 | CUAACAC CUGAUGAGGCCGAAAGGCCGAA AAGGAAG |
| 2961 | 1138 | AUUAACU CUGAUGAGGCCGAAAGGCCGAA ACACAAA |
| 2962 | 1139 | UAUUAAC CUGAUGAGGCCGAAAGGCCGAA AACACAA |
| 2965 | 1140 | CUUUAUU CUGAUGAGGCCGAAAGGCCGAA ACUAACA |
| 2966 | 1141 | GCUUUAU CUGAUGAGGCCGAAAGGCCGAA AACUAAC |
| 2969 | 1142 | AAAGCUU CUGAUGAGGCCGAAAGGCCGAA AUUAACU |

38

| 2975 | 1143 | GUUGAGA CUGAUGAGGCCGAAAGGCCGAA AGCUUUA |
| --- | --- | --- |
| 2976 | 1144 | AGUUGAG CUGAUGAGGCCGAAAGGCCGAA AAGCUUU |
| 2977 | 1145 | CAGUUGA CUGAUGAGGCCGAAAGGCCGAA AAAGCUU |
| 2979 | 1146 | GGCAGUU CUGAUGAGGCCGAAAGGCCGAA AGAAAGC |

39

Table V

Mouse ICAM HH Ribozyme Sequence

| nt. Position | SEQ ID NO | Ribozyme Sequence |
|---|---|---|
| 11 | 1147 | CAACGGU CUGAUGAGGCCGAAAGGCCGAA ACCAGGG |
| 23 | 1148 | AGCAGAG CUGAUGAGGCCGAAAGGCCGAA ACCACUG |
| 26 | 1149 | AGGAGCA CUGAUGAGGCCGAAAGGCCGAA AGAACCA |
| 31 | 1150 | UGUGGAG CUGAUGAGGCCGAAAGGCCGAA AGCAGAG |
| 34 | 1151 | CGACCCU CUGAUGAGGCCGAAAGGCCGAA AUGAGAA |
| 40 | 1152 | AGGCUAC CUGAUGAGGCCGAAAGGCCGAA AGUGUGC |
| 48 | 1153 | CCAGGCU CUGAUGAGGCCGAAAGGCCGAA AGGUCCU |
| 54 | 1154 | CCAUCAC CUGAUGAGGCCGAAAGGCCGAA AGGCCCA |
| 58 | 1155 | GGAGCUA CUGAUGAGGCCGAAAGGCCGAA AGGCAUG |
| 64 | 1156 | CUGCUGG CUGAUGAGGCCGAAAGGCCGAA AGGGGUG |
| 96 | 1157 | GGGCCAG CUGAUGAGGCCGAAAGGCCGAA AGCAGAG |
| 102 | 1158 | CCAGCAG CUGAUGAGGCCGAAAGGCCGAA ACUGGCA |
| 108 | 1159 | GGGCCAG CUGAUGAGGCCGAAAGGCCGAA AGCAGAG |
| 115 | 1160 | AGGAGCA CUGAUGAGGCCGAAAGGCCGAA AGAACCA |
| 119 | 1161 | UCCUGGU CUGAUGAGGCCGAAAGGCCGAA ACAUUCC |
| 120 | 1162 | GGGCCAG CUGAUGAGGCCGAAAGGCCGAA AGCAGAG |
| 146 | 1163 | GGAAGCG CUGAUGAGGCCGAAAGGCCGAA ACGACUG |
| 152 | 1164 | AGUGGCU CUGAUGAGGCCGAAAGGCCGAA ACACAGA |
| 158 | 1165 | GGUUUUU CUGAUGAGGCCGAAAGGCCGAA AACAGGA |
| 165 | 1166 | GCAAAAC CUGAUGAGGCCGAAAGGCCGAA ACUUCUG |
| 168 | 1167 | GGGGCAG CUGAUGAGGCCGAAAGGCCGAA AAGGCUU |
| 185 | 1168 | CUGCACG CUGAUGAGGCCGAAAGGCCGAA ACCCACC |
| 209 | 1169 | GCCAGAG CUGAUGAGGCCGAAAGGCCGAA AAGUGGC |
| 227 | 1170 | GCAAAAC CUGAUGAGGCCGAAAGGCCGAA ACUUCUG |
| 230 | 1171 | GGAGCAA CUGAUGAGGCCGAAAGGCCGAA ACAACUU |
| 237 | 1172 | AGUUCUC CUGAUGAGGCCGAAAGGCCGAA AAGCACA |
| 248 | 1173 | UUUAGGA CUGAUGAGGCCGAAAGGCCGAA AUGGGUU |
| 253 | 1174 | UCUUCCU CUGAUGAGGCCGAAAGGCCGAA AGGCAGG |
| 263 | 1175 | CAGUAGA CUGAUGAGGCCGAAAGGCCGAA AAACCCU |
| 267 | 1176 | UAGGCAG CUGAUGAGGCCGAAAGGCCGAA AGCCCCU |
| 293 | 1177 | CAGCUCA CUGAUGAGGCCGAAAGGCCGAA ACAGCUU |
| 319 | 1178 | GGCUCAG CUGAUGAGGCCGAAAGGCCGAA AUCUCCU |
| 335 | 1179 | GUUCUCA CUGAUGAGGCCGAAAGGCCGAA AGCACAG |
| 337 | 1180 | CAGUGUG CUGAUGAGGCCGAAAGGCCGAA AUUGGAC |
| 338 | 1181 | UCAGCUC CUGAUGAGGCCGAAAGGCCGAA AACAGCU |
| 359 | 1182 | AGCGGAC CUGAUGAGGCCGAAAGGCCGAA ACUGCAC |
| 367 | 1183 | CGGGUUG CUGAUGAGGCCGAAAGGCCGAA AGCCAUU |
| 374 | 1184 | GGGCAGG CUGAUGAGGCCGAAAGGCCGAA AGGCUUC |
| 375 | 1185 | GGGGCAG CUGAUGAGGCCGAAAGGCCGAA AAGGCUU |
| 378 | 1186 | ACACGGU CUGAUGAGGCCGAAAGGCCGAA AUGGUAG |
| 386 | 1187 | AAACGAA CUGAUGAGGCCGAAAGGCCGAA ACACGGU |

40

| | | |
|---|---|---|
| 394 | 1188 | AGAUCGA CUGAUGAGGCCGAAAGGCCGAA AGUCCGG |
| 420 | 1189 | CGGGGGG CUGAUGAGGCCGAAAGGCCGAA AAGUGUG |
| 425 | 1190 | CUGCUGG CUGAUGAGGCCGAAAGGCCGAA AGGGGUG |
| 427 | 1191 | CACUGCU CUGAUGAGGCCGAAAGGCCGAA AGAGCUG |
| 450 | 1192 | GCAGGGU CUGAUGAGGCCGAAAGGCCGAA AGGUCCU |
| 451 | 1193 | CAAAGGA CUGAUGAGGCCGAAAGGCCGAA AGGUUUC |
| 456 | 1194 | AGUGGCU CUGAUGAGGCCGAAAGGCCGAA AGGGUAA |
| 495 | 1195 | ACACGGU CUGAUGAGGCCGAAAGGCCGAA AUGGUAG |
| 510 | 1196 | CCCCACG CUGAUGAGGCCGAAAGGCCGAA AGCAGCA |
| 564 | 1197 | GGAUGGA CUGAUGAGGCCGAAAGGCCGAA ACCUGAG |
| 592 | 1198 | CCCAUGU CUGAUGAGGCCGAAAGGCCGAA AUCUUUC |
| 607 | 1199 | CAUGAGA CUGAUGAGGCCGAAAGGCCGAA AUUGGCU |
| 608 | 1200 | GCAUGAG CUGAUGAGGCCGAAAGGCCGAA AAUUGGC |
| 609 | 1201 | GGCAUGA CUGAUGAGGCCGAAAGGCCGAA AAAUUGG |
| 611 | 1202 | GCGGCAU CUGAUGAGGCCGAAAGGCCGAA AGAAAUU |
| 656 | 1203 | CAGCUCA CUGAUGAGGCCGAAAGGCCGAA ACAGCUU |
| 657 | 1204 | UCAGCUC CUGAUGAGGCCGAAAGGCCGAA AACAGCU |
| 668 | 1205 | GGUGGCC CUGAUGAGGCCGAAAGGCCGAA AGGCUCG |
| 677 | 1206 | AGGCUGG CUGAUGAGGCCGAAAGGCCGAA AGAGGUC |
| 684 | 1207 | AGGACCG CUGAUGAGGCCGAAAGGCCGAA AGCUGAA |
| 692 | 1208 | AAGAUCG CUGAUGAGGCCGAAAGGCCGAA AAGUCCG |
| 693 | 1209 | GCAGGGU CUGAUGAGGCCGAAAGGCCGAA AGGUCCU |
| 696 | 1210 | GAGGCAG CUGAUGAGGCCGAAAGGCCGAA AAACAGG |
| 709 | 1211 | UGAGGUG CUGAUGAGGCCGAAAGGCCGAA AGCCGCC |
| 720 | 1212 | AGCUGAA CUGAUGAGGCCGAAAGGCCGAA AGUUGUA |
| 723 | 1213 | CGGAGCU CUGAUGAGGCCGAAAGGCCGAA AAAAGUU |
| 735 | 1214 | UCUCCAG CUGAUGAGGCCGAAAGGCCGAA AUCUGGU |
| 738 | 1215 | CCAUCAC CUGAUGAGGCCGAAAGGCCGAA AGGCCCA |
| 765 | 1216 | GGAAGCG CUGAUGAGGCCGAAAGGCCGAA ACGACUG |
| 769 | 1217 | GGCAGGA CUGAUGAGGCCGAAAGGCCGAA ACAGGCC |
| 770 | 1218 | UUCCAGG CUGAUGAGGCCGAAAGGCCGAA AGCAAAA |
| 785 | 1219 | GGCAGGA CUGAUGAGGCCGAAAGGCCGAA ACAGGCC |
| 786 | 1220 | AGGCAGG CUGAUGAGGCCGAAAGGCCGAA AACAGGC |
| 792 | 1221 | CUUCCGA CUGAUGAGGCCGAAAGGCCGAA ACCUCCA |
| 794 | 1222 | AGUCUCC CUGAUGAGGCCGAAAGGCCGAA AGCCCAG |
| 807 | 1223 | CCAGGUA CUGAUGAGGCCGAAAGGCCGAA AUCCGAG |
| 833 | 1224 | GGGUGUC CUGAUGAGGCCGAAAGGCCGAA AGCUUUG |
| 846 | 1225 | CAACGGU CUGAUGAGGCCGAAAGGCCGAA ACCAGGG |
| 851 | 1226 | GCUGGUA CUGAUGAGGCCGAAAGGCCGAA AGGUCUC |
| 863 | 1227 | CCAGAGG CUGAUGAGGCCGAAAGGCCGAA AGUGGCU |
| 866 | 1228 | GGGCAGG CUGAUGAGGCCGAAAGGCCGAA AGGCUUC |
| 867 | 1229 | UCUCCGG CUGAUGAGGCCGAAAGGCCGAA AACGAAU |
| 869 | 1230 | CUUGCAU CUGAUGAGGCCGAAAGGCCGAA AGGAAGA |
| 881 | 1231 | ACGGGUU CUGAUGAGGCCGAAAGGCCGAA AAGCCAU |
| 885 | 1232 | UCACCUC CUGAUGAGGCCGAAAGGCCGAA ACCAAGG |
| 933 | 1233 | CCAGAAU CUGAUGAGGCCGAAAGGCCGAA AUUAUAG |
| 936 | 1234 | GCACCAG CUGAUGAGGCCGAAAGGCCGAA AUGAUUA |
| 978 | 1235 | AGUUGUA CUGAUGAGGCCGAAAGGCCGAA ACUGUUA |

41

| | | |
|---|---|---|
| 980 | 1236 | AAAGUUG CUGAUGAGGCCGAAAGGCCGAA AGACUGU |
| 986 | 1237 | AGCUGAA CUGAUGAGGCCGAAAGGCCGAA AGUUGUA |
| 987 | 1238 | GAGCUGA CUGAUGAGGCCGAAAGGCCGAA AAGUUGU |
| 988 | 1239 | GGAGCUG CUGAUGAGGCCGAAAGGCCGAA AAAGUUG |
| 1005 | 1240 | UCUCCAG CUGAUGAGGCCGAAAGGCCGAA AUCUGGU |
| 1006 | 1241 | UUCCCCA CUGAUGAGGCCGAAAGGCCGAA ACUCUCA |
| 1023 | 1242 | CUUCCGA CUGAUGAGGCCGAAAGGCCGAA ACCUCCA |
| 1025 | 1243 | CCCUUCC CUGAUGAGGCCGAAAGGCCGAA AGACCUC |
| 1066 | 1244 | UUAUUUU CUGAUGAGGCCGAAAGGCCGAA AGAGUGG |
| 1092 | 1245 | GGCCUGA CUGAUGAGGCCGAAAGGCCGAA AUCCAGU |
| 1093 | 1246 | UUGGCUG CUGAUGAGGCCGAAAGGCCGAA AGGUCCA |
| 1125 | 1247 | UCAAGAA CUGAUGAGGCCGAAAGGCCGAA AGUUGGG |
| 1163 | 1248 | GCAAAAG CUGAUGAGGCCGAAAGGCCGAA AGCUUCG |
| 1164 | 1249 | AGCAAAA CUGAUGAGGCCGAAAGGCCGAA AAGCUUC |
| 1166 | 1250 | AGAGCAA CUGAUGAGGCCGAAAGGCCGAA AGAAGCU |
| 1172 | 1251 | GGUUUUU CUGAUGAGGCCGAAAGGCCGAA AACAGGA |
| 1200 | 1252 | UGUGGAG CUGAUGAGGCCGAAAGGCCGAA AGCAGAG |
| 1201 | 1253 | CUGUUCA CUGAUGAGGCCGAAAGGCCGAA AAGCAGC |
| 1203 | 1254 | ACUGGUG CUGAUGAGGCCGAAAGGCCGAA AAAAAGU |
| 1227 | 1255 | GCACACG CUGAUGAGGCCGAAAGGCCGAA AUGUACC |
| 1228 | 1256 | AGCAAAA CUGAUGAGGCCGAAAGGCCGAA AAGCUUC |
| 1233 | 1257 | CUCUCCG CUGAUGAGGCCGAAAGGCCGAA AAACGAA |
| 1238 | 1258 | AGGACCA CUGAUGAGGCCGAAAGGCCGAA ACAGCAC |
| 1264 | 1259 | CUUGCAC CUGAUGAGGCCGAAAGGCCGAA ACCCUUC |
| 1267 | 1260 | UUCCCCA CUGAUGAGGCCGAAAGGCCGAA ACUCUCA |
| 1294 | 1261 | GGCUCAG CUGAUGAGGCCGAAAGGCCGAA AUCUCCU |
| 1295 | 1262 | CUGCUGA CUGAUGAGGCCGAAAGGCCGAA ACCCCUC |
| 1306 | 1263 | CAUUUCA CUGAUGAGGCCGAAAGGCCGAA AGUCUGC |
| 1321 | 1264 | UCCUCCU CUGAUGAGGCCGAAAGGCCGAA AGCCUUC |
| 1334 | 1265 | UUUAGGA CUGAUGAGGCCGAAAGGCCGAA AUGGGUU |
| 1344 | 1266 | CACUCUC CUGAUGAGGCCGAAAGGCCGAA AGCUCAU |
| 1351 | 1267 | UAACUUA CUGAUGAGGCCGAAAGGCCGAA ACAUUCA |
| 1353 | 1268 | CACCUUC CUGAUGAGGCCGAAAGGCCGAA ACCCACU |
| 1366 | 1269 | AGUUGUA CUGAUGAGGCCGAAAGGCCGAA ACUGUUA |
| 1367 | 1270 | AGGUGGG CUGAUGAGGCCGAAAGGCCGAA AGGUGCU |
| 1368 | 1271 | AGAGUGG CUGAUGAGGCCGAAAGGCCGAA ACAGUAC |
| 1380 | 1272 | CCACCCC CUGAUGAGGCCGAAAGGCCGAA AUGGGCA |
| 1388 | 1273 | AGCCACU CUGAUGAGGCCGAAAGGCCGAA AGUCUCC |
| 1398 | 1274 | GUUCUGU CUGAUGAGGCCGAAAGGCCGAA ACAGCCA |
| 1402 | 1275 | AGUUCUC CUGAUGAGGCCGAAAGGCCGAA AAGCACA |
| 1408 | 1276 | CCUCCCC CUGAUGAGGCCGAAAGGCCGAA AUCUCGC |
| 1410 | 1277 | CCCUUCC CUGAUGAGGCCGAAAGGCCGAA AGACCUC |
| 1421 | 1278 | ACAAAAG CUGAUGAGGCCGAAAGGCCGAA AGGUGGG |
| 1425 | 1279 | CUCUACC CUGAUGAGGCCGAAAGGCCGAA AGGCAGU |
| 1429 | 1280 | CAGGGGC CUGAUGAGGCCGAAAGGCCGAA AUAGAGA |
| 1444 | 1281 | UCCUCCU CUGAUGAGGCCGAAAGGCCGAA AGCCUUC |
| 1455 | 1282 | UCCUGGU CUGAUGAGGCCGAAAGGCCGAA ACAUUCC |
| 1482 | 1283 | GGGAGCA CUGAUGAGGCCGAAAGGCCGAA AACAACU |

| 1484 | 1284 | CAUGAGG CUGAUGAGGCCGAAAGGCCGAA AGAACAG |
|---|---|---|
| 1493 | 1285 | GUUCUCA CUGAUGAGGCCGAAAGGCCGAA AGCACAG |
| 1500 | 1286 | GGACCAU CUGAUGAGGCCGAAAGGCCGAA AUUUCAU |
| 1503 | 1287 | GAAUGAU CUGAUGAGGCCGAAAGGCCGAA AUAGUCC |
| 1506 | 1288 | CGGUUAU CUGAUGAGGCCGAAAGGCCGAA AACAUAA |
| 1509 | 1289 | ACACGGU CUGAUGAGGCCGAAAGGCCGAA AUGGUAG |
| 1518 | 1290 | CGCCUGG CUGAUGAGGCCGAAAGGCCGAA ACCAUGA |
| 1530 | 1291 | CCAGAAU CUGAUGAGGCCGAAAGGCCGAA AUUAUAG |
| 1533 | 1292 | GGCCCAC CUGAUGAGGCCGAAAGGCCGAA AUGACCA |
| 1551 | 1293 | AGCUGCU CUGAUGAGGCCGAAAGGCCGAA AGGCAUG |
| 1559 | 1294 | AGGUGGG CUGAUGAGGCCGAAAGGCCGAA AGGUGCU |
| 1563 | 1295 | GGUUAUA CUGAUGAGGCCGAAAGGCCGAA ACAUAAG |
| 1565 | 1296 | GCGGUUA CUGAUGAGGCCGAAAGGCCGAA AAACAUA |
| 1567 | 1297 | UGGCGGU CUGAUGAGGCCGAAAGGCCGAA AUAAACA |
| 1584 | 1298 | AUAUCCU CUGAUGAGGCCGAAAGGCCGAA AUCUUUC |
| 1592 | 1299 | UAACUUG CUGAUGAGGCCGAAAGGCCGAA AUAUCCU |
| 1599 | 1300 | CCUUCUG CUGAUGAGGCCGAAAGGCCGAA AACUUGU |
| 1651 | 1301 | GCUCAGG CUGAUGAGGCCGAAAGGCCGAA AGGUGGG |
| 1661 | 1302 | CAAAGGA CUGAUGAGGCCGAAAGGCCGAA AGGUUUC |
| 1663 | 1303 | UUCAAAG CUGAUGAGGCCGAAAGGCCGAA AAAGGUU |
| 1678 | 1304 | CCAGGCU CUGAUGAGGCCGAAAGGCCGAA AGGUCCU |
| 1680 | 1305 | CCAGAGG CUGAUGAGGCCGAAAGGCCGAA AGUGGCU |
| 1681 | 1306 | GCCAGAG CUGAUGAGGCCGAAAGGCCGAA AAGUGGC |
| 1684 | 1307 | ACAGCCA CUGAUGAGGCCGAAAGGCCGAA AGGAAGU |
| 1690 | 1308 | AGAUCGA CUGAUGAGGCCGAAAGGCCGAA AGUCCGG |
| 1691 | 1309 | AAGAUCG CUGAUGAGGCCGAAAGGCCGAA AAGUCCG |
| 1696 | 1310 | CCACCCC CUGAUGAGGCCGAAAGGCCGAA AUGGGCA |
| 1698 | 1311 | CUCCAGG CUGAUGAGGCCGAAAGGCCGAA AUAUCCG |
| 1737 | 1312 | GCUGGUA CUGAUGAGGCCGAAAGGCCGAA AGGUCUC |
| 1750 | 1313 | UGAGGUG CUGAUGAGGCCGAAAGGCCGAA AGCCGCC |
| 1756 | 1314 | GGGCAGG CUGAUGAGGCCGAAAGGCCGAA AGGCUUC |
| 1787 | 1315 | UGGGGAC CUGAUGAGGCCGAAAGGCCGAA AUGUCUC |
| 1790 | 1316 | AUUAGAG CUGAUGAGGCCGAAAGGCCGAA ACAAUGC |
| 1793 | 1317 | UCCAGCC CUGAUGAGGCCGAAAGGCCGAA AGGACCA |
| 1797 | 1318 | UUUAUGU CUGAUGAGGCCGAAAGGCCGAA ACUGGUG |
| 1802 | 1319 | UCUCCAG CUGAUGAGGCCGAAAGGCCGAA AUCUGGU |
| 1812 | 1320 | GGCCUGA CUGAUGAGGCCGAAAGGCCGAA AUCCAGU |
| 1813 | 1321 | UGAGGGU CUGAUGAGGCCGAAAGGCCGAA AAUGCUG |
| 1825 | 1322 | GCAGAGG CUGAUGAGGCCGAAAGGCCGAA AGCGUGG |
| 1837 | 1323 | GGAGCUA CUGAUGAGGCCGAAAGGCCGAA AGGCAUG |
| 1845 | 1324 | GGUGGCC CUGAUGAGGCCGAAAGGCCGAA AGGCUCG |
| 1856 | 1325 | AAGAUCG CUGAUGAGGCCGAAAGGCCGAA AAGUCCG |
| 1861 | 1326 | UACUGGA CUGAUGAGGCCGAAAGGCCGAA AUCAUGU |
| 1865 | 1327 | CUGAGGC CUGAUGAGGCCGAAAGGCCGAA ACAAGUG |
| 1868 | 1328 | UUUAUGU CUGAUGAGGCCGAAAGGCCGAA ACUGGUG |
| 1877 | 1329 | AGCUGCU CUGAUGAGGCCGAAAGGCCGAA AGGCAUG |
| 1901 | 1330 | GUCCCUU CUGAUGAGGCCGAAAGGCCGAA AGUUUUA |
| 1912 | 1331 | ACUGAUC CUGAUGAGGCCGAAAGGCCGAA ACUAUAU |

43

| 1922 | 1332 | UAACUUA CUGAUGAGGCCGAAAGGCCGAA ACAUUCA |
|------|------|----------------------------------------|
| 1923 | 1333 | GAUACCU CUGAUGAGGCCGAAAGGCCGAA AGCAUCA |
| 1928 | 1334 | CUGGUAA CUGAUGAGGCCGAAAGGCCGAA ACUCUAA |
| 1930 | 1335 | AGCUGGU CUGAUGAGGCCGAAAGGCCGAA AAACUCU |
| 1964 | 1336 | UGGGGAC CUGAUGAGGCCGAAAGGCCGAA AUGUCUC |
| 1983 | 1337 | UAACUUG CUGAUGAGGCCGAAAGGCCGAA AUAUCCU |
| 1996 | 1338 | GGCUCAG CUGAUGAGGCCGAAAGGCCGAA AUCUCCU |
| 2005 | 1339 | GGUCCGC CUGAUGAGGCCGAAAGGCCGAA AGCUCCA |
| 2013 | 1340 | UACUCAA CUGAUGAGGCCGAAAGGCCGAA AAAUAGC |
| 2015 | 1341 | CCACCCC CUGAUGAGGCCGAAAGGCCGAA AUGGGCA |
| 2020 | 1342 | CUCAGAA CUGAUGAGGCCGAAAGGCCGAA AACCACC |
| 2039 | 1343 | CCUCUGC CUGAUGAGGCCGAAAGGCCGAA AGCCAGC |
| 2040 | 1344 | CCUCCAG CUGAUGAGGCCGAAAGGCCGAA AGGUCAG |
| 2057 | 1345 | GGAUGUG CUGAUGAGGCCGAAAGGCCGAA AGGAGCA |
| 2061 | 1346 | ACACGGU CUGAUGAGGCCGAAAGGCCGAA AUGGUAG |
| 2071 | 1347 | CUGAGGC CUGAUGAGGCCGAAAGGCCGAA ACAAGUG |
| 2076 | 1348 | UAGCUCU CUGAUGAGGCCGAAAGGCCGAA AGGCUAC |
| 2097 | 1349 | CAUCAAG CUGAUGAGGCCGAAAGGCCGAA AGAGUUG |
| 2098 | 1350 | CGGGGGG CUGAUGAGGCCGAAAGGCCGAA AAGUGUG |
| 2115 | 1351 | AUCCUCC CUGAUGAGGCCGAAAGGCCGAA AGCUGGC |
| 2128 | 1352 | CUCAAUA CUGAUGAGGCCGAAAGGCCGAA AUAGCUG |
| 2130 | 1353 | GAGGCAG CUGAUGAGGCCGAAAGGCCGAA AAACAGG |
| 2145 | 1354 | CAUCAAG CUGAUGAGGCCGAAAGGCCGAA AGAGUUG |
| 2152 | 1355 | AACUCUA CUGAUGAGGCCGAAAGGCCGAA AUUAAUA |
| 2156 | 1356 | UAAUAAA CUGAUGAGGCCGAAAGGCCGAA ACAUCAA |
| 2158 | 1357 | AUUAAUA CUGAUGAGGCCGAAAGGCCGAA AUACAUC |
| 2159 | 1358 | AAUUAAU CUGAUGAGGCCGAAAGGCCGAA AAUACAU |
| 2160 | 1359 | AAAUUAA CUGAUGAGGCCGAAAGGCCGAA AAAUACA |
| 2162 | 1360 | CUAAAUU CUGAUGAGGCCGAAAGGCCGAA AUAAAUA |
| 2163 | 1361 | AAUUAAU CUGAUGAGGCCGAAAGGCCGAA AAUACAU |
| 2166 | 1362 | AAUAGAG CUGAUGAGGCCGAAAGGCCGAA AUGAAGU |
| 2167 | 1363 | AAUUAAU CUGAUGAGGCCGAAAGGCCGAA AAUACAU |
| 2170 | 1364 | CUAAAUU CUGAUGAGGCCGAAAGGCCGAA AUAAAUA |
| 2171 | 1365 | GGGAGCA CUGAUGAGGCCGAAAGGCCGAA AACAACU |
| 2173 | 1366 | CUGGUAA CUGAUGAGGCCGAAAGGCCGAA ACUCUAA |
| 2174 | 1367 | GCUGGUA CUGAUGAGGCCGAAAGGCCGAA AACUCUA |
| 2175 | 1368 | AGCUGGU CUGAUGAGGCCGAAAGGCCGAA AAACUCU |
| 2176 | 1369 | UAGCUGG CUGAUGAGGCCGAAAGGCCGAA AAAACUC |
| 2183 | 1370 | CAAUAAA CUGAUGAGGCCGAAAGGCCGAA AGCUGGU |
| 2185 | 1371 | CUCAAUA CUGAUGAGGCCGAAAGGCCGAA AUAGCUG |
| 2186 | 1372 | ACUCAAU CUGAUGAGGCCGAAAGGCCGAA AAUAGCU |
| 2187 | 1373 | UACUCAA CUGAUGAGGCCGAAAGGCCGAA AAAUAGC |
| 2189 | 1374 | GGUACUC CUGAUGAGGCCGAAAGGCCGAA AUAAAUA |
| 2196 | 1375 | CAUCAAG CUGAUGAGGCCGAAAGGCCGAA AGAGUUG |
| 2198 | 1376 | AACAUAA CUGAUGAGGCCGAAAGGCCGAA AGGCUGC |
| 2199 | 1377 | AUAAACA CUGAUGAGGCCGAAAGGCCGAA AAGAGGC |
| 2200 | 1378 | CUUGCAU CUGAUGAGGCCGAAAGGCCGAA AGGAAGA |
| 2201 | 1379 | GCCGACA CUGAUGAGGCCGAAAGGCCGAA AAAACUU |

44

| | | |
|---|---|---|
| 2205 | 1380 | UCAGGCC CUGAUGAGGCCGAAAGGCCGAA ACAUAAA |
| 2210 | 1381 | AGCCACU CUGAUGAGGCCGAAAGGCCGAA AGUCUCC |
| 2220 | 1382 | AGAGAAC CUGAUGAGGCCGAAAGGCCGAA AUGCCAG |
| 2224 | 1383 | GGAUGGA CUGAUGAGGCCGAAAGGCCGAA ACCUGAG |
| 2226 | 1384 | GCGGCCU CUGAUGAGGCCGAAAGGCCGAA AGAUCCA |
| 2233 | 1385 | CCUCCAG CUGAUGAGGCCGAAAGGCCGAA AGGUCAG |
| 2242 | 1386 | GGUCCGC CUGAUGAGGCCGAAAGGCCGAA AGCUCCA |
| 2248 | 1387 | UGGGAUG CUGAUGAGGCCGAAAGGCCGAA AUGGAUA |
| 2254 | 1388 | UCAGUGU CUGAUGAGGCCGAAAGGCCGAA AAUUGGA |
| 2259 | 1389 | CACCGUG CUGAUGAGGCCGAAAGGCCGAA AUGUGAU |
| 2260 | 1390 | GCACCGU CUGAUGAGGCCGAAAGGCCGAA AAUGUGA |
| 2266 | 1391 | UCCUGGU CUGAUGAGGCCGAAAGGCCGAA ACAUUCC |
| 2274 | 1392 | UCUCCAG CUGAUGAGGCCGAAAGGCCGAA AUCUGGU |
| 2279 | 1393 | CUUGCAC CUGAUGAGGCCGAAAGGCCGAA ACCCUUC |
| 2282 | 1394 | CAGCUCA CUGAUGAGGCCGAAAGGCCGAA ACAGCUU |
| 2288 | 1395 | AGGCCAU CUGAUGAGGCCGAAAGGCCGAA ACUUAUA |
| 2291 | 1396 | AGCAGAG CUGAUGAGGCCGAAAGGCCGAA ACCACUG |
| 2321 | 1397 | CCCAUGU CUGAUGAGGCCGAAAGGCCGAA AUCUUUC |
| 2338 | 1398 | CAGGCAG CUGAUGAGGCCGAAAGGCCGAA AGUCUCA |
| 2339 | 1399 | CAAAGGA CUGAUGAGGCCGAAAGGCCGAA AGGUUUC |
| 2341 | 1400 | AGGCUGG CUGAUGAGGCCGAAAGGCCGAA AGAGGUC |
| 2344 | 1401 | GCUGGAA CUGAUGAGGCCGAAAGGCCGAA AUCGAAA |
| 2358 | 1402 | CUGCUGA CUGAUGAGGCCGAAAGGCCGAA AGCUGGG |
| 2359 | 1403 | UCUGUUC CUGAUGAGGCCGAAAGGCCGAA AAAGCAG |
| 2360 | 1404 | UUCAAAG CUGAUGAGGCCGAAAGGCCGAA AAAGGUU |
| 2376 | 1405 | UCAGAAG CUGAUGAGGCCGAAAGGCCGAA ACCACCU |
| 2377 | 1406 | CUCAGAA CUGAUGAGGCCGAAAGGCCGAA AACCACC |
| 2378 | 1407 | CAGUAGA CUGAUGAGGCCGAAAGGCCGAA AAACCCU |
| 2379 | 1408 | CUUAUGA CUGAUGAGGCCGAAAGGCCGAA AAAAGCA |
| 2380 | 1409 | GCCGACA CUGAUGAGGCCGAAAGGCCGAA AAAACUU |
| 2382 | 1410 | GGGGCAA CUGAUGAGGCCGAAAGGCCGAA AGAGAAU |
| 2384 | 1411 | UUGUGUC CUGAUGAGGCCGAAAGGCCGAA ACUGGAU |
| 2399 | 1412 | GUCCACA CUGAUGAGGCCGAAAGGCCGAA AGUGUUU |
| 2401 | 1413 | CAGCUCA CUGAUGAGGCCGAAAGGCCGAA ACAGCUU |
| 2411 | 1414 | GCAUCCU CUGAUGAGGCCGAAAGGCCGAA ACCAGUA |
| 2417 | 1415 | ACGUAUG CUGAUGAGGCCGAAAGGCCGAA ACCAUUC |
| 2418 | 1416 | GGCCUGA CUGAUGAGGCCGAAAGGCCGAA AUCCAGU |
| 2425 | 1417 | AACCCUC CUGAUGAGGCCGAAAGGCCGAA ACCCAUG |
| 2426 | 1418 | AAACUCU CUGAUGAGGCCGAAAGGCCGAA AAUUAAU |
| 2433 | 1419 | GCUGGUA CUGAUGAGGCCGAAAGGCCGAA AACUCUA |
| 2434 | 1420 | AGCUGGU CUGAUGAGGCCGAAAGGCCGAA AAACUCU |
| 2448 | 1421 | GGGCAGG CUGAUGAGGCCGAAAGGCCGAA AGGCUUC |
| 2449 | 1422 | GGGGCAG CUGAUGAGGCCGAAAGGCCGAA AAGGCUU |
| 2451 | 1423 | AGGCAGG CUGAUGAGGCCGAAAGGCCGAA AACAGGC |
| 2452 | 1424 | GAGGCAG CUGAUGAGGCCGAAAGGCCGAA AAACAGG |
| 2455 | 1425 | GGGCAGG CUGAUGAGGCCGAAAGGCCGAA AGGCUUC |
| 2459 | 1426 | GGGGGGG CUGAUGAGGCCGAAAGGCCGAA AGUGUGG |
| 2460 | 1427 | CGGGGGG CUGAUGAGGCCGAAAGGCCGAA AAGUGUG |

| | | |
|---|---|---|
| 2479 | 1428 | GCUGGUA CUGAUGAGGCCGAAAGGCCGAA AGGUCUC |
| 2480 | 1429 | GGAUCAC CUGAUGAGGCCGAAAGGCCGAA ACGGUGA |
| 2483 | 1430 | GGUGGCU CUGAUGAGGCCGAAAGGCCGAA ACAUUGG |
| 2484 | 1431 | GACUGGU CUGAUGAGGCCGAAAGGCCGAA AAAAAAG |
| 2492 | 1432 | AGGUGGG CUGAUGAGGCCGAAAGGCCGAA AGGUGCU |
| 2504 | 1433 | ACAAAAG CUGAUGAGGCCGAAAGGCCGAA AGGUGGG |
| 2508 | 1434 | UGGGAUG CUGAUGAGGCCGAAAGGCCGAA AUGGAUA |
| 2509 | 1435 | CUGGUAA CUGAUGAGGCCGAAAGGCCGAA ACUCUAA |
| 2510 | 1436 | GCUGGUA CUGAUGAGGCCGAAAGGCCGAA AACUCUA |
| 2520 | 1437 | CAUUGGG CUGAUGAGGCCGAAAGGCCGAA ACAAAAG |
| 2521 | 1438 | UGAGGGU CUGAUGAGGCCGAAAGGCCGAA AAUGCUG |
| 2533 | 1439 | GAUACCU CUGAUGAGGCCGAAAGGCCGAA AGCAUCA |
| 2540 | 1440 | CACAGCG CUGAUGAGGCCGAAAGGCCGAA ACUGCUG |
| 2545 | 1441 | AGGACCA CUGAUGAGGCCGAAAGGCCGAA ACAGCAC |
| 2568 | 1442 | UUUGACA CUGAUGAGGCCGAAAGGCCGAA ACUUCAC |
| 2579 | 1443 | CAGGCCA CUGAUGAGGCCGAAAGGCCGAA AACUUAU |
| 2585 | 1444 | AGAGAAC CUGAUGAGGCCGAAAGGCCGAA AUGCCAG |
| 2588 | 1445 | AUUAGAG CUGAUGAGGCCGAAAGGCCGAA ACAAUGC |
| 2591 | 1446 | AGGAGCA CUGAUGAGGCCGAAAGGCCGAA AGAACCA |
| 2593 | 1447 | GCAGAGC CUGAUGAGGCCGAAAGGCCGAA AAAGAAG |
| 2596 | 1448 | CAUUGGG CUGAUGAGGCCGAAAGGCCGAA ACAAAAG |
| 2601 | 1449 | AAACGAA CUGAUGAGGCCGAAAGGCCGAA ACACGGU |
| 2602 | 1450 | GGGAUGG CUGAUGAGGCCGAAAGGCCGAA AGCUGGA |
| 2607 | 1451 | CCAGGUA CUGAUGAGGCCGAAAGGCCGAA AUCCGAG |
| 2608 | 1452 | CACAGCG CUGAUGAGGCCGAAAGGCCGAA ACUGCUG |
| 2609 | 1453 | UCCUGGU CUGAUGAGGCCGAAAGGCCGAA ACAUUCC |
| 2620 | 1454 | GCAGGGU CUGAUGAGGCCGAAAGGCCGAA AGGUCCU |
| 2626 | 1455 | GCUGGAA CUGAUGAGGCCGAAAGGCCGAA AUCGAAA |
| 2628 | 1456 | AGGCUAC CUGAUGAGGCCGAAAGGCCGAA AGUGUGC |
| 2635 | 1457 | AGGACCG CUGAUGAGGCCGAAAGGCCGAA AGCUGAA |
| 2640 | 1458 | GGCAGGA CUGAUGAGGCCGAAAGGCCGAA ACAGGCC |
| 2641 | 1459 | CUGCUGA CUGAUGAGGCCGAAAGGCCGAA AGCUGGG |
| 2642 | 1460 | GAGGCAG CUGAUGAGGCCGAAAGGCCGAA AAACAGG |
| 2653 | 1461 | GCAUCCU CUGAUGAGGCCGAAAGGCCGAA ACCAGUA |
| 2659 | 1462 | CUUGCAC CUGAUGAGGCCGAAAGGCCGAA ACCCUUC |
| 2689 | 1463 | CCUCGGA CUGAUGAGGCCGAAAGGCCGAA ACAUUAG |
| 2691 | 1464 | GGCCUCG CUGAUGAGGCCGAAAGGCCGAA AGACAUU |
| 2700 | 1465 | GGGCAGG CUGAUGAGGCCGAAAGGCCGAA AGGCUUC |
| 2704 | 1466 | AGGCUGG CUGAUGAGGCCGAAAGGCCGAA AGAGGUC |
| 2711 | 1467 | CUGCUGA CUGAUGAGGCCGAAAGGCCGAA AGCUGGG |
| 2712 | 1468 | CCCUUCC CUGAUGAGGCCGAAAGGCCGAA AGACCUC |
| 2721 | 1469 | CUUGCAC CUGAUGAGGCCGAAAGGCCGAA ACCCUUC |
| 2724 | 1470 | GCACACG CUGAUGAGGCCGAAAGGCCGAA AUGUACC |
| 2744 | 1471 | CUGCACG CUGAUGAGGCCGAAAGGCCGAA ACCCACC |
| 2750 | 1472 | GGUACUC CUGAUGAGGCCGAAAGGCCGAA AUAAAUA |
| 2759 | 1473 | AGAUCGA CUGAUGAGGCCGAAAGGCCGAA AGUCCGG |
| 2761 | 1474 | GCAGGGU CUGAUGAGGCCGAAAGGCCGAA AGGUCCU |
| 2765 | 1475 | AGCGGCA CUGAUGAGGCCGAAAGGCCGAA AGCAAAA |

46

| | | |
|---|---|---|
| 2769 | 1476 | CCUGUUU CUGAUGAGGCCGAAAGGCCGAA ACAGACU |
| 2797 | 1477 | GGACCAU CUGAUGAGGCCGAAAGGCCGAA AUUUCAU |
| 2803 | 1478 | CGCCUGG CUGAUGAGGCCGAAAGGCCGAA ACCAUGA |
| 2804 | 1479 | CUGCACG CUGAUGAGGCCGAAAGGCCGAA ACCCACC |
| 2813 | 1480 | GGGUCAG CUGAUGAGGCCGAAAGGCCGAA ACCGGAG |
| 2815 | 1481 | AAAGUUG CUGAUGAGGCCGAAAGGCCGAA AGACUGU |
| 2821 | 1482 | CCUCCAG CUGAUGAGGCCGAAAGGCCGAA AGGUCAG |
| 2822 | 1483 | AAGUCCG CUGAUGAGGCCGAAAGGCCGAA AGGCUCC |
| 2823 | 1484 | UGGGAGC CUGAUGAGGCCGAAAGGCCGAA AAAGGCA |
| 2829 | 1485 | AUGAUUA CUGAUGAGGCCGAAAGGCCGAA AGUCCAG |
| 2837 | 1486 | UCAGAAG CUGAUGAGGCCGAAAGGCCGAA ACCACCU |
| 2840 | 1487 | CAGGCAG CUGAUGAGGCCGAAAGGCCGAA AGUCUCA |
| 2847 | 1488 | GGUGGCU CUGAUGAGGCCGAAAGGCCGAA ACAUUGG |
| 2853 | 1489 | AACAUAA CUGAUGAGGCCGAAAGGCCGAA AGGCUGC |
| 2860 | 1490 | UCACAGU CUGAUGAGGCCGAAAGGCCGAA ACUUGGC |
| 2872 | 1491 | CUUGGCU CUGAUGAGGCCGAAAGGCCGAA AAGGUCC |
| 2877 | 1492 | GUGAUGG CUGAUGAGGCCGAAAGGCCGAA AGCGGAA |
| 2899 | 1493 | AAGAUCG CUGAUGAGGCCGAAAGGCCGAA AAGUCCG |
| 2900 | 1494 | AAAACUC CUGAUGAGGCCGAAAGGCCGAA AAAUUAA |
| 2904 | 1495 | AAUAGAG CUGAUGAGGCCGAAAGGCCGAA AUGAAGU |
| 2905 | 1496 | CAAUAGA CUGAUGAGGCCGAAAGGCCGAA AAUGAAG |
| 2906 | 1497 | UAAUAAA CUGAUGAGGCCGAAAGGCCGAA ACAUCAA |
| 2907 | 1498 | AAAUUAA CUGAUGAGGCCGAAAGGCCGAA AAAUACA |
| 2908 | 1499 | AGCAAAA CUGAUGAGGCCGAAAGGCCGAA AAGCUUC |
| 2909 | 1500 | AGAGCAA CUGAUGAGGCCGAAAGGCCGAA AGAAGCU |
| 2910 | 1501 | AAAUUAA CUGAUGAGGCCGAAAGGCCGAA AAAUACA |
| 2911 | 1502 | AAAUUAA CUGAUGAGGCCGAAAGGCCGAA AAAUACA |
| 2912 | 1503 | GACAUUA CUGAUGAGGCCGAAAGGCCGAA AGAACAA |
| 2913 | 1504 | UGACCAG CUGAUGAGGCCGAAAGGCCGAA AGAGAAA |
| 2914 | 1505 | CUUAUGA CUGAUGAGGCCGAAAGGCCGAA AAAAGCA |
| 2915 | 1506 | UCUAAAU CUGAUGAGGCCGAAAGGCCGAA AAUAAAU |
| 2916 | 1507 | CUCCGGA CUGAUGAGGCCGAAAGGCCGAA ACGAAUA |
| 2917 | 1508 | UCUCCGG CUGAUGAGGCCGAAAGGCCGAA AACGAAU |
| 2918 | 1509 | CUCUCCG CUGAUGAGGCCGAAAGGCCGAA AAACGAA |
| 2919 | 1510 | CGACCCU CUGAUGAGGCCGAAAGGCCGAA AUGAGAA |
| 2931 | 1511 | CUUCCGA CUGAUGAGGCCGAAAGGCCGAA ACCUCCA |
| 2933 | 1512 | CCCUUCC CUGAUGAGGCCGAAAGGCCGAA AGACCUC |
| 2941 | 1513 | UGGGGAC CUGAUGAGGCCGAAAGGCCGAA AUGUCUC |
| 2951 | 1514 | GCAGAGG CUGAUGAGGCCGAAAGGCCGAA AGCGUGG |
| 2952 | 1515 | CACAGCG CUGAUGAGGCCGAAAGGCCGAA ACUGCUG |
| 2955 | 1516 | UGACACA CUGAUGAGGCCGAAAGGCCGAA AGUCACU |
| 2956 | 1517 | UUGAUUC CUGAUGAGGCCGAAAGGCCGAA AAGGAAA |
| 2961 | 1518 | AGUGGCU CUGAUGAGGCCGAAAGGCCGAA ACACAGA |
| 2962 | 1519 | AAUUAAU CUGAUGAGGCCGAAAGGCCGAA AAUACAU |
| 2965 | 1520 | CUUUAUU CUGAUGAGGCCGAAAGGCCGAA AUUCAAA |
| 2966 | 1521 | CCUCUGC CUGAUGAGGCCGAAAGGCCGAA AGCCAGC |
| 2969 | 1522 | AAAACUU CUGAUGAGGCCGAAAGGCCGAA AUUGAUU |
| 2975 | 1523 | GCUGGUA CUGAUGAGGCCGAAAGGCCGAA AACUCUA |

47

| 2976 | 1524 | AGUAGAG CUGAUGAGGCCGAAAGGCCGAA AACCCUC |
| --- | --- | --- |
| 2977 | 1525 | CAGCUCA CUGAUGAGGCCGAAAGGCCGAA ACAGCUU |
| 2979 | 1526 | GGCAAUA CUGAUGAGGCCGAAAGGCCGAA AGAAUGA |

Table VI

Human ICAM Hairpin Ribozyme/Substrate Sequences

| nt. Position | SEQ ID NO | Hairpin Ribozyme Sequence | SEQ ID NO | Substrate |
|---|---|---|---|---|
| 70 | 1527 | GGGCCGGG AGAA GCUG ACCAGAGAAACACGUUGUGUACAUUACCUGGUA | 1544 | CAGCA GCC CCCGGCCC |
| 86 | 1528 | GGAGUGCG AGAA GCGC ACCAGAGAAACACGUUGUGUACAUUACCUGGUA | 1545 | GCGCU GCC CGCACUCC |
| 343 | 1529 | CCCAUCAG AGAA GUUU ACCAGAGAAACACGUUGUGUACAUUACCUGGUA | 1546 | AAACU GCC CUGAUGGG |
| 635 | 1530 | GCCCUUGG AGAA GCAG ACCAGAGAAACACGUUGUGUACAUUACCUGGUA | 1547 | CUGCG GCC CCAAGGGC |
| 653 | 1531 | UGUUCUCA AGAA GCUC ACCAGAGAAACACGUUGUGUACAUUACCUGGUA | 1548 | GAGCU GUU UGAGAACA |
| 782 | 1532 | AGACUGGG AGAA GCCC ACCAGAGAAACACGUUGUGUACAUUACCUGGUA | 1549 | GGGCU GUU CCCAGUCU |
| 920 | 1533 | CUGCACAC AGAA GCCG ACCAGAGAAACACGUUGUGUACAUUACCUGGUA | 1550 | CGGCU GAC GUGUGCAG |
| 1301 | 1534 | ACAUUGGA AGAA GCUG ACCAGAGAAACACGUUGUGUACAUUACCUGGUA | 1551 | CAGCA GAC UCCAAUGU |
| 1373 | 1535 | CCCCGAUG AGAA GUGG ACCAGAGAAACACGUUGUGUACAUUACCUGGUA | 1552 | CCACU GCC CAUCGGGG |
| 1521 | 1536 | AUGACUGC AGAA GCUA ACCAGAGAAACACGUUGUGUACAUUACCUGGUA | 1553 | UAGCA GCC GCAGUCAU |
| 1594 | 1537 | CUGUUGUA AGAA GUAU ACCAGAGAAACACGUUGUGUACAUUACCUGGUA | 1554 | AUACA GAC UACAACAG |
| 2008 | 1538 | ACCCAAUA AGAA GCAA ACCAGAGAAACACGUUGUGUACAUUACCUGGUA | 1555 | UUGCU GCC UAUUGGGU |
| 2034 | 1539 | UUCUGUAA AGAA GUGG ACCAGAGAAACACGUUGUGUACAUUACCUGGUA | 1556 | CCACA GAC UUACAGAA |
| 2125 | 1540 | GGUCAGUA AGAA GCAG ACCAGAGAAACACGUUGUGUACAUUACCUGGUA | 1557 | CUGCU GUC UACUGACC |
| 2132 | 1541 | GGGUUGGG AGAA GUAG ACCAGAGAAACACGUUGUGUACAUUACCUGGUA | 1558 | CUACU GAC CCCAACCC |
| 2276 | 1542 | ACCUGAAC AGAA GUAC ACCAGAGAAACACGUUGUGUACAUUACCUGGUA | 1559 | GUACA GUU GUACAGGU |
| 2810 | 1543 | AAGGUCAA AGAA GCAC ACCAGAGAAACACGUUGUGUACAUUACCUGGUA | 1560 | CUGCA GUC UUGACCUU |

Table VII

Mouse ICAM Hairpin Ribozyme/Substrate Sequences

| nt. Position | SEQ ID NO | Hairpin Ribozyme Sequence | SEQ ID NO | Substrate |
|---|---|---|---|---|
| 76 | 1561 | GGGAUCAC AGAA GUGA ACCAGAGAAACACGUUGUGUACAUUACCUGGUA | 1578 | UCACC GUU GUGAUCCC |
| 164 | 1562 | UGAGGAAG AGAA GUUC ACCAGAGAAACACGUUGUGUACAUUACCUGGUA | 1579 | GAACU GUU CUUCCUCA |
| 252 | 1563 | UCAGCUCA AGAA GCUU ACCAGAGAAACACGUUGUGUACAUUACCUGGUA | 1580 | AAGCU GUU UGAGCUGA |
| 284 | 1564 | GCACAGCG AGAA GCUG ACCAGAGAAACACGUUGUGUACAUUACCUGGUA | 1581 | CAGCA GUC CGCUGUGC |
| 318 | 1565 | AAGCGGAC AGAA GCAC ACCAGAGAAACACGUUGUGUACAUUACCUGGUA | 1582 | GUGCA GUC GUCCGCUU |
| 447 | 1566 | AGAGCUGG AGAA GCGG ACCAGAGAAACACGUUGUGUACAUUACCUGGUA | 1583 | CCGCG GAC CCAGCUCU |
| 804 | 1567 | UCUCCUGG AGAA GCAU ACCAGAGAAACACGUUGUGUACAUUACCUGGUA | 1584 | AUGCC GAC CCAGGAGA |
| 847 | 1568 | UCUACCAA AGAA GUGG ACCAGAGAAACACGUUGUGUACAUUACCUGGUA | 1585 | CCACU GCC UUGGUAGA |
| 913 | 1569 | AGGAUCUG AGAA GCUA ACCAGAGAAACACGUUGUGUACAUUACCUGGUA | 1586 | UAGCG GAC CAGAUCCU |
| 946 | 1570 | AAGUUGUA AGAA GUUA ACCAGAGAAACACGUUGUGUACAUUACCUGGUA | 1587 | UAACA GUC UACAACUU |
| 1234 | 1571 | CCCAAGCA AGAA GUCU ACCAGAGAAACACGUUGUGUACAUUACCUGGUA | 1588 | AGACG GAC UGCUUGGG |
| 1275 | 1572 | AUUUCAGA AGAA GCUG ACCAGAGAAACACGUUGUGUACAUUACCUGGUA | 1589 | CAGCA GAC UCUGAAAU |
| 1325 | 1573 | UGCCUUCC AGAA GCAG ACCAGAGAAACACGUUGUGUACAUUACCUGGUA | 1590 | CUGCA GAC GGAAGGCA |
| 1350 | 1574 | CCCCGAUG AGAA GCAG ACCAGAGAAACACGUUGUGUACAUUACCUGGUA | 1591 | CUGCU GCC CAUCGGGG |
| 1534 | 1575 | ACAUAAGA AGAA GCCA ACCAGAGAAACACGUUGUGUACAUUACCUGGUA | 1592 | UGGCA GCC UCUUAUGU |
| 1851 | 1576 | GUCCACCG AGAA GUAG ACCAGAGAAACACGUUGUGUACAUUACCUGGUA | 1593 | CUACA GCC CGGUGGAC |
| 1880 | 1577 | AGAAUGAA AGAA GCGU ACCAGAGAAACACGUUGUGUACAUUACCUGGUA | 1594 | ACGCU GAC UUCAUUCU |

Table VIII

Rat ICAM Hairpin Ribozyme/Substrate Sequences

| nt. Position | SEQ ID NO | Hairpin Ribozyme Sequence | SEQ ID NO | Substrate |
|---|---|---|---|---|
| 5 | 1595 | AAGUGCA AGAA GCAG ACCAGAGAAACACGUUGUGGUACAUUACCUGGUA | 1614 | CUGCU GCC UGCACUUU |
| 59 | 1596 | GGAGCAGA AGAA GCAU ACCAGAGAAACACGUUGUGGUACAUUACCUGGUA | 1615 | AUGCU GCC UCUGCUCC |
| 84 | 1597 | GGGAUCAC AGAA GCGA ACCAGAGAAACACGUUGUGGUACAUUACCUGGUA | 1616 | UCGCC GUU GUGAUCCC |
| 295 | 1598 | GCACAGUG AGAA GCUG ACCAGAGAAACACGUUGUGGUACAUUACCUGGUA | 1617 | CAGCA GAC CACUGUGC |
| 329 | 1599 | AAGCCGAG AGAA GCGU ACCAGAGAAACACGUUGUGGUACAUUACCUGGUA | 1618 | ACGCA GUC CUCGGCUU |
| 433 | 1600 | UUCCACCA AGAA GCGC ACCAGAGAAACACGUUGUGGUACAUUACCUGGUA | 1619 | GCGCU GCC UGGUGGAA |
| 626 | 1601 | CAUUCUUG AGAA GUGA ACCAGAGAAACACGUUGUGGUACAUUACCUGGUA | 1620 | UCACU GUU CAAGAAUG |
| 806 | 1602 | UCUCCAGG AGAA GCAU ACCAGAGAAACACGUUGUGGUACAUUACCUGGUA | 1621 | AUGCU GAC CCUGGAGA |
| 849 | 1603 | UCCACUGA AGAA GUGG ACCAGAGAAACACGUUGUGGUACAUUACCUGGUA | 1622 | CCACU GCC UCAGUGGA |
| 915 | 1604 | AGGGUCUG AGAA GCCA ACCAGAGAAACACGUUGUGGUACAUUACCUGGUA | 1623 | UGGCG GAC CAGACCCU |
| 1182 | 1605 | ACCUCCAA AGAA GCAG ACCAGAGAAACACGUUGUGGUACAUUACCUGGUA | 1624 | CUGCG GCC UUGGAGGU |
| 1307 | 1606 | AUGUAAGA AGAA GCUG ACCAGAGAAACACGUUGUGGUACAUUACCUGGUA | 1625 | CAGCA GAC UCUUACAU |
| 1357 | 1607 | UGCUUUCC AGAA GCAG ACCAGAGAAACACGUUGUGGUACAUUACCUGGUA | 1626 | CUGCA GCC GGAAAGCA |
| 1382 | 1608 | UCCCGAUA AGAA GCGG ACCAGAGAAACACGUUGUGGUACAUUACCUGGUA | 1627 | CCGCU GCC UAUCGGGA |
| 1858 | 1609 | GCCACCA AGAA GUAG ACCAGAGAAACACGUUGUGGUACAUUACCUGGUA | 1628 | CUACA GCC UGGUGGGC |
| 1887 | 1610 | AGAAGGAA AGAA GCCU ACCAGAGAAACACGUUGUGGUACAUUACCUGGUA | 1629 | AGGCU GAC UUCCUUCU |
| 2012 | 1611 | GAGUUGGG AGAA GUGU ACCAGAGAAACACGUUGUGGUACAUUACCUGGUA | 1630 | ACACU GUC CCCAACUC |
| 2303 | 1612 | AGACUCCA AGAA GUGG ACCAGAGAAACACGUUGUGGUACAUUACCUGGUA | 1631 | CCACA GCC UGGAGUCU |
| 2539 | 1613 | CCUCCCAC AGAA GCUU ACCAGAGAAACACGUUGUGGUACAUUACCUGGUA | 1632 | AAGCU GUU GUGGGAGG |

51

Table IX: Rat ICAM HH Ribozyme Target Sequence

| nt. Position | SEQ ID NO | HH Target sequence | nt. Position | SEQ ID NO | HH Target Sequence |
|---|---|---|---|---|---|
| 11 | 1633 | GAUCCAAU U CACACUGA | 394 | 1674 | GUGGUGCU U CUGAACAG |
| 23 | 1634 | GCUGACUU C CUUCUCUA | 420 | 1675 | GCACCCCU C CCAGCGCA |
| 26 | 1635 | GAACUGCU C UUCCUCUU | 425 | 1676 | CCUCGGCU U CUGCCACC |
| 31 | 1636 | CCUCUGCU C CUGGUCCU | 427 | 1677 | UCCCUGUU U AAAAACCA |
| 34 | 1637 | CUGAAGCU C AGAUAUAC | 450 | 1678 | AAGAACCU U AUCCUGCG |
| 40 | 1638 | CUCAAGGU A CAAGCCCC | 451 | 1679 | GGGUACUU C CCCCAGGC |
| 48 | 1639 | GAGAACCU C GGCCUGGG | 456 | 1680 | CUCGGCU C UGCCACCA |
| 54 | 1640 | CCCCGCCU C CCUGAGCC | 495 | 1681 | GCCACCAU C ACUGUGUA |
| 58 | 1641 | CCGUGCCU U UAGCUCCC | 510 | 1682 | GUGCUGCU C CGUGGGAA |
| 64 | 1642 | CAAUGGCU U CAACCCGU | 564 | 1683 | GAAAAUGU U CCAACCAC |
| 96 | 1643 | CCUCUGCU C CUGGUCCU | 592 | 1684 | GGGAGUAU C ACCAGGGA |
| 102 | 1644 | CUCCUGGU C CUGGUCGC | 607 | 1685 | GAGCCAAU U UCUCAUGC |
| 108 | 1645 | GGACUGCU U GGGGAACU | 608 | 1686 | AGCCAAUU U CUCAUGCU |
| 115 | 1646 | UCCUACCU U UGUUCCCA | 609 | 1687 | GCCAAUUU C UCAUGCUU |
| 119 | 1647 | GACACUGU C CCCAACUC | 611 | 1688 | CAAUUUCU C AUGCUUCA |
| 120 | 1648 | GUUGUGAU C CCCGGGCC | 656 | 1689 | GUCACUGU U CAAGAAUG |
| 146 | 1649 | CCAGACCU U GGAACUCC | 657 | 1690 | UCACUGUU A AGAAUGU |
| 152 | 1650 | ACCCGGCU C CACCUCAA | 668 | 1691 | GAACUGCU U UUCCUCUU |
| 158 | 1651 | AUUUCUUU C ACGAGUCA | 677 | 1692 | GCACCCCU C CCAGCGCA |
| 165 | 1652 | UGAACAGU A CUUCCCCC | 684 | 1693 | AGGCAGCC C CGGACUUU |
| 168 | 1653 | GAAGCCUU C CUGCCUCG | 692 | 1694 | CCAGACCU U GGAACUCC |
| 185 | 1654 | GGGUGGAU C CGUGCAGG | 693 | 1695 | CGGACUUU C GAUCUUCC |
| 209 | 1655 | CAGCCCCU A AUCUGACC | 696 | 1696 | GCCUGUUU C CUGCCUCU |
| 227 | 1656 | GACCAAGU A ACUGUGAA | 709 | 1697 | CAGCAUUU A CCCCUCAC |
| 230 | 1657 | CAAGCUGU U GUGGGAGG | 720 | 1698 | CUACAACU U UUCAGCUC |
| 237 | 1658 | CUGAAGCU C GACACCCC | 723 | 1699 | CAACUUUU C AGCUCCCA |
| 248 | 1659 | GGCCCCCU A CCUUAGGA | 735 | 1700 | CUCCUGGU C CUGGUCGC |
| 253 | 1660 | CACUGCCU C AGUGGAGG | 738 | 1701 | UCCUGCCU C GGGGUGGA |
| 263 | 1661 | GAGCCAAU U UCUCAUGC | 765 | 1702 | ACUGUGCU U UGAGAACU |
| 267 | 1662 | GAAGCCUU C CUGCCUCG | 769 | 1703 | UCUUGUGU U CCCUGGAA |
| 293 | 1663 | GAAGCUCU U CAAGCUGA | 770 | 1704 | CUUGUGUU C CUGGAAG |
| 319 | 1664 | CGGAGGAU C ACAAACGA | 785 | 1705 | AGGCCUGU U UCCUGCCU |
| 335 | 1665 | ACUGUGCU U UGAGAACU | 786 | 1706 | GGCCUGUU U CCUGCCUC |
| 337 | 1666 | UGUGCUAU A UGGUCCUC | 792 | 1707 | CUCCUGGU C CUGGUCGC |
| 338 | 1667 | AAGCUCUU C AAGCUGAG | 794 | 1708 | UCCUGCCU U UGAAGCUC |
| 359 | 1668 | CACGCAGU C CUCGGCUU | 807 | 1709 | GCUCAGAU A UACCUGGA |
| 367 | 1669 | CAAUGGCU U CAACCCGU | 833 | 1710 | CCUGGGGU U GGAGACUA |
| 374 | 1670 | UUACCCCU C ACCCACCU | 846 | 1711 | CUGACAGU U AUUUAUUG |
| 375 | 1671 | AGAAGCCU U CCUGCCUC | 851 | 1712 | GCUCACCU U UAGCAGCU |
| 378 | 1672 | ACCCACCU C ACAGGGUA | 863 | 1713 | CAAUGGCU U CAACCCGU |

52

| | | | | | |
|---|---|---|---|---|---|
| 386 | 1673 | CGCUGUGU U UUGGAGCU | 866 | 1714 | CCAUGCUU C CUCUGACA |
| 867 | 1715 | GACCACCU C CCCACCUA | 1421 | 1764 | GGGUACUU C CCCCAGGC |
| 869 | 1716 | CUCUUCCU C UUGCGAAG | 1425 | 1765 | ACCCACCU C CUCUGGCU |
| 881 | 1717 | AAUGGCUU C AACCCGUG | 1429 | 1766 | AUACUUGU A GCCUCAGG |
| 885 | 1718 | GACCAAGU A ACUGUGAA | 1444 | 1767 | AGAAGGCU C AGGAGGAG |
| 933 | 1719 | UGUGUAUU C GUUCCCAG | 1455 | 1768 | GGGAGUAU C ACCAGGGA |
| 936 | 1720 | GCAGAGAU U UUGUGUCA | 1482 | 1769 | AGGGUACU U CCCCCAGG |
| 978 | 1721 | UUGAGAAU C UACAACUU | 1484 | 1770 | ACUGCUCU U CCUCUUGC |
| 980 | 1722 | GAGAAUCU A CAACUUUU | 1493 | 1771 | CCUGGGGU U GGAGACUA |
| 986 | 1723 | CUACAACU U UUCAGCUC | 1500 | 1772 | CGUGAAAU U AUGGUCAA |
| 987 | 1724 | UACAACUU U UCAGCUCC | 1503 | 1773 | GAAAAUGU U CCAACCAC |
| 988 | 1725 | ACAACUUU U CAGCUCCC | 1506 | 1774 | UGGGUCAA A AUUGUUGG |
| 1005 | 1726 | UUCGUGAU C GUGGCGUC | 1509 | 1775 | GCCACCAU C ACUGUGUA |
| 1006 | 1727 | GUGGGAGU A UCACCAGG | 1518 | 1776 | GUCCUGGU C GCCGUUGU |
| 1023 | 1728 | CCGGAGGU C UCAGAAGG | 1530 | 1777 | ACCUGGGU C AUAAUUGU |
| 1025 | 1729 | GGAGGUCU C AGAAGGGG | 1533 | 1778 | CUGAUCAU U GCGGGCUU |
| 1066 | 1730 | CCUACCUU U GUUCCCAA | 1551 | 1779 | GUGGCCCU C UGCUCGUA |
| 1092 | 1731 | AGAGGGGU C UCAGCAGA | 1559 | 1780 | UGGGAAGU C CCUGUUUA |
| 1093 | 1732 | AGGGGAAU C CAGCCCCU | 1563 | 1781 | UCCUACCU U UGUUCCCA |
| 1125 | 1733 | CCCCAACU C UUGUUGAU | 1565 | 1782 | UUACACCU A UUACCGCC |
| 1163 | 1734 | ACGACGCU U CUUUUGCU | 1567 | 1783 | ACACCUAU U ACCGCCAG |
| 1164 | 1735 | CGACGCUU C UUUUGCUC | 1584 | 1784 | AGGAAGAU A AGGAUAUA |
| 1166 | 1736 | ACGCUUCU U UUGCUCUG | 1592 | 1785 | CAGGAUAU A CAAGUUAC |
| 1172 | 1737 | CUUUUGCU C UGCGGCCU | 1599 | 1786 | UACAAGUU A CAGAAGGC |
| 1200 | 1738 | AUCCAAUU C ACACUGAA | 1651 | 1787 | CCCCGCCU C CCUGAGCC |
| 1201 | 1739 | UUGGGCUU C UCCACAGG | 1661 | 1788 | CUGCACUU U GCCCUGGU |
| 1203 | 1740 | GGGCUUCU C CACAGGUC | 1663 | 1789 | GAACAGAU C AAUGGACA |
| 1227 | 1741 | UUGGAACU C CAUGUGCU | 1678 | 1790 | GAGAACCU C GGCCUGGG |
| 1228 | 1742 | GCGGGCUU C GUGAUCGU | 1680 | 1791 | GGGCUUCU C CACAGGUC |
| 1233 | 1743 | CUCCUGGU C CUGGUCGC | 1681 | 1792 | GGCCUGUU U CCUGCCUC |
| 1238 | 1744 | UGUGCUAU A UGGUCCUC | 1684 | 1793 | CUGCUCGU A GACCUCUC |
| 1264 | 1745 | GGAAAGAU C AUACGGGU | 1690 | 1794 | CCCCACCU A CAUACAUU |
| 1267 | 1746 | GUCACUGU U CAAGAAUG | 1691 | 1795 | CCGGACUU U CGAUCUUC |
| 1294 | 1747 | CAGAGAUU U UGUGUCAG | 1696 | 1796 | CUCCUGGU C CUGGUCGC |
| 1295 | 1748 | AGAGGGGU C UCAGCAGA | 1698 | 1797 | UCAGAUAU A CCUGGAGA |
| 1306 | 1749 | AGCAGACU C UUACAUGC | 1737 | 1798 | GAUCACAU U CACGGUGC |
| 1321 | 1750 | AACAGAGU C UGGGGAAA | 1750 | 1799 | GUCCAUUU A CACCUAUU |
| 1334 | 1751 | GUAUUCGU U CCCAGAGC | 1756 | 1800 | CCUCUGCU C CUGGUCCU |
| 1344 | 1752 | UCGGUGCU C AGGUAUCC | 1787 | 1801 | GAGAACCU C GGCCUGGG |
| 1351 | 1753 | UCAGGCCU A AGAGGACU | 1790 | 1802 | GACACUGU C CCCAACUC |
| 1353 | 1754 | UAGCAGCU C AACAAUGG | 1793 | 1803 | AUGGUCCU C ACCUGGAC |
| 1366 | 1755 | AGGGUACU U CCCCCAGG | 1797 | 1804 | UCCCUGUU U AAAAACCA |
| 1367 | 1756 | GGGUACUU C CCCCAGGC | 1802 | 1805 | GCUCAGAU A UACCUGGA |
| 1368 | 1757 | GAUGGUGU C CCGCUGCC | 1812 | 1806 | AACAGAGU C UGGGGAAA |
| 1380 | 1758 | CUGCCUAU C GGGAUGGU | 1813 | 1807 | GCGGGCUU C GUGAUCGU |
| 1388 | 1759 | UGGAGACU A ACUGGAUG | 1825 | 1808 | GCCACCAU C ACUGUGUA |
| 1398 | 1760 | CUGGCUGU C ACAGGACA | 1837 | 1809 | ACCCACCU C ACAGGGUA |

53

| | | | | | |
|---|---|---|---|---|---|
| 1402 | 1761 | CUGUGCUU U GAGAACUG | 1845 | 1810 | AGAGGACU C GGAGGGGC |
| 1408 | 1762 | UUCGUGAU C GUGGCGUC | 1856 | 1811 | CCCCUAAU C UGACCUGC |
| 1410 | 1763 | CGAACUAU C GAGUGGAC | 1861 | 1812 | CAUGUGCU A UAUGGUCC |
| 1865 | 1813 | UAUCCGGU A GACACAAG | 2198 | 1862 | GAAUGUCU C CGAGGUCA |
| 1868 | 1814 | UCACGAGU C AUAUAAAU | 2199 | 1863 | AGACUCUU A CAUGCCAG |
| 1877 | 1815 | ACAGUACU U CCCCCAGG | 2200 | 1864 | GGGUACUU C CCCCAGGC |
| 1901 | 1816 | CUAAAACU C AAGGUACA | 2201 | 1865 | GGGCUUCU C CACAGGUC |
| 1912 | 1817 | GAACAGAU C AAUGGACA | 2205 | 1866 | UUUUGUGU A AGCCACUG |
| 1922 | 1818 | AUGUAAGU U AUUGCCUA | 2210 | 1867 | UGGAGACU A ACUGGAUG |
| 1923 | 1819 | UGGACGCU C ACCUUUAG | 2220 | 1868 | GAGAACCU C GGCCUGGG |
| 1928 | 1820 | GCUCAGAU A UACCUGGA | 2224 | 1869 | ACAUACU U CCUACCUU |
| 1930 | 1821 | UGGAGACU A ACUGGAUG | 2226 | 1870 | CUGGACCU C AGGCCACA |
| 1964 | 1822 | AGAGAUUU U GUGUCAGC | 2233 | 1871 | UCAUGCUU C ACAGAACU |
| 1983 | 1823 | GAGAACCU C GGCCUGGG | 2242 | 1872 | ACACAGCU C UCAGUAGU |
| 1996 | 1824 | UGGAAGCU C UUCAAGCU | 2248 | 1873 | CUCCUGGU C CUGGUCGC |
| 2005 | 1825 | AUGUAAGU U AUUGCCUA | 2254 | 1874 | AUCCAAUU C ACACUGAA |
| 2013 | 1826 | CGCUGCCU A UCGGGAUG | 2259 | 1875 | GAUCACAU U CACGGUGC |
| 2015 | 1827 | CUGCCUAU C GGGAUGGU | 2260 | 1876 | AUCACACU A ACGGUGCU |
| 2020 | 1828 | UAUUGAGU A CCCUGUAC | 2266 | 1877 | AUCAGGAU A UACAAGUU |
| 2039 | 1829 | CGGAGGAU C ACAAACGA | 2274 | 1878 | GAGCAGGU U AACAUGUA |
| 2040 | 1830 | CCUGACCU C CUGGAGGU | 2279 | 1879 | GGAAAGAU C AUACGGGU |
| 2057 | 1831 | CUGGUCCU C CAAUGGCU | 2282 | 1880 | ACAGUUAU U UAUUGAGU |
| 2061 | 1832 | GCGUCCAU U UACACCUA | 2288 | 1881 | GCCCUGGU C CUCCAAUG |
| 2071 | 1833 | AUACUUGU A GCCUCAGG | 2291 | 1882 | CAGGAUAU A CAAGUUAC |
| 2076 | 1834 | UGUAGCCU C AGGCCUAA | 2321 | 1883 | GGAAAGAU C AUACGGGU |
| 2097 | 1835 | CCAACUCU U GUUGAUGU | 2338 | 1884 | UUGGGCUU C UCCACAGG |
| 2098 | 1836 | CCUGACCU C CUGGAGGU | 2339 | 1885 | GGGUACUU C CCCCAGGC |
| 2115 | 1837 | UUCCGACU A GGGUCCUG | 2341 | 1886 | GGGCCUGU C GGUGCUCA |
| 2128 | 1838 | AGUCUGU A CCAUGAUC | 2344 | 1887 | CUGCUCGU A GACCUCUC |
| 2130 | 1839 | GCCUGUUU C CUGCCUCU | 2358 | 1888 | CCCUGCCU C CUCCCACA |
| 2145 | 1840 | CCAACUCU U GUUGAUGU | 2359 | 1889 | CCAUCCAU C CCACAGAA |
| 2152 | 1841 | UUGAGAAU C UACAACUU | 2360 | 1890 | CUUGUGUU C CUGGAAG |
| 2156 | 1842 | UGACAGUU A UUUAUUGA | 2376 | 1891 | GAACUGCU U UUCCUCUU |
| 2158 | 1843 | UGAUGUAU U UAUUAAUU | 2377 | 1892 | GACUUCCU U CUCUAUUA |
| 2159 | 1844 | GAUGUAUU U AUUAAUUC | 2378 | 1893 | GCUGAUUU U UUCACGA |
| 2160 | 1845 | AUGUAUUU A UUAAUUCA | 2379 | 1894 | CUGCUCUU U CUCUUGCG |
| 2162 | 1846 | ACAUUCCU A CCUUUGUU | 2380 | 1895 | UGAUUUCU U UCACGAGU |
| 2163 | 1847 | UAUUUAUU A AUUCAGAG | 2382 | 1896 | AUUUCUUU C ACGAGUCA |
| 2166 | 1848 | UGAUGUAU U UAUUAAUU | 2384 | 1897 | UAUCCGGU A GACACAAG |
| 2167 | 1849 | GAUGUAUU U AUUAAUUC | 2399 | 1898 | UAAAUACU A UGUGGACG |
| 2170 | 1850 | GUAUUUAU U AAUUCAGA | 2401 | 1899 | UGUGCUAU A UGGCCUC |
| 2171 | 1851 | CAGUUAUU U AUUGAGUA | 2411 | 1900 | CAAUUUCU C AUGCUUCA |
| 2173 | 1852 | UGUGCUAU A UGGCCUC | 2417 | 1901 | AUCAGGAU A UACAAGUU |
| 2174 | 1853 | UCUCUAUU A CCCCUGCU | 2418 | 1902 | UCAUGCUU C ACAGAACU |
| 2175 | 1854 | AUUUCUUU C ACGAGUCA | 2425 | 1903 | UUAUUAAU U CAGAGUUC |
| 2176 | 1855 | GAAAAUGU U CCAACCAC | 2426 | 1904 | CCUGGGGU U GGAGACUA |
| 2183 | 1856 | UGACAGUU A UUUAUUGA | 2433 | 1905 | UCAGAGUU C UGACAGUU |

54

| | | | | | | |
|---|---|---|---|---|---|---|
| 2185 | 1857 | ACAGUUAU U UAUUGAGU | 2434 | 1906 | CGGAGGAU C ACAAACGA |
| 2186 | 1858 | CAGUUAUU U AUUGAGUA | 2448 | 1907 | UGAACAGU A CUUCCCCC |
| 2187 | 1859 | AGUUAUUU A UUGAGUAC | 2449 | 1908 | GAAGCCUU C CUGCCUCG |
| 2189 | 1860 | UUAUUUAU U GAGUACCC | 2451 | 1909 | GGCCUGUU U CCUGCCUC |
| 2196 | 1861 | CUGACAGU U AUUUAUUG | 2452 | 1910 | GCCUGUUU C CUGCCUCU |
| 2455 | 1911 | ACAUUCCU A CCUUUGUU | 2761 | 1960 | CGGACUUU C GAUCUUCC |
| 2459 | 1912 | CCCUGCCU C CUCCCACA | 2765 | 1961 | CUUUUGCU C UGCGGCCU |
| 2460 | 1913 | CCUACCUU U GUUCCCAA | 2769 | 1962 | UUCUCUAU U ACCCUGC |
| 2479 | 1914 | UUACACCU A UUACCGCC | 2797 | 1963 | CGUGAAAU U AUGGUCAA |
| 2480 | 1915 | GUCGCCGU U GUGAUCCC | 2803 | 1964 | CUCAUGCU U CACAGAAC |
| 2483 | 1916 | ACCUUUGU U CCCAAUGU | 2804 | 1965 | UCAUGCUU C ACAGAACU |
| 2484 | 1917 | CCUUUGUU C CCAAUGUC | 2813 | 1966 | GCUCCCAU C CUGACCCU |
| 2492 | 1918 | GACCACCU C CCCACCUA | 2815 | 1967 | CGGACUUU C GAUCUUCC |
| 2504 | 1919 | ACCUACAU A CAUUCCUA | 2821 | 1968 | CCUGACCU C CUGGAGGU |
| 2508 | 1920 | ACAUACAU U CCUACCUU | 2822 | 1969 | UACAACUU U UCAGCUCC |
| 2509 | 1921 | CAUACAUU C CUACCUUU | 2823 | 1970 | CAACUUUU C AGCUCCCA |
| 2510 | 1922 | GUCCAUUU A CACCUAUU | 2829 | 1971 | UCGGUGCU C AGGUAUCC |
| 2520 | 1923 | ACCUUUGU U CCCAAUGU | 2837 | 1972 | CACAGGGU A CUUCCCCC |
| 2521 | 1924 | CCUUUGUU C CCAAUGUC | 2840 | 1973 | GCACCCCU C CCAGCGCA |
| 2533 | 1925 | ACAGCAUU U ACCCCUCA | 2847 | 1974 | UUACCCCU C ACCCACCU |
| 2540 | 1926 | UCGGUGCU C AGGUAUCC | 2853 | 1975 | UUCGAUCU U CCGACUAG |
| 2545 | 1927 | AGGCAGCU C CGGACUUU | 2860 | 1976 | UCUUGUGU U CCCUGGAA |
| 2568 | 1928 | CAGAGAUU U UGUGUCAG | 2872 | 1977 | GGGCCUGU C GGUGCUCA |
| 2579 | 1929 | CCUGCACU U UGCCCUGG | 2877 | 1978 | UGGAGUCU C CCAGCACC |
| 2585 | 1930 | CUGCUCGU A GACCUCUC | 2899 | 1979 | AGGCAGCU C CGGACUUU |
| 2588 | 1931 | UGCCUCCU C CCACAGCC | 2900 | 1980 | GGCUGACU U CCUUCUCU |
| 2591 | 1932 | CUCUUCCU C UUGCGAAG | 2904 | 1981 | GAACUGCU C UUCCUCUU |
| 2593 | 1933 | UCUCUAUU A CCCCUGCU | 2905 | 1982 | GGCUGACU U CCUUCUCU |
| 2596 | 1934 | CUCCUGGU C CUGGUCGC | 2906 | 1983 | GUUGAUGU A UUUAUUAA |
| 2601 | 1935 | UGUGCUAU A UGGUCCUC | 2907 | 1984 | CUGCUCUU C CUCUUGCG |
| 2602 | 1936 | GUCCUGGU C GCCGUUGU | 2908 | 1985 | UGAUGUAU U UAUUAAUU |
| 2607 | 1937 | GUGGGAGU A UCACCAGG | 2909 | 1986 | GAACUGCU C UUCCUCUU |
| 2608 | 1938 | CUUUAGCU C CCGUGGGA | 2910 | 1987 | ACUUCCUU C UCUAUUAC |
| 2609 | 1939 | UGGAGACU A ACUGGAUG | 2911 | 1988 | UUCCUUCU C UAUUACCC |
| 2620 | 1940 | UCAGAGUU C UGACAGUU | 2912 | 1989 | AUGUAUUU A UUAAUUCA |
| 2626 | 1941 | CUCUCAGU A GUGCUGCU | 2913 | 1990 | UGUGUAUU C GUUCCCAG |
| 2628 | 1942 | UACAACUU U UCAGCUCC | 2914 | 1991 | GUAUUUAU U AAUUCAGA |
| 2635 | 1943 | UCACAGAU C CAAUUCAC | 2915 | 1992 | UAUUUAUU A AUUCAGAG |
| 2640 | 1944 | GCUCAGGU A UCCAUCCA | 2916 | 1993 | CUCUUCCU C UUGCGAAG |
| 2641 | 1945 | CCCCACCU A CAUACAUU | 2917 | 1994 | CUUCCUCU U GCGAAGAC |
| 2642 | 1946 | GCCUGUUU C CUGCCUCU | 2918 | 1995 | AUUUCUUU C ACGAGUCA |
| 2653 | 1947 | CCACAGGU C AGGGUGCU | 2919 | 1996 | UUUUGUGU C AGCCACUG |
| 2659 | 1948 | AGAAGGGU C CUGCAAGC | 2931 | 1997 | GAUGGUGU C CCGCUGCC |
| 2689 | 1949 | ACUAGGGU C CUGAAGCU | 2933 | 1998 | UGGAGUCU C CCAGCACC |
| 2691 | 1950 | UCAGGCCU A AGAGGACU | 2941 | 1999 | CAGUACUU C CCCCAGGC |
| 2700 | 1951 | AGGGUACU U CCCCAGG | 2951 | 2000 | ACCAUGCU U CCUCUGAC |
| 2704 | 1952 | GACCACCU C CCCACCUA | 2952 | 2001 | CCGGACUU U CGAUCUUC |

55

| 2711 | 1953 | CCCUACCU U AGGAAGGU | 2955 | 2002 | UGCUUCCU C UGACAUGG |
|------|------|---------------------|------|------|---------------------|
| 2712 | 1954 | CCUACCUU A GGAAGGUG | 2956 | 2003 | CUUUCCUU U GAAUCAAU |
| 2721 | 1955 | GGAAAGAU C AUACGGGU | 2961 | 2004 | UUUUGUGU C AGCCACUG |
| 2724 | 1956 | AAGAUCAU A CGGGUUUG | 2962 | 2005 | UGUGUAUU C GUUCCCAG |
| 2744 | 1957 | GGGUGGAU C CGUGCAGG | 2965 | 2006 | CUUUGAAU C AAUAAAGU |
| 2750 | 1958 | GUCCCUGU U UAAAAACC | 2966 | 2007 | UGGAAGCU C UUCAAGCU |
| 2759 | 1959 | GACGAACU A UCGAGUGG | 2969 | 2008 | GAAUCAAU A AAGUUUUA |
| 2975 | 2009 | UGGAAGCU C UUCAAGCU | | | |
| 2976 | 2010 | UAUAUGGU C CUCACCUG | | | |
| 2977 | 2011 | GAAGCUCU U CAAGCUGA | | | |

Table X: Rat ICAM HH Ribozyme Sequences

| nt. Position | SEQ ID NO | Rat HH Ribozyme Sequence |
|---|---|---|
| 11 | 2012 | UCAGUGUG CUGAUGAGGCCGAAAGGCCGAA AUUGGAUC |
| 23 | 2013 | UAGAGAAG CUGAUGAGGCCGAAAGGCCGAA AAGUCAGC |
| 26 | 2014 | AAGAGGAA CUGAUGAGGCCGAAAGGCCGAA AGCAGUUC |
| 31 | 2015 | AGGACCAG CUGAUGAGGCCGAAAGGCCGAA AGCAGAGG |
| 34 | 2016 | GUAUAUCU CUGAUGAGGCCGAAAGGCCGAA AGCUUCAG |
| 40 | 2017 | GGGGCUUG CUGAUGAGGCCGAAAGGCCGAA ACCUUGAG |
| 48 | 2018 | CCCAGGCC CUGAUGAGGCCGAAAGGCCGAA AGGUUCUC |
| 54 | 2019 | GGCUCAGG CUGAUGAGGCCGAAAGGCCGAA AGGCGGGG |
| 58 | 2020 | GGGAGCUA CUGAUGAGGCCGAAAGGCCGAA AGGCACGG |
| 64 | 2021 | ACGGGUUG CUGAUGAGGCCGAAAGGCCGAA AGCCAUUG |
| 96 | 2022 | AGGACCAG CUGAUGAGGCCGAAAGGCCGAA AGCAGAGG |
| 102 | 2023 | GCGACCAG CUGAUGAGGCCGAAAGGCCGAA ACCAGGAG |
| 108 | 2024 | AGUUCCCC CUGAUGAGGCCGAAAGGCCGAA AGCAGUCC |
| 115 | 2025 | UGGGAACA CUGAUGAGGCCGAAAGGCCGAA AGGUAGGA |
| 119 | 2026 | GAGUUGGG CUGAUGAGGCCGAAAGGCCGAA ACAGUGUC |
| 120 | 2027 | GGCCCGGG CUGAUGAGGCCGAAAGGCCGAA AUCACAAC |
| 146 | 2028 | GGAGUUCC CUGAUGAGGCCGAAAGGCCGAA AGGUCUGG |
| 152 | 2029 | UUGAGGUG CUGAUGAGGCCGAAAGGCCGAA AGCCGGGU |
| 158 | 2030 | UGACUCGU CUGAUGAGGCCGAAAGGCCGAA AAAGAAAU |
| 165 | 2031 | GGGGGAAG CUGAUGAGGCCGAAAGGCCGAA ACUGUUCA |
| 168 | 2032 | CGAGGCAG CUGAUGAGGCCGAAAGGCCGAA AAGGCUUC |
| 185 | 2033 | CCUGCACG CUGAUGAGGCCGAAAGGCCGAA AUCCACCC |
| 209 | 2034 | GGUCAGAU CUGAUGAGGCCGAAAGGCCGAA AGGGGCUG |
| 227 | 2035 | UUCACAGU CUGAUGAGGCCGAAAGGCCGAA ACUUGGUC |
| 230 | 2036 | CCUCCCAC CUGAUGAGGCCGAAAGGCCGAA ACAGCUUG |
| 237 | 2037 | GGGGUGUC CUGAUGAGGCCGAAAGGCCGAA AGCUUCAG |
| 248 | 2038 | UCCUAAGG CUGAUGAGGCCGAAAGGCCGAA AGGGGGCC |
| 253 | 2039 | CCUCCACU CUGAUGAGGCCGAAAGGCCGAA AGGCAGUG |
| 263 | 2040 | GCAUGAGA CUGAUGAGGCCGAAAGGCCGAA AUUGGCUC |
| 267 | 2041 | CGAGGCAG CUGAUGAGGCCGAAAGGCCGAA AAGGCUUC |
| 293 | 2042 | UCAGCUUG CUGAUGAGGCCGAAAGGCCGAA AGAGCUUC |
| 319 | 2043 | UCGUUUGU CUGAUGAGGCCGAAAGGCCGAA AUCCUCCG |
| 335 | 2044 | AGUUCUCA CUGAUGAGGCCGAAAGGCCGAA AGCACAGU |
| 337 | 2045 | GAGGACCA CUGAUGAGGCCGAAAGGCCGAA AUAGCACA |
| 338 | 2046 | CUCAGCUU CUGAUGAGGCCGAAAGGCCGAA AAGAGCUU |
| 359 | 2047 | AAGCCGAG CUGAUGAGGCCGAAAGGCCGAA ACUGCGUG |
| 367 | 2048 | ACGGGUUG CUGAUGAGGCCGAAAGGCCGAA AGCCAUUG |
| 374 | 2049 | AGGUGGGU CUGAUGAGGCCGAAAGGCCGAA AGGGGUAA |
| 375 | 2050 | GAGGCAGG CUGAUGAGGCCGAAAGGCCGAA AGGCUUCU |
| 378 | 2051 | UACCCUGU CUGAUGAGGCCGAAAGGCCGAA AGGUGGGU |

57

| 386 | 2052 | AGCUCCAA CUGAUGAGGCCGAAAGGCCGAA ACACAGCG |
|---|---|---|
| 394 | 2053 | CUGUUCAG CUGAUGAGGCCGAAAGGCCGAA AGCACCAC |
| 420 | 2054 | UGCGCUGG CUGAUGAGGCCGAAAGGCCGAA AGGGGUGC |
| 425 | 2055 | GGUGGCAG CUGAUGAGGCCGAAAGGCCGAA AGCCGAGG |
| 427 | 2056 | UGGUUUUU CUGAUGAGGCCGAAAGGCCGAA AACAGGGA |
| 450 | 2057 | CGCAGGAU CUGAUGAGGCCGAAAGGCCGAA AGGUUCUU |
| 451 | 2058 | GCCUGGGG CUGAUGAGGCCGAAAGGCCGAA AAGUACCC |
| 456 | 2059 | UGGUGGCA CUGAUGAGGCCGAAAGGCCGAA AAGCCGAG |
| 495 | 2060 | UACACAGU CUGAUGAGGCCGAAAGGCCGAA AUGGUGGC |
| 510 | 2061 | UUCCCACG CUGAUGAGGCCGAAAGGCCGAA AGCAGCAC |
| 564 | 2062 | GUGGUUGG CUGAUGAGGCCGAAAGGCCGAA ACAUUUUC |
| 592 | 2063 | UCCCUGGU CUGAUGAGGCCGAAAGGCCGAA AUACUCCC |
| 607 | 2064 | GCAUGAGA CUGAUGAGGCCGAAAGGCCGAA AUUGGCUC |
| 608 | 2065 | AGCAUGAG CUGAUGAGGCCGAAAGGCCGAA AAUUGGCU |
| 609 | 2066 | AAGCAUGA CUGAUGAGGCCGAAAGGCCGAA AAAUUGGC |
| 611 | 2067 | UGAAGCAU CUGAUGAGGCCGAAAGGCCGAA AGAAAUUG |
| 656 | 2068 | CAUUCUUG CUGAUGAGGCCGAAAGGCCGAA ACAGUGAC |
| 657 | 2069 | ACAUUCUU CUGAUGAGGCCGAAAGGCCGAA AACAGUGA |
| 668 | 2070 | AAGAGGAA CUGAUGAGGCCGAAAGGCCGAA AGCAGUUC |
| 677 | 2071 | UGCGCUGG CUGAUGAGGCCGAAAGGCCGAA AGGGGUGC |
| 684 | 2072 | AAAGUCCG CUGAUGAGGCCGAAAGGCCGAA AGCUGCCU |
| 692 | 2073 | GGAGUUCC CUGAUGAGGCCGAAAGGCCGAA AGGUCUGG |
| 693 | 2074 | GGAAGAUC CUGAUGAGGCCGAAAGGCCGAA AAAGUCCG |
| 696 | 2075 | AGAGGCAG CUGAUGAGGCCGAAAGGCCGAA AAACAGGC |
| 709 | 2076 | GUGAGGGG CUGAUGAGGCCGAAAGGCCGAA AAAUGCUG |
| 720 | 2077 | GAGCUGAA CUGAUGAGGCCGAAAGGCCGAA AGUUGUAG |
| 723 | 2078 | UGGGAGCU CUGAUGAGGCCGAAAGGCCGAA AAAAGUUG |
| 735 | 2079 | GCGACCAG CUGAUGAGGCCGAAAGGCCGAA ACCAGGAG |
| 738 | 2080 | UCCACCCC CUGAUGAGGCCGAAAGGCCGAA AGGCAGGA |
| 765 | 2081 | AGUUCUCA CUGAUGAGGCCGAAAGGCCGAA AGCACAGU |
| 769 | 2082 | UUCCAGGG CUGAUGAGGCCGAAAGGCCGAA ACACAAGA |
| 770 | 2083 | CUUCCAGG CUGAUGAGGCCGAAAGGCCGAA AACACAAG |
| 785 | 2084 | AGGCAGGA CUGAUGAGGCCGAAAGGCCGAA ACAGGCCU |
| 786 | 2085 | GAGGCAGG CUGAUGAGGCCGAAAGGCCGAA AACAGGCC |
| 792 | 2086 | GCGACCAG CUGAUGAGGCCGAAAGGCCGAA ACCAGGAG |
| 794 | 2087 | GAGCUUCA CUGAUGAGGCCGAAAGGCCGAA AGGCAGGA |
| 807 | 2088 | UCCAGGUA CUGAUGAGGCCGAAAGGCCGAA AUCUGAGC |
| 833 | 2089 | UAGUCUCC CUGAUGAGGCCGAAAGGCCGAA ACCCCAGG |
| 846 | 2090 | CAAUAAAU CUGAUGAGGCCGAAAGGCCGAA ACUGUCAG |
| 851 | 2091 | AGCUGCUA CUGAUGAGGCCGAAAGGCCGAA AGGUGAGC |
| 863 | 2092 | ACGGGUUG CUGAUGAGGCCGAAAGGCCGAA AGCCAUUG |
| 866 | 2093 | UGUCAGAG CUGAUGAGGCCGAAAGGCCGAA AAGCAUGG |
| 867 | 2094 | UAGGUGGG CUGAUGAGGCCGAAAGGCCGAA AGGUGGUC |
| 869 | 2095 | CUUCGCAA CUGAUGAGGCCGAAAGGCCGAA AGGAAGAG |
| 881 | 2096 | CACGGGUU CUGAUGAGGCCGAAAGGCCGAA AAGCCAUU |
| 885 | 2097 | UUCACAGU CUGAUGAGGCCGAAAGGCCGAA ACUUGGUC |
| 933 | 2098 | CUGGGAAC CUGAUGAGGCCGAAAGGCCGAA AAUACACA |

58

| | | |
|---|---|---|
| 936 | 2099 | UGACACAA CUGAUGAGGCCGAAAGGCCGAA AUCUCUGC |
| 978 | 2100 | AAGUUGUA CUGAUGAGGCCGAAAGGCCGAA AUUCUCAA |
| 980 | 2101 | AAAAGUUG CUGAUGAGGCCGAAAGGCCGAA AGAUUCUC |
| 986 | 2102 | GAGCUGAA CUGAUGAGGCCGAAAGGCCGAA AGUUGUAG |
| 987 | 2103 | GGAGCUGA CUGAUGAGGCCGAAAGGCCGAA AAGUUGUA |
| 988 | 2104 | GGGAGCUG CUGAUGAGGCCGAAAGGCCGAA AAAGUUGU |
| 1005 | 2105 | GACGCCAC CUGAUGAGGCCGAAAGGCCGAA AUCACGAA |
| 1006 | 2106 | CCUGGUGA CUGAUGAGGCCGAAAGGCCGAA ACUCCCAC |
| 1023 | 2107 | CCUUCUGA CUGAUGAGGCCGAAAGGCCGAA ACCUCCGG |
| 1025 | 2108 | CCCCUUCU CUGAUGAGGCCGAAAGGCCGAA AGACCUCC |
| 1066 | 2109 | UUGGGAAC CUGAUGAGGCCGAAAGGCCGAA AAGGUAGG |
| 1092 | 2110 | UCUGCUGA CUGAUGAGGCCGAAAGGCCGAA ACCCCUCU |
| 1093 | 2111 | AGGGGCUG CUGAUGAGGCCGAAAGGCCGAA AUUCCCCU |
| 1125 | 2112 | AUCAACAA CUGAUGAGGCCGAAAGGCCGAA AGUUGGGG |
| 1163 | 2113 | AGCAAAAG CUGAUGAGGCCGAAAGGCCGAA AGCGUCGU |
| 1164 | 2114 | GAGCAAAA CUGAUGAGGCCGAAAGGCCGAA AAGCGUCG |
| 1166 | 2115 | CAGAGCAA CUGAUGAGGCCGAAAGGCCGAA AGAAGCGU |
| 1172 | 2116 | AGGCCGCA CUGAUGAGGCCGAAAGGCCGAA AGCAAAAG |
| 1200 | 2117 | UUCAGUGU CUGAUGAGGCCGAAAGGCCGAA AAUUGGAU |
| 1201 | 2118 | CCUGUGGA CUGAUGAGGCCGAAAGGCCGAA AAGCCCAA |
| 1203 | 2119 | GACCUGUG CUGAUGAGGCCGAAAGGCCGAA AGAAGCCC |
| 1227 | 2120 | AGCACAUG CUGAUGAGGCCGAAAGGCCGAA AGUUCCAA |
| 1228 | 2121 | ACGAUCAC CUGAUGAGGCCGAAAGGCCGAA AAGCCCGC |
| 1233 | 2122 | GCGACCAG CUGAUGAGGCCGAAAGGCCGAA ACCAGGAG |
| 1238 | 2123 | GAGGACCA CUGAUGAGGCCGAAAGGCCGAA AUAGCACA |
| 1264 | 2124 | ACCCGUAU CUGAUGAGGCCGAAAGGCCGAA AUCUUUCC |
| 1267 | 2125 | CAUUCUUG CUGAUGAGGCCGAAAGGCCGAA ACAGUGAC |
| 1294 | 2126 | CUGACACA CUGAUGAGGCCGAAAGGCCGAA AAUCUCUG |
| 1295 | 2127 | UCUGCUGA CUGAUGAGGCCGAAAGGCCGAA ACCCCUCU |
| 1306 | 2128 | GCAUGUAA CUGAUGAGGCCGAAAGGCCGAA AGUCUGCU |
| 1321 | 2129 | UUUCCCCA CUGAUGAGGCCGAAAGGCCGAA ACUCUGUU |
| 1334 | 2130 | GCUCUGGG CUGAUGAGGCCGAAAGGCCGAA ACGAAUAC |
| 1344 | 2131 | GGAUACCU CUGAUGAGGCCGAAAGGCCGAA AGCACCGA |
| 1351 | 2132 | AGUCCUCU CUGAUGAGGCCGAAAGGCCGAA AGGCCUGA |
| 1353 | 2133 | CCAUUGUU CUGAUGAGGCCGAAAGGCCGAA AGCUGCUA |
| 1366 | 2134 | CCUGGGGG CUGAUGAGGCCGAAAGGCCGAA AGUACCCU |
| 1367 | 2135 | GCCUGGGG CUGAUGAGGCCGAAAGGCCGAA AAGUACCC |
| 1368 | 2136 | GGCAGCGG CUGAUGAGGCCGAAAGGCCGAA ACACCAUC |
| 1380 | 2137 | ACCAUCCC CUGAUGAGGCCGAAAGGCCGAA AUAGGCAG |
| 1388 | 2138 | CAUCCAGU CUGAUGAGGCCGAAAGGCCGAA AGUCUCCA |
| 1398 | 2139 | UGUCCUGU CUGAUGAGGCCGAAAGGCCGAA ACAGCCAG |
| 1402 | 2140 | CAGUUCUC CUGAUGAGGCCGAAAGGCCGAA AAGCACAG |
| 1408 | 2141 | GACGCCAC CUGAUGAGGCCGAAAGGCCGAA AUCACGAA |
| 1410 | 2142 | GUCCACUC CUGAUGAGGCCGAAAGGCCGAA AUAGUUCG |
| 1421 | 2143 | GCCUGGGG CUGAUGAGGCCGAAAGGCCGAA AAGUACCC |
| 1425 | 2144 | AGCCAGAG CUGAUGAGGCCGAAAGGCCGAA AGGUGGGU |
| 1429 | 2145 | CCUGAGGC CUGAUGAGGCCGAAAGGCCGAA ACAAGUAU |

59

| 1444 | 2146 | CUCCUCCU CUGAUGAGGCCGAAAGGCCGAA AGCCUUCU |
|---|---|---|
| 1455 | 2147 | UCCCUGGU CUGAUGAGGCCGAAAGGCCGAA AUACUCCC |
| 1482 | 2148 | CCUGGGGG CUGAUGAGGCCGAAAGGCCGAA AGUACCCU |
| 1484 | 2149 | GCAAGAGG CUGAUGAGGCCGAAAGGCCGAA AGAGCAGU |
| 1493 | 2150 | UAGUCUCC CUGAUGAGGCCGAAAGGCCGAA ACCCCAGG |
| 1500 | 2151 | UUGACCAU CUGAUGAGGCCGAAAGGCCGAA AUUUCACG |
| 1503 | 2152 | GUGGUUGG CUGAUGAGGCCGAAAGGCCGAA ACAUUUUC |
| 1506 | 2153 | CCAACAAU CUGAUGAGGCCGAAAGGCCGAA AUGACCCA |
| 1509 | 2154 | UACACAGU CUGAUGAGGCCGAAAGGCCGAA AUGGUGGC |
| 1518 | 2155 | ACAACGGC CUGAUGAGGCCGAAAGGCCGAA ACCAGGAC |
| 1530 | 2156 | ACAAUUAU CUGAUGAGGCCGAAAGGCCGAA ACCCAGGU |
| 1533 | 2157 | AAGCCCGC CUGAUGAGGCCGAAAGGCCGAA AUGAUCAG |
| 1551 | 2158 | UACGAGCA CUGAUGAGGCCGAAAGGCCGAA AGGGCCAC |
| 1559 | 2159 | UAAACAGG CUGAUGAGGCCGAAAGGCCGAA ACUUCCCA |
| 1563 | 2160 | UGGGAACA CUGAUGAGGCCGAAAGGCCGAA AGGUAGGA |
| 1565 | 2161 | GGCGGUAA CUGAUGAGGCCGAAAGGCCGAA AGGUGUAA |
| 1567 | 2162 | CUGGCGGU CUGAUGAGGCCGAAAGGCCGAA AUAGGUGU |
| 1584 | 2163 | UAUAUCCU CUGAUGAGGCCGAAAGGCCGAA AUCUUCCU |
| 1592 | 2164 | GUAACUUG CUGAUGAGGCCGAAAGGCCGAA AUAUCCUG |
| 1599 | 2165 | GCCUUCUG CUGAUGAGGCCGAAAGGCCGAA AACUUGUA |
| 1651 | 2166 | GGCUCAGG CUGAUGAGGCCGAAAGGCCGAA AGGCGGGG |
| 1661 | 2167 | ACCAGGGC CUGAUGAGGCCGAAAGGCCGAA AAGUGCAG |
| 1663 | 2168 | UGUCCAUU CUGAUGAGGCCGAAAGGCCGAA AUCUGUUC |
| 1678 | 2169 | CCCAGGCC CUGAUGAGGCCGAAAGGCCGAA AGGUUCUC |
| 1680 | 2170 | GACCUGUG CUGAUGAGGCCGAAAGGCCGAA AGAAGCCC |
| 1681 | 2171 | GAGGCAGG CUGAUGAGGCCGAAAGGCCGAA AACAGGCC |
| 1684 | 2172 | GAGAGGUC CUGAUGAGGCCGAAAGGCCGAA ACGAGCAG |
| 1690 | 2173 | AAUGUAUG CUGAUGAGGCCGAAAGGCCGAA AGGUGGGG |
| 1691 | 2174 | GAAGAUCG CUGAUGAGGCCGAAAGGCCGAA AAGUCCGG |
| 1696 | 2175 | GCGACCAG CUGAUGAGGCCGAAAGGCCGAA ACCAGGAG |
| 1698 | 2176 | UCUCCAGG CUGAUGAGGCCGAAAGGCCGAA AUAUCUGA |
| 1737 | 2177 | GCACCGUG CUGAUGAGGCCGAAAGGCCGAA AUGUGAUC |
| 1750 | 2178 | AAUAGGUG CUGAUGAGGCCGAAAGGCCGAA AAAUGGAC |
| 1756 | 2179 | AGGACCAG CUGAUGAGGCCGAAAGGCCGAA AGCAGAGG |
| 1787 | 2180 | CCCAGGCC CUGAUGAGGCCGAAAGGCCGAA AGGUUCUC |
| 1790 | 2181 | GAGUUGGG CUGAUGAGGCCGAAAGGCCGAA ACAGUGUC |
| 1793 | 2182 | GUCCAGGU CUGAUGAGGCCGAAAGGCCGAA AGGACCAU |
| 1797 | 2183 | UGGUUUUU CUGAUGAGGCCGAAAGGCCGAA AACAGGGA |
| 1802 | 2184 | UCCAGGUA CUGAUGAGGCCGAAAGGCCGAA AUCUGAGC |
| 1812 | 2185 | UUUCCCCA CUGAUGAGGCCGAAAGGCCGAA ACUCUGUU |
| 1813 | 2186 | ACGAUCAC CUGAUGAGGCCGAAAGGCCGAA AAGCCCGC |
| 1825 | 2187 | UACACAGU CUGAUGAGGCCGAAAGGCCGAA AUGGUGGC |
| 1837 | 2188 | UACCCUGU CUGAUGAGGCCGAAAGGCCGAA AGGUGGGU |
| 1845 | 2189 | GCCCUCC CUGAUGAGGCCGAAAGGCCGAA AGUCCUCU |
| 1856 | 2190 | GCAGGUCA CUGAUGAGGCCGAAAGGCCGAA AUUAGGGG |
| 1861 | 2191 | GGACCAUA CUGAUGAGGCCGAAAGGCCGAA AGCACAUG |
| 1865 | 2192 | CUUGUGUC CUGAUGAGGCCGAAAGGCCGAA ACCGGAUA |

60

| | | |
|---|---|---|
| 1868 | 2193 | AUUUAUAU CUGAUGAGGCCGAAAGGCCGAA ACUCGUGA |
| 1877 | 2194 | CCUGGGGG CUGAUGAGGCCGAAAGGCCGAA AGUACUGU |
| 1901 | 2195 | UGUACCUU CUGAUGAGGCCGAAAGGCCGAA AGUUUUAG |
| 1912 | 2196 | UGUCCAUU CUGAUGAGGCCGAAAGGCCGAA AUCUGUUC |
| 1922 | 2197 | UAGGCAAU CUGAUGAGGCCGAAAGGCCGAA ACUUACAU |
| 1923 | 2198 | CUAAAGGU CUGAUGAGGCCGAAAGGCCGAA AGCGUCCA |
| 1928 | 2199 | UCCAGGUA CUGAUGAGGCCGAAAGGCCGAA AUCUGAGC |
| 1930 | 2200 | CAUCCAGU CUGAUGAGGCCGAAAGGCCGAA AGUCUCCA |
| 1964 | 2201 | GCUGACAC CUGAUGAGGCCGAAAGGCCGAA AAAUCUCU |
| 1983 | 2202 | CCCAGGCC CUGAUGAGGCCGAAAGGCCGAA AGGUUCUC |
| 1996 | 2203 | AGCUUGAA CUGAUGAGGCCGAAAGGCCGAA AGCUUCCA |
| 2005 | 2204 | UAGGCAAU CUGAUGAGGCCGAAAGGCCGAA ACUUACAU |
| 2013 | 2205 | CAUCCCGA CUGAUGAGGCCGAAAGGCCGAA AGGCAGCG |
| 2015 | 2206 | ACCAUCCC CUGAUGAGGCCGAAAGGCCGAA AUAGGCAG |
| 2020 | 2207 | GUACAGGG CUGAUGAGGCCGAAAGGCCGAA ACUCAAUA |
| 2039 | 2208 | UCGUUUGU CUGAUGAGGCCGAAAGGCCGAA AUCCUCCG |
| 2040 | 2209 | ACCUCCAG CUGAUGAGGCCGAAAGGCCGAA AGGUCAGG |
| 2057 | 2210 | AGCCAUUG CUGAUGAGGCCGAAAGGCCGAA AGGACCAG |
| 2061 | 2211 | UAGGUGUA CUGAUGAGGCCGAAAGGCCGAA AUGGACGC |
| 2071 | 2212 | CCUGAGGC CUGAUGAGGCCGAAAGGCCGAA ACAAGUAU |
| 2076 | 2213 | UUAGGCCU CUGAUGAGGCCGAAAGGCCGAA AGGCUACA |
| 2097 | 2214 | ACAUCAAC CUGAUGAGGCCGAAAGGCCGAA AGAGUUGG |
| 2098 | 2215 | ACCUCCAG CUGAUGAGGCCGAAAGGCCGAA AGGUCAGG |
| 2115 | 2216 | CAGGACCC CUGAUGAGGCCGAAAGGCCGAA AGUCGGAA |
| 2128 | 2217 | GAUCAUGG CUGAUGAGGCCGAAAGGCCGAA ACAGCACU |
| 2130 | 2218 | AGAGGCAG CUGAUGAGGCCGAAAGGCCGAA AAACAGGC |
| 2145 | 2219 | ACAUCAAC CUGAUGAGGCCGAAAGGCCGAA AGAGUUGG |
| 2152 | 2220 | AAGUUGUA CUGAUGAGGCCGAAAGGCCGAA AUUCUCAA |
| 2156 | 2221 | UCAAUAAA CUGAUGAGGCCGAAAGGCCGAA AACUGUCA |
| 2158 | 2222 | AAUUAAUA CUGAUGAGGCCGAAAGGCCGAA AUACAUCA |
| 2159 | 2223 | GAAUUAAU CUGAUGAGGCCGAAAGGCCGAA AAUACAUC |
| 2160 | 2224 | UGAAUUAA CUGAUGAGGCCGAAAGGCCGAA AAAUACAU |
| 2162 | 2225 | AACAAAGG CUGAUGAGGCCGAAAGGCCGAA AGGAAUGU |
| 2163 | 2226 | CUCUGAAU CUGAUGAGGCCGAAAGGCCGAA AAUAAAUA |
| 2166 | 2227 | AAUUAAUA CUGAUGAGGCCGAAAGGCCGAA AUACAUCA |
| 2167 | 2228 | GAAUUAAU CUGAUGAGGCCGAAAGGCCGAA AAUACAUC |
| 2170 | 2229 | UCUGAAUU CUGAUGAGGCCGAAAGGCCGAA AUAAAUAC |
| 2171 | 2230 | UACUCAAU CUGAUGAGGCCGAAAGGCCGAA AAUAACUG |
| 2173 | 2231 | GAGGACCA CUGAUGAGGCCGAAAGGCCGAA AUAGCACA |
| 2174 | 2232 | AGCAGGGG CUGAUGAGGCCGAAAGGCCGAA AAUAGAGA |
| 2175 | 2233 | UGACUCGU CUGAUGAGGCCGAAAGGCCGAA AAAGAAAU |
| 2176 | 2234 | GUGGUUGG CUGAUGAGGCCGAAAGGCCGAA ACAUUUUC |
| 2183 | 2235 | UCAAUAAA CUGAUGAGGCCGAAAGGCCGAA AACUGUCA |
| 2185 | 2236 | ACUCAAUA CUGAUGAGGCCGAAAGGCCGAA AUAACUGU |
| 2186 | 2237 | UACUCAAU CUGAUGAGGCCGAAAGGCCGAA AAUAACUG |
| 2187 | 2238 | GUACUCAA CUGAUGAGGCCGAAAGGCCGAA AAAUAACU |
| 2189 | 2239 | GGGUACUC CUGAUGAGGCCGAAAGGCCGAA AUAAAUAA |

61

| | | |
|---|---|---|
| 2196 | 2240 | CAAUAAAU CUGAUGAGGCCGAAAGGCCGAA ACUGUCAG |
| 2198 | 2241 | UGACCUCG CUGAUGAGGCCGAAAGGCCGAA AGACAUUC |
| 2199 | 2242 | CUGGCAUG CUGAUGAGGCCGAAAGGCCGAA AAGAGUCU |
| 2200 | 2243 | GCCUGGGG CUGAUGAGGCCGAAAGGCCGAA AAGUACCC |
| 2201 | 2244 | GACCUGUG CUGAUGAGGCCGAAAGGCCGAA AGAAGCCC |
| 2205 | 2245 | CAGUGGCU CUGAUGAGGCCGAAAGGCCGAA ACACAAAA |
| 2210 | 2246 | CAUCCAGU CUGAUGAGGCCGAAAGGCCGAA AGUCUCCA |
| 2220 | 2247 | CCCAGGCC CUGAUGAGGCCGAAAGGCCGAA AGGUUCUC |
| 2224 | 2248 | AAGGUAGG CUGAUGAGGCCGAAAGGCCGAA AUGUAUGU |
| 2226 | 2249 | UGUGGCCU CUGAUGAGGCCGAAAGGCCGAA AGGUCCAG |
| 2233 | 2250 | AGUUCUGU CUGAUGAGGCCGAAAGGCCGAA AAGCAUGA |
| 2242 | 2251 | ACUACUGA CUGAUGAGGCCGAAAGGCCGAA AGCUGUGU |
| 2248 | 2252 | GCGACCAG CUGAUGAGGCCGAAAGGCCGAA ACCAGGAG |
| 2254 | 2253 | UUCAGUGU CUGAUGAGGCCGAAAGGCCGAA AAUUGGAU |
| 2259 | 2254 | GCACCGUG CUGAUGAGGCCGAAAGGCCGAA AUGUGAUC |
| 2260 | 2255 | AGCACCGU CUGAUGAGGCCGAAAGGCCGAA AAUGUGAU |
| 2266 | 2256 | AACUUGUA CUGAUGAGGCCGAAAGGCCGAA AUCCUGAU |
| 2274 | 2257 | UACAUGUU CUGAUGAGGCCGAAAGGCCGAA ACCUGCUC |
| 2279 | 2258 | ACCCGUAU CUGAUGAGGCCGAAAGGCCGAA AUCUUUCC |
| 2282 | 2259 | ACUCAAUA CUGAUGAGGCCGAAAGGCCGAA AUAACUGU |
| 2288 | 2260 | CAUUGGAG CUGAUGAGGCCGAAAGGCCGAA ACCAGGGC |
| 2291 | 2261 | GUAACUUG CUGAUGAGGCCGAAAGGCCGAA AUAUCCUG |
| 2321 | 2262 | ACCCGUAU CUGAUGAGGCCGAAAGGCCGAA AUCUUUCC |
| 2338 | 2263 | CCUGUGGA CUGAUGAGGCCGAAAGGCCGAA AAGCCCAA |
| 2339 | 2264 | GCCUGGGG CUGAUGAGGCCGAAAGGCCGAA AAGUACCC |
| 2341 | 2265 | UGAGCACC CUGAUGAGGCCGAAAGGCCGAA ACAGGCCC |
| 2344 | 2266 | GAGAGGUC CUGAUGAGGCCGAAAGGCCGAA ACGAGCAG |
| 2358 | 2267 | UGUGGGAG CUGAUGAGGCCGAAAGGCCGAA AGGCAGGG |
| 2359 | 2268 | UUCUGUGG CUGAUGAGGCCGAAAGGCCGAA AUGGAUGG |
| 2360 | 2269 | CUUCCAGG CUGAUGAGGCCGAAAGGCCGAA AACACAAG |
| 2376 | 2270 | AAGAGGAA CUGAUGAGGCCGAAAGGCCGAA AGCAGUUC |
| 2377 | 2271 | UAAUAGAG CUGAUGAGGCCGAAAGGCCGAA AGGAAGUC |
| 2378 | 2272 | UCGUGAAA CUGAUGAGGCCGAAAGGCCGAA AAAUCAGC |
| 2379 | 2273 | CGCAAGAG CUGAUGAGGCCGAAAGGCCGAA AAGAGCAG |
| 2380 | 2274 | ACUCGUGA CUGAUGAGGCCGAAAGGCCGAA AGAAAUCA |
| 2382 | 2275 | UGACUCGU CUGAUGAGGCCGAAAGGCCGAA AAAGAAAU |
| 2384 | 2276 | CUUGUGUC CUGAUGAGGCCGAAAGGCCGAA ACCGGAUA |
| 2399 | 2277 | CGUCCACA CUGAUGAGGCCGAAAGGCCGAA AGUAUUUA |
| 2401 | 2278 | GAGGACCA CUGAUGAGGCCGAAAGGCCGAA AUAGCACA |
| 2411 | 2279 | UGAAGCAU CUGAUGAGGCCGAAAGGCCGAA AGAAAUUG |
| 2417 | 2280 | AACUUGUA CUGAUGAGGCCGAAAGGCCGAA AUCCUGAU |
| 2418 | 2281 | AGUUCUGU CUGAUGAGGCCGAAAGGCCGAA AAGCAUGA |
| 2425 | 2282 | GAACUCUG CUGAUGAGGCCGAAAGGCCGAA AUUAAUAA |
| 2426 | 2283 | UAGUCUCC CUGAUGAGGCCGAAAGGCCGAA ACCCCAGG |
| 2433 | 2284 | AACUGUCA CUGAUGAGGCCGAAAGGCCGAA AACUCUGA |
| 2434 | 2285 | UCGUUUGU CUGAUGAGGCCGAAAGGCCGAA AUCCUCCG |
| 2448 | 2286 | GGGGGAAG CUGAUGAGGCCGAAAGGCCGAA ACUGUUCA |

62

| | | |
|---|---|---|
| 2449 | 2287 | CGAGGCAG CUGAUGAGGCCGAAAGGCCGAA AAGGCUUC |
| 2451 | 2288 | GAGGCAGG CUGAUGAGGCCGAAAGGCCGAA AACAGGCC |
| 2452 | 2289 | AGAGGCAG CUGAUGAGGCCGAAAGGCCGAA AAACAGGC |
| 2455 | 2290 | AACAAAGG CUGAUGAGGCCGAAAGGCCGAA AGGAAUGU |
| 2459 | 2291 | UGUGGGAG CUGAUGAGGCCGAAAGGCCGAA AGGCAGGG |
| 2460 | 2292 | UUGGGAAC CUGAUGAGGCCGAAAGGCCGAA AAGGUAGG |
| 2479 | 2293 | GGCGGUAA CUGAUGAGGCCGAAAGGCCGAA AGGUGUAA |
| 2480 | 2294 | GGGAUCAC CUGAUGAGGCCGAAAGGCCGAA ACGGCGAC |
| 2483 | 2295 | ACAUUGGG CUGAUGAGGCCGAAAGGCCGAA ACAAAGGU |
| 2484 | 2296 | GACAUUGG CUGAUGAGGCCGAAAGGCCGAA AACAAAGG |
| 2492 | 2297 | UAGGUGGG CUGAUGAGGCCGAAAGGCCGAA AGGUGGUC |
| 2504 | 2298 | UAGGAAUG CUGAUGAGGCCGAAAGGCCGAA AUGUAGGU |
| 2508 | 2299 | AAGGUAGG CUGAUGAGGCCGAAAGGCCGAA AUGUAUGU |
| 2509 | 2300 | AAAGGUAG CUGAUGAGGCCGAAAGGCCGAA AAUGUAUG |
| 2510 | 2301 | AAUAGGUG CUGAUGAGGCCGAAAGGCCGAA AAAUGGAC |
| 2520 | 2302 | ACAUUGGG CUGAUGAGGCCGAAAGGCCGAA ACAAAGGU |
| 2521 | 2303 | GACAUUGG CUGAUGAGGCCGAAAGGCCGAA AACAAAGG |
| 2533 | 2304 | UGAGGGGU CUGAUGAGGCCGAAAGGCCGAA AAUGCUGU |
| 2540 | 2305 | GGAUACCU CUGAUGAGGCCGAAAGGCCGAA AGCACCGA |
| 2545 | 2306 | AAAGUCCG CUGAUGAGGCCGAAAGGCCGAA AGCUGCCU |
| 2568 | 2307 | CUGACACA CUGAUGAGGCCGAAAGGCCGAA AAUCUCUG |
| 2579 | 2308 | CCAGGGCA CUGAUGAGGCCGAAAGGCCGAA AGUGCAGG |
| 2585 | 2309 | GAGAGGUC CUGAUGAGGCCGAAAGGCCGAA ACGAGCAG |
| 2588 | 2310 | GGCUGUGG CUGAUGAGGCCGAAAGGCCGAA AGGAGGCA |
| 2591 | 2311 | CUUCGCAA CUGAUGAGGCCGAAAGGCCGAA AGGAAGAG |
| 2593 | 2312 | AGCAGGGG CUGAUGAGGCCGAAAGGCCGAA AAUAGAGA |
| 2596 | 2313 | GCGACCAG CUGAUGAGGCCGAAAGGCCGAA ACCAGGAG |
| 2601 | 2314 | GAGGACCA CUGAUGAGGCCGAAAGGCCGAA AUAGCACA |
| 2602 | 2315 | ACAACGGC CUGAUGAGGCCGAAAGGCCGAA ACCAGGAC |
| 2607 | 2316 | CCUGGUGA CUGAUGAGGCCGAAAGGCCGAA ACUCCCAC |
| 2608 | 2317 | UCCCACGG CUGAUGAGGCCGAAAGGCCGAA AGCUAAAG |
| 2609 | 2318 | CAUCCAGU CUGAUGAGGCCGAAAGGCCGAA AGUCUCCA |
| 2620 | 2319 | AACUGUCA CUGAUGAGGCCGAAAGGCCGAA AACUCUGA |
| 2626 | 2320 | AGCAGCAC CUGAUGAGGCCGAAAGGCCGAA ACUGAGAG |
| 2628 | 2321 | GGAGCUGA CUGAUGAGGCCGAAAGGCCGAA AAGUUGUA |
| 2635 | 2322 | GUGAAUUG CUGAUGAGGCCGAAAGGCCGAA AUCUGUGA |
| 2640 | 2323 | UGGAUGGA CUGAUGAGGCCGAAAGGCCGAA ACCUGAGC |
| 2641 | 2324 | AAUGUAUG CUGAUGAGGCCGAAAGGCCGAA AGGUGGGG |
| 2642 | 2325 | AGAGGCAG CUGAUGAGGCCGAAAGGCCGAA AAACAGGC |
| 2653 | 2326 | AGCACCCU CUGAUGAGGCCGAAAGGCCGAA ACCUGUGG |
| 2659 | 2327 | GCUUGCAG CUGAUGAGGCCGAAAGGCCGAA ACCCUUCU |
| 2689 | 2328 | AGCUUCAG CUGAUGAGGCCGAAAGGCCGAA ACCCUAGU |
| 2691 | 2329 | AGUCCUCU CUGAUGAGGCCGAAAGGCCGAA AGGCCUGA |
| 2700 | 2330 | CCUGGGGG CUGAUGAGGCCGAAAGGCCGAA AGUACCCU |
| 2704 | 2331 | UAGGUGGG CUGAUGAGGCCGAAAGGCCGAA AGGUGGUC |
| 2711 | 2332 | ACCUUCCU CUGAUGAGGCCGAAAGGCCGAA AGGUAGGG |
| 2712 | 2333 | CACCUUCC CUGAUGAGGCCGAAAGGCCGAA AAGGUAGG |

63

| | | |
|---|---|---|
| 2721 | 2334 | ACCCGUAU CUGAUGAGGCCGAAAGGCCGAA AUCUUUCC |
| 2724 | 2335 | CAAACCCG CUGAUGAGGCCGAAAGGCCGAA AUGAUCUU |
| 2744 | 2336 | CCUGCACG CUGAUGAGGCCGAAAGGCCGAA AUCCACCC |
| 2750 | 2337 | GGUUUUUA CUGAUGAGGCCGAAAGGCCGAA ACAGGGAC |
| 2759 | 2338 | CCACUCGA CUGAUGAGGCCGAAAGGCCGAA AGUUCGUC |
| 2761 | 2339 | GGAAGAUC CUGAUGAGGCCGAAAGGCCGAA AAAGUCCG |
| 2765 | 2340 | AGGCCGCA CUGAUGAGGCCGAAAGGCCGAA AGCAAAAG |
| 2769 | 2341 | GCAGGGGU CUGAUGAGGCCGAAAGGCCGAA AUAGAGAA |
| 2797 | 2342 | UUGACCAU CUGAUGAGGCCGAAAGGCCGAA AUUUCACG |
| 2803 | 2343 | GUUCUGUG CUGAUGAGGCCGAAAGGCCGAA AGCAUGAG |
| 2804 | 2344 | AGUUCUGU CUGAUGAGGCCGAAAGGCCGAA AAGCAUGA |
| 2813 | 2345 | AGGGUCAG CUGAUGAGGCCGAAAGGCCGAA AUGGGAGC |
| 2815 | 2346 | GGAAGAUC CUGAUGAGGCCGAAAGGCCGAA AAAGUCCG |
| 2821 | 2347 | ACCUCCAG CUGAUGAGGCCGAAAGGCCGAA AGGUCAGG |
| 2822 | 2348 | GGAGCUGA CUGAUGAGGCCGAAAGGCCGAA AAGUUGUA |
| 2823 | 2349 | UGGGAGCU CUGAUGAGGCCGAAAGGCCGAA AAAAGUUG |
| 2829 | 2350 | GGAUACCU CUGAUGAGGCCGAAAGGCCGAA AGCACCGA |
| 2837 | 2351 | GGGGGAAG CUGAUGAGGCCGAAAGGCCGAA ACCCUGUG |
| 2840 | 2352 | UGCGCUGG CUGAUGAGGCCGAAAGGCCGAA AGGGGUGC |
| 2847 | 2353 | AGGUGGGU CUGAUGAGGCCGAAAGGCCGAA AGGGGUAA |
| 2853 | 2354 | CUAGUCGG CUGAUGAGGCCGAAAGGCCGAA AGAUCGAA |
| 2860 | 2355 | UUCCAGGG CUGAUGAGGCCGAAAGGCCGAA ACACAAGA |
| 2872 | 2356 | UGAGCACC CUGAUGAGGCCGAAAGGCCGAA ACAGGCCC |
| 2877 | 2357 | GGUGCUGG CUGAUGAGGCCGAAAGGCCGAA AGACUCCA |
| 2899 | 2358 | AAAGUCCG CUGAUGAGGCCGAAAGGCCGAA AGCUGCCU |
| 2900 | 2359 | AGAGAAGG CUGAUGAGGCCGAAAGGCCGAA AGUCAGCC |
| 2904 | 2360 | AAGAGGAA CUGAUGAGGCCGAAAGGCCGAA AGCAGUUC |
| 2905 | 2361 | AGAGAAGG CUGAUGAGGCCGAAAGGCCGAA AGUCAGCC |
| 2906 | 2362 | UUAAUAAA CUGAUGAGGCCGAAAGGCCGAA ACAUCAAC |
| 2907 | 2363 | CGCAAGAG CUGAUGAGGCCGAAAGGCCGAA AAGAGCAG |
| 2908 | 2364 | AAUUAAUA CUGAUGAGGCCGAAAGGCCGAA AUACAUCA |
| 2909 | 2365 | AAGAGGAA CUGAUGAGGCCGAAAGGCCGAA AGCAGUUC |
| 2910 | 2366 | GUAAUAGA CUGAUGAGGCCGAAAGGCCGAA AAGGAAGU |
| 2911 | 2367 | GGGUAAUA CUGAUGAGGCCGAAAGGCCGAA AGAAGGAA |
| 2912 | 2368 | UGAAUUAA CUGAUGAGGCCGAAAGGCCGAA AAAUACAU |
| 2913 | 2369 | CUGGGAAC CUGAUGAGGCCGAAAGGCCGAA AAUACACA |
| 2914 | 2370 | UCUGAAUU CUGAUGAGGCCGAAAGGCCGAA AUAAAUAC |
| 2915 | 2371 | CUCUGAAU CUGAUGAGGCCGAAAGGCCGAA AAUAAAUA |
| 2916 | 2372 | CUUCGCAA CUGAUGAGGCCGAAAGGCCGAA AGGAAGAG |
| 2917 | 2373 | GUCUUCGC CUGAUGAGGCCGAAAGGCCGAA AGAGGAAG |
| 2918 | 2374 | UGACUCGU CUGAUGAGGCCGAAAGGCCGAA AAAGAAAU |
| 2919 | 2375 | CAGUGGCU CUGAUGAGGCCGAAAGGCCGAA ACACAAAA |
| 2931 | 2376 | GGCAGCGG CUGAUGAGGCCGAAAGGCCGAA ACACCAUC |
| 2933 | 2377 | GGUGCUGG CUGAUGAGGCCGAAAGGCCGAA AGACUCCA |
| 2941 | 2378 | GCCUGGGG CUGAUGAGGCCGAAAGGCCGAA AAGUACUG |
| 2951 | 2379 | GUCAGAGG CUGAUGAGGCCGAAAGGCCGAA AGCAUGGU |
| 2952 | 2380 | GAAGAUCG CUGAUGAGGCCGAAAGGCCGAA AAGUCCGG |

64

| 2955 | 2381 | CCAUGUCA CUGAUGAGGCCGAAAGGCCGAA AGGAAGCA |
|------|------|------------------------------------------|
| 2956 | 2382 | AUUGAUUC CUGAUGAGGCCGAAAGGCCGAA AAGGAAAG |
| 2961 | 2383 | CAGUGGCU CUGAUGAGGCCGAAAGGCCGAA ACACAAAA |
| 2962 | 2384 | CUGGGAAC CUGAUGAGGCCGAAAGGCCGAA AAUACACA |
| 2965 | 2385 | ACUUUAUU CUGAUGAGGCCGAAAGGCCGAA AUUCAAAG |
| 2966 | 2386 | AGCUUGAA CUGAUGAGGCCGAAAGGCCGAA AGCUUCCA |
| 2969 | 2387 | UAAAACUU CUGAUGAGGCCGAAAGGCCGAA AUUGAUUC |
| 2975 | 2388 | AGCUUGAA CUGAUGAGGCCGAAAGGCCGAA AGCUUCCA |
| 2976 | 2389 | CAGGUGAG CUGAUGAGGCCGAAAGGCCGAA ACCAUAUA |
| 2977 | 2390 | UCAGCUUG CUGAUGAGGCCGAAAGGCCGAA AGAGCUUC |

What is claimed is:

1. An enzymatic nucleic acid molecule which specifically cleaves RNA having ICAM-1 sequence, wherein said enzymatic nucleic acid molecule comprises a substrate binding site and a nucleotide sequence within or surrounding said substrate binding site wherein said nucleotide sequence imparts to said enzymatic nucleic acid molecule activity for the cleavage of said RNA having ICAM-1 sequence.

2. The enzymatic nucleic acid molecule of claim 1, wherein said substrate binding site is complementary to said RNA having ICAM-1 sequence.

3. The enzymatic nucleic acid molecule of claim 1, wherein said enzymatic nucleic acid molecule is in a hammerhead motif.

4. The enzymatic nucleic acid molecule of claim 2, wherein said substrate binding site comprises between 12 and 100 nucleotides complementary to said RNA having ICAM-1 sequence.

5. The enzymatic nucleic acid molecule of claim 4, wherein said substrate binding site comprises between 14 and 24 nucleotides complementary to said RNA having ICAM-1 sequence.

6. An expression vector comprising nucleic acid sequence encoding one or more enzymatic nucleic acid molecules of claim 1 in a manner which allows expression of said enzymatic nucleic acid molecules.

7. The expression vector of claim 6, wherein said expression vector is a viral vector.

8. The expression vector of claim 7, wherein said viral vector is a retrovirus vector.

9. The enzymatic nucleic acid molecule of claim 1, wherein said enzymatic nucleic acid molecule is chemically synthesized.

10. The enzymatic nucleic acid molecule of claim 1, wherein said enzymatic nucleic acid molecule is active in the presence of divalent metal ions.

11. The enzymatic nucleic acid molecule of claim 10, wherein said divalent metal ion is magnesium.

12. The enzymatic nucleic acid molecule of claim 11, wherein said enzymatic nucleic acid molecule comprises a sugar modification.

13. The expression vector of claim 6, wherein said nucleic acid sequence encoding said enzymatic nucleic acid molecule is under the control of a mammalian transcription promoter.

14. The expression vector of claim 13, wherein said mammalian transcription promoter is a cytomegalovirus promoter.

15. The expression vector of claim 13, wherein said mammalian transcription promoter is a U6 small nuclear RNA promoter.

16. The enzymatic nucleic acid molecule of claim 1, wherein said enzymatic nucleic acid molecule comprises a 5'-cap.

17. The enzymatic nucleic acid molecule of claim 1, wherein said enzymatic nucleic acid molecule comprises a 3'-cap.

18. The enzymatic RNA molecule of claim 1, wherein said enzymatic nucleic acid molecule comprises a 3'-polyA tail.

19. A method of cleaving RNA having ICAM-1 sequence comprising contacting said RNA with the enzymatic nucleic acid molecule of claim 1 under conditions suitable for the cleavage of said RNA.

* * * * *